United States Patent
Keasling et al.

(10) Patent No.: US 7,192,751 B2
(45) Date of Patent: *Mar. 20, 2007

(54) BIOSYNTHESIS OF AMORPHA-4,11-DIENE

(75) Inventors: Jay Keasling, Berkeley, CA (US); Vincent Martin, Kensington, CA (US); Douglas Pitera, Oakland, CA (US); Sydnor T. Withers, III, Richmond, CA (US); Jack Newman, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/411,066

(22) Filed: Apr. 9, 2003

(65) Prior Publication Data

US 2004/0005678 A1 Jan. 8, 2004

Related U.S. Application Data

(63) Continuation-in-part of application No. 10/006,909, filed on Dec. 6, 2001.

(51) Int. Cl.
C12P 7/42 (2006.01)
C07H 21/04 (2006.01)
C12N 9/00 (2006.01)
C12N 1/20 (2006.01)
C12N 15/00 (2006.01)

(52) U.S. Cl. ............... 435/146; 435/41; 435/183; 435/194; 435/232; 435/252.3; 435/320.1; 536/23.2

(58) Field of Classification Search ........... 435/41, 435/146, 183, 189, 194, 232, 252.3, 320.1; 536/23.2
See application file for complete search history.

(56) References Cited

U.S. PATENT DOCUMENTS

| | | | |
|---|---|---|---|
| 6,072,045 A | 6/2000 | Chappell et al. | |
| 6,114,160 A | 9/2000 | Croteau et al. | |
| 6,190,895 B1 | 2/2001 | Croteau et al. | |
| 6,281,017 B1 | 8/2001 | Croteau et al. | |
| 6,284,506 B1 | 9/2001 | Hoshino et al. | |
| 6,291,745 B1 | 9/2001 | Meyer et al. | |
| 6,306,633 B1 | 10/2001 | Wilding et al. | |
| 6,495,354 B2 | 12/2002 | Chappell et al. | |
| 6,531,303 B1 | 3/2003 | Millis et al. | |
| 6,916,972 B2 | 7/2005 | Falco et al. | |
| 6,989,257 B2 | 1/2006 | Berry et al. | |
| 2003/0033626 A1 | 2/2003 | Hahn | |
| 2003/0148416 A1 | 8/2003 | Berry et al. | |
| 2004/0029239 A1 | 2/2004 | Ohto et al. | |
| 2004/0063182 A1 | 4/2004 | Ohto et al. | |
| 2004/0194162 A1 | 9/2004 | Hahn | |
| 2005/0241017 A1 | 10/2005 | Hahn | |
| 2005/0266518 A1 | 12/2005 | Berry et al. | |

FOREIGN PATENT DOCUMENTS

| | | |
|---|---|---|
| EP | 1360300 | 11/2003 |
| EP | 1392824 | 3/2004 |
| WO | WO0210398 | 2/2002 |
| WO | WO02099095 | 12/2002 |
| WO | WO0001650 | 1/2005 |

OTHER PUBLICATIONS

Bertea et al. Planta Med. Jan. 2005;71(1):40-7.*
66 FR 1099, Friday, Jan. 5, 2001.*
Tatiana et al. FEMS Microbiol Lett. May 15, 1999; 174(2): 247-250.*
Blast 2 Sequences results. Sequence 1 gi 5531936, Sequence 2, printed on Jun. 24, 2005.*
Takagi et al. J Bacteriol. Aug. 2000;182(15):4153-7.*
Wang et al. Accession AF119715. Apr. 22, 1999.*
Shimizu et al. Accession AB003187. Mar. 22, 1998.*
Mercke et al. Accession AF138959, Sep. 25, 2000.*
Balbas et al. Gene. Jun. 12, 1996;172(1):65-9.*
Hiser et al. J Biol Chem. Dec. 16, 1994;269(50):31383-9.*
Hiser et al. Accession L20428. Feb. 23, 1995.*
Altincicek et al. (2001), "GcpE Is Involved in the 2-C-Methyl-D-Erythritol 4-Phosphate Pathway of Isoprenoid Biosynthesis in *Escherichia coli*," *Journal of Bacteriology* 183(8):2411-2416.
Amann et al. (1988), "Tightly Regulated Tac Promoter Vectors Useful for the Expression of Unfused and Fused Proteins in *Escherichia coli*," *Gene* 69:301-315.
Barkovich et al (2001), "Metabolic Engineering of Isoprenoids," *Metabolic Engineering* 3(1):27-39.
Campos et al. (2001), "Identification of *gcpE* as a Novel Gene of the 2-C-Methyl-D-Erythritol 4-Phosphate Pathway for Isoprenoid Biosynthesis in *Escherichia coli*," *FEBS Letters* 488:170-173.
Campos et al. (2001), "*Escherichia coli* Engineered to Synthesize Isopentenyl Diphosphate and Dimethylallyl Diphosphate from Mevalonate: A Novel System for the Genetic Analysis of the 2-C-Methyl-D-Erythritol 4-Phosphate Pathway for Isoprenoid Biosynthesis," *Biochem. J.* 353:59-67.

(Continued)

*Primary Examiner*—Tekchand Saidha
*Assistant Examiner*—Christian L. Fronda
(74) *Attorney, Agent, or Firm*—Paula A. Borden; Bozicevic, Field & Francis LLP

(57) ABSTRACT

Methods for synthesizing amorpha-4,11-diene synthase from isopentenyl pyrophosphate are provided. A first method comprises introducing into a host microorganism a plurality of heterologous nucleic acid sequences, each coding for a different enzyme in the mevalonate pathway for producing isopentenyl pyrophosphate. Amorpha-4,11-diene synthase is then produced using an optimized amorpha-4,11-diene synthase gene. The invention also provides nucleic acid sequences, enzymes, expression vectors, and transformed host cells for carrying out the methods.

33 Claims, 12 Drawing Sheets

OTHER PUBLICATIONS

Cunningham et al. (1994), "Molecular Structure and Enzymatic Function of Lycopene Cyclase from the Cyanobacterium *Synechococcus* sp Strain PCC7942," *The Plant Cell* 6:1107-1121.

Dairi et al. (2001), "Eubacterial Diterpene Cyclase Genes Essential for Production of the Isoprenoid Antibiotic Terpentecin," *Journal of Bacteriology* 183(20):6085-6094.

Guzman et al. (1995), "Tight Regulation, Modulation, and High-Level Expression by Vectors Containing the Arabinose $P_{BAD}$ Promoter," *Journal of Bacteriology* 177(14):4121-4130.

Hahn et al. (1999), "*Escherichia coli* Open Reading Frame 696 Is *idi*, a Nonessential Gene Encoding Isopentenyl Diphosphate Isomerase," *Journal of Bacteriology* 181(15):4499-4504.

Hahn et al. (2001), "1-Deoxy-D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hamano et al. (2001), "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Kaneda et al. (2001), "An Unusual Isopentenyl Diphosphate Isomerase Found in the Mevalonate Pathway Gene Cluster from *Streptomyces* sp. Strain CL190," *PNAS* 98(3):932-937.

Kim et al. (2001), "Metabolic Engineering of the Nonmevalonate Isopentenyl Diphosphate Synthesis Pathway in *Escherichia coli* Enhances Lycopene Production," *Biotechnology and Bioengineering* 72(4):408-415.

Kovach et al. (1994), "pBBR1MCS: A Broad-Host-Range Cloning Vector," *BioTechniques* 16(5):800-802.

Kovach et al. (1995), "Four New Derivatives of the Broad-Host-Range Cloning Vector pBBR1MCS, Carrying Different Antibiotic-Resistance Cassettes," *Gene* 166:175-176.

Mahmoud et al. (2001), "Metabolic Engineering of Essential Oil Yield and Composition in Mint by Altering Expression of Deoxyxylulose Phosphate Reductoisomerase and Menthofuran Synthase," *PNAS* 8(15):8915-8920.

McAteer et al. (2001), "The *lytB* Gene of *Escherichia coli* Is Essential and Specifies a Product Needed for Isoprenoid Biosynthesis," *Journal of Bacteriology* 183(24):7403-7407.

Oulmouden et al. (1991), "Nucleotide Sequence of the *ERG12* Gene of *Saccharomyces cerevisiae* Encoding Mevalonate Kinase," *Current Genetics* 19:9-14.

Polakowski et al. (1998), "Overexpression of a Cytosolic Hydroxymethylglutaryl-CoA Reductase Leads to Squalene Accumulation in Yeast," *Appl. Microbiol. Biotechnol.* 49:66-71.

Rohdich et al. (2002), "Studies on the Nonmevalonate Terpene Biosynthetic Pathway: Metabolic Role of IspH (LytB) Protein," *PNAS* 99(3):1158-1163.

Rohlin et al. (2001), "Microbioal Pathway Engineering for Industrial Processes: Evolution, Combinatorial Biosynthesis and Rational Design," *Current Opinion in Microbiology* 4:330-335.

Rohmer et al. (1993), "Isoprenoid Biosynthesis in Bacteria: A Novel Pathway for the Early Steps Leading to Isopentenyl Diphosphate," *Biochem. J.* 295:517-524.

Sandmann (2001), "Carotenoid Biosynthesis and Biotechnological Application," *Archives of Biochemistry and Biophysics* 385(1):4-12.

Szkopinska et al. (2000), "The Regulation of Activity of Main Mevalonic Acid Pathway Enzymes: Farnesyl Diphosphate Synthase, 3-Hydroxy-3-Methylglutaryl-CoA Reductase, and Squalene Synthase in Yeast *Saccharomyces cerevidiae*," *Biochemical and Biophysical Research Communications* 267:473-477.

Takagi et al. (2000), "A Gene Cluster for the Mevalonate Pathway from *Streptomyces* sp. Strain CL190," *Journal of Bacteriology* 182(15):4153-4157.

Toth et al. (1996), "Molecular Cloning and Expression of the cDNAs Encoding Human and Yeast Mevalonate Pyrophosphate Decarboxylase," *The Journal of Biological Chemistry* 271(14)7895-7898.

Tsay et al. (1991), "Cloning and Characterization of *ERG8*, an Essential Gene of *Saccharomyces cervisiae* that Encodes Phosphomevalonate Kinase," *Molecular and Cellular Biology* 11(2):620-631.

Wang et al. (1999), "Engineered Isoprenoid Pathway Enhances Astaxanthin Production in *Escherichia coli*," *Biotechnology and Bioengineering* 62(2):235-241.

Wang et al. (2000), "Directed Evolution of Matabolically Engineered *Escherichia coli* for Carotenoid Production," *Biotechnol. Prog.* 16(6):922-926.

National Science Foundation Award Abstract No. 9911463.

\* cited by examiner

BIOSYNTHESIS OF AMORPHA-4,11-DIENE

CROSS-REFERENCE TO RELATED APPLICATIONS

This is a continuation-in-part of U.S. patent application Ser. No. 10/006,909, filed on Dec. 6, 2001, the disclosure of which is incorporated by reference in its entirety.

TECHNICAL FIELD

The present invention relates to the biosynthesis of isopentenyl pyrophosphate (IPP) and isoprenoids derived therefrom. More particularly, the present invention relates to the biosynthesis of amorpha-4,11-diene using an optimized amorpha-4,11-diene synthase gene. Even more particularly, the invention relates to nucleic acid sequences, enzymes, expression vectors, and transformed host cells for carrying out the methods.

BACKGROUND

Isoprenoids are compounds derived from the five-carbon molecule, isopentenyl pyrophosphate. Investigators have identified over 29,000 individual isoprenoid compounds, with new ones continuously being discovered. Isoprenoids are often isolated from natural products, such as plants and microorganisms, which use isopentenyl pyrophosphate as a basic building block to form relatively complex structures. Vital to living organisms, isoprenoids serve to maintain cellular fluidity and electron transport, as well as function as natural pesticides, to name just a few of their roles in vivo. Furthermore, the pharmaceutical and chemical communities use isoprenoids as pharmaceuticals, nutriceuticals, flavoring agents, and agricultural pest control agents. Given their importance in biological systems and usefulness in a broad range of applications, isoprenoids have been the focus of much attention by scientists.

Terpenoids or terpenes, a class of isoprenoids, are a highly diverse class of natural products and are of particular interest since numerous commercial flavors, fragrances and medicines such as antimalarial and anticancer drugs, are derived from them. Of particular interest is amorpha-4,11-diene, the sesquiterpene olefin precursor to artemisinin, a valuable and powerful antimalarial natural product. Artemisinin and its derivatives are sesquiterpene lactones containing an endoperoxide bridge that is unique among the antimalarial drugs. Artemisinins have been acclaimed as the next generation of antimalarial drugs because they show little or no cross-resistance to existing antimalarials. However, artemisinin is but one example of a large group of terpene-based natural products that have found use in treating human disease (e.g., Taxol, a diterpene extracted from the Pacific Yew, is extremely effective in the treatment of certain cancers; and limonene, a monoterpene, and related derivatives are believed to inhibit farnesylation of the growth promoting protein RAS, and therefore inhibit malignant cell proliferation.

Conventional means for obtaining isoprenoids include extraction from biological materials (e.g., plants, microbes, and animals). In general, these drugs accumulate in very small amounts in these materials. Therefore, the commercial production of these drugs by extraction and purification from plant materials, for example, provide low yields. In addition, extraction of isoprenoids from biological materials may also require toxic solvents. Finally, isoprenoids typically require further derivatization prior to use, which can also affect the overall yield obtained. Therefore, even though many of the isoprenoids are most active when derivatized, the ability to produce the olefin backbone in large quantities in a genetically and metabolically tractable host will still result in less expensive drugs and derivatives that may be more active than the original natural product.

Furthermore, because of the complexity of these molecules, the chemical syntheses of terpenoids are inherently difficult, expensive and produce relatively low yields (See Danishefsky et al. (1996) *J. Amer. Chem. Soc.* 118:2843–2859; Nicolaou et al. (1997) *Angew. Chem. Int. Ed.* 36:2520–2524; and Avery et al. (1992) *J. Amer. Chem. Soc.* 114:974–979). For example, organic synthesis is usually complex since several steps are required to obtain the desired product. Furthermore, these steps often involve the use of toxic solvents, which require special handling and disposal.

Unfortunately, the difficulty involved in obtaining relatively large amounts of isoprenoids has limited their practical use. In fact, the lack of readily available methods by which to obtain certain isoprenoids has slowed down the progression of drug candidates through clinical trials. Furthermore, once an isoprenoid drug candidate has passed the usual regulatory scrutiny, the actual synthesis of the isoprenoid drug may not lend itself to a commercial scale.

Isoprenoids such as terpenoids are produced from the universal precursors isopentenyl pyrophosphate (IPP) and its isomer dimethylallyl pyrophosphate (DMAPP), which are synthesized by either of two biosynthetic pathways (FIG. 7). Eukaryotes, with the exception of plants, generally use the mevalonate-dependent (MEV) isoprenoid pathway to convert acetyl-CoA to IPP, which is subsequently isomerized to DMAPP. Plants employ both the MEV and the mevalonate-independent or deoxyxylulose-5-phosphate (DXP) pathways for isoprenoid synthesis. Prokaryotes, with some exceptions, employ the DXP pathway to produce IPP and DMAPP separately through a branch point (FIG. 7). See Rohdich et al. (2002) *Proc. Natl. Acad. Sci. USA* 99:1158–1163). IPP and DMAPP precursors are essential to *Escherichia coli* for the prenylation of tRNA's (Connolly et al. (1989) *J. Bacteriol.* 171:3233–3246) and the synthesis of farnesyl pyrophosphate (FPP), which is used for quinone and cell wall biosynthesis.

Based upon an understanding of these pathways, researchers have looked to biosynthetic production of isoprenoids. Some success has been obtained in the identification and cloning of the genes involved in isoprenoid biosynthesis. For example, U.S. Pat. No. 6,291,745 to Meyer et al. describes the production of limonene and other metabolites in plants. Although many of the genes involved in isoprenoid biosynthesis may be expressed in functional form in *E. coli* and other microorganisms, yields remain relatively low as a result of minimal amounts of precursors, namely isopentenyl pyrophosphate.

Croteau et al. describe in U.S. Pat. No. 6,190,895 the nucleic acid sequences that code for the expression of 1-deoxyxylulose-5-phosphate synthase, an enzyme used in one biological pathway for the synthesis of isopentenyl pyrophosphate. Low yields of isopentenyl pyrophosphate remain, however, since several more enzymes are needed to catalyze other steps in this isopentenyl pyrophosphate biosynthetic pathway. Further, the reference does not address an alternative pathway for isopentenyl pyrophosphate biosynthesis, namely the mevalonate pathway.

Several laboratories have described the engineering of the DXP pathway to increase the supply of isoprenoid precursors needed for high-level production of carotenoids in *E.* coli (Farmer et al. (2001) *Biotechnol. Prog.* 17:57–61; Kajiwara et al. (1997) *Biochem. J.* 324:421–426; and Kim et al. (2001) *Biotechnol. Bioeng.* 72:408–415). Balancing the pool of glyceraldehyde-3-phosphate and pyruvate or increasing the expression of 1-deoxy-D-xylulose-5-phosphate synthase (dxs), and IPP isomerase (idi) resulted in increased carotenoid build-up in the cell. Though improvements in isoprenoid production were noted, this approach most likely suffers from limitations by the internal control mechanisms that are present in the native host.

Research has also focused on the isolation of genes from *Artemisia annua* L. involved in artemisinin synthesis in the hope of lowering the cost of artemisinin production by improving the yields from genetically engineered plants (Mercke et al. (2000), *Arch. Biochem. Biophys.* 381:173–180; Bouwmeester et al. (1999) *Phytochem.* 52:843–854; Wallaart et al. (2001) *Planta* 212:460–465; and Chang et al. (2000) *Arch. Biochem. Biophys.* 383:178–184). The first gene discovered encoded the amorpha-4,11-diene synthase, which converts FPP to amorpha-4,11-diene.

Thus, the current invention is directed toward solving these and other disadvantages in the art by increasing the typically low yields associated with conventional synthesis of isopentenyl pyrophosphate, and isoprenoids. Specifically, the current invention is directed toward the engineered expression of a synthetic amorpha-4,11-diene synthase gene and the mevalonate isoprenoid pathway from *Saccharomyces cerevisiae* in *E. coli*. Since isopentenyl and dimethylallyl pyrophosphates are universal precursors to all isoprenoids, the strains of this invention can serve as platform hosts for the production of any terpenoid compound for which the biosynthetic synthase gene is available.

SUMMARY OF THE INVENTION

Accordingly, one aspect of the present invention relates to a method for synthesizing isopentenyl pyrophosphate in a host microorganism, comprising the step of introducing into the host microorganism a plurality of heterologous nucleic acid sequences, each coding for a different enzyme in the mevalonate pathway for producing isopentenyl pyrophosphate. Amorpha-4,11-diene is then synthesized by introducing into the host, a DNA fragment coding for an enzyme capable of converting isopentenyl pyrophosphate to dimethylallyl pyrophosphate, introducing into the host microorganism a DNA fragment coding for a farnesyl pyrophosphate synthase gene, and then introducing a DNA fragment coding for an optimized synthetic amorpha-4,11-diene synthase gene. Another aspect of the invention to provide such a method wherein the plurality of heterologous nucleic acid sequences is contained in at least one extrachromosomal expression vector.

Another aspect of the invention pertains to such a method wherein the plurality of heterologous nucleic acid sequences further comprises a DNA fragment coding for an enzyme capable of converting isopentenyl pyrophosphate to dimethylallyl pyrophosphate.

Yet another aspect of the invention to provide a method wherein the host microorganism is a prokaryote. Another aspect of the invention to provide a method wherein the prokaryote is *E. coli*.

Still another aspect of the invention to provide a method for synthesizing isopentenyl pyrophosphate in a host microorganism, wherein the method comprises introducing into the host microorganism an intermediate in the mevalonate pathway and at least one heterologous nucleic acid sequence, each said sequence coding for an enzyme in the mevalonate pathway necessary for converting the intermediate into isopentenyl pyrophosphate. Amorpha-4,11-diene is then synthesized by introducing into the host, a DNA fragment coding for an enzyme capable of converting isopentenyl pyrophosphate to dimethylallyl pyrophosphate, introducing into the host microorganism a DNA fragment coding for a farnesyl pyrophosphate synthase gene, and then introducing a DNA fragment coding for an optimized synthetic amorpha-4,11-diene synthase gene.

Another aspect of the invention to provide DNA fragments, expression vectors, and host cells for carrying out the methods described herein.

Additional embodiments, as well as advantages and features of the invention will be set forth in part in the description that follows, and in part will become apparent to those skilled in the art upon examination of the following, or may be learned through routine experimentation upon practice of the invention.

In one embodiment, the invention provides a method for synthesizing isopentenyl pyrophosphate (as well as GPP, FPP and GGPP) and amorpha-4,11-diene in a host microorganism. The method begins by introducing into a host microorganism a plurality of heterologous nucleic acid sequences, each coding for a different enzyme in the mevalonate pathway for producing isopentenyl pyrophosphate. As will be appreciated by those skilled in the art, the mevalonate pathway involves six enzymes. The pathway starts from acetyl-CoA, proceeds through the intermediate mevalonic acid, and results in isopentenyl pyrophosphate. A nucleotide sequence coding for an enzyme capable of converting isopentenyl pyrophosphate to dimethylallyl pyrophosphate can also be introduced. Additional nucleotide sequences coding for other genes are then introduced as well. For example, a nucleotide sequence coding for a farnesyl pyrophosphate synthase gene can be introduced into the host in order to direct products of the mevalonate pathway operons to the desired class of isoprenoids.

In one embodiment, a nucleotide sequence coding for an optimized synthetic amorpha-4,11-diene synthase gene can be introduced into the host in order to produce amorpha-4,11-diene. In another embodiment, a nucleotide sequence coding for an optimized synthetic epi-cedrol synthase gene can be introduced into the host to produce epi-cedrol.

In particular, nucleotide sequences coding for enzymes necessary in the production of specific isoprenoids may be introduced into the host microorganism, along with those coding for enzymes in the mevalonate pathway. Preferably, at least one extrachromosomal expression vector will be used to introduce the desired nucleic acid sequence(s), although more than one (e.g., two) different expression vectors may be used. In addition, the desired nucleic acid sequence(s) may be incorporated into the host microorganism's chromosomal material.

In another embodiment, the invention provides a method for synthesizing isopentenyl pyrophosphate in a host microorganism by introducing into the host microorganism an intermediate of the mevalonate pathway and one or more heterologous nucleic acid sequences. The introduced sequence or sequences each code for an enzyme in the mevalonate pathway necessary for converting the intermediate into isopentenyl pyrophosphate. Thus, for example, if mevalonate is the introduced intermediate, the method requires introduction of nucleic acid sequences that code for the enzymes necessary to convert mevalonate into isopentenyl pyrophosphate, for example, the introduction of nucleic acid sequences coding for an enzyme that phosphorylates mevalonate to mevalonate 5-phosphate, an enzyme that converts mevalonate 5-phosphate to mevalonate 5-pyrophosphate, and an enzyme that converts mevalonate 5-pyrophosphate to isopentenyl pyrophosphate. Of course, other intermediates in the mevalonate pathway, along with the necessary nucleic acid sequences, may be introduced as well. Amorpha-4,11-diene is then synthesized by introducing into the host, a DNA fragment coding for an enzyme capable of converting isopentenyl pyrophosphate to dimethylallyl pyrophosphate, introducing into the host microorganism a DNA fragment coding for a farnesyl pyrophosphate synthase gene, and then introducing a DNA fragment coding for an optimized synthetic amorpha-4,11-diene synthase gene.

Although any host microorganism, e.g., a prokaryote or eukaryote, may be employed, it is preferred that a prokaryote such as *E. coli* be used. Preferably, the host organism does not synthesize isopentenyl pyrophosphate through the mevalonate pathway, but rather through the deoxyxylulose-5 phosphate (DXP) pathway. In this way, side reactions involving the intermediates of the mevalonate pathway are minimized, thereby enhancing the yield and efficiency of the present methods.

In another embodiment of the invention, DNA fragments, each coding for an enzyme in the mevalonate pathway, are provided in one or more expression vectors. Thus, for the mevalonate pathway, the DNA fragments include those that code for enzymes capable of: (a) condensing two molecules of acetyl-CoA to acetoacetyl-CoA, preferably the nucleotide sequence of SEQ ID NO:1; (b) condensing acetoacetyl-CoA with acetyl-CoA to form HMG-CoA, preferably the nucleotide sequence of SEQ ID NO:2; (c) converting HMG-CoA to mevalonate, preferably the nucleotide sequence of SEQ ID NO:3; (d) phosphorylating mevalonate to mevalonate 5-phosphate, preferably the nucleotide sequence of SEQ ID NO:4; (e) converting mevalonate 5-phosphate to mevalonate 5-pyrophosphate, preferably the nucleotide sequence of SEQ ID NO:5; and (f) converting mevalonate 5-pyrophosphate to isopentenyl pyrophosphate, preferably the nucleotide sequence of SEQ ID NO:6.

In yet another embodiment, the invention provides expression vectors comprising the DNA fragments described above and elsewhere in the application, as well as host cells transformed with such expression vectors. The DNA fragments, expression vectors, and host cells transformed with the same expression vectors are useful in the present methods for synthesizing isopentenyl pyrophosphate, amorpha-4,11-diene, and epi-cedrol.

BRIEF DESCRIPTION OF THE DRAWINGS

For reference.

FIG. 8A shows amorpha-4,11-diene production by the synthetic amorpha-4,11-diene synthase, measured from *E. coli* DH10B (non-engineered DXP pathway) and *E. coli* DH10B harboring the pSOE4 plasmid (engineered DXP pathway, FIG. 7). FIG. 8B shows production from *E. coli* DH10B expressing the mevalonate bottom operon (pMBIS, FIG. 7) in cultures supplemented with increasing amounts of (±)-mevalonate. Since amorpha-4,11-diene is not available commercially, its concentrations are reported as equivalents of caryophyllene, another sesquiterpene olefin, using a standard curve and the relative abundance of ions 189 and 204 m/z of the two compounds.

Figure 11A:
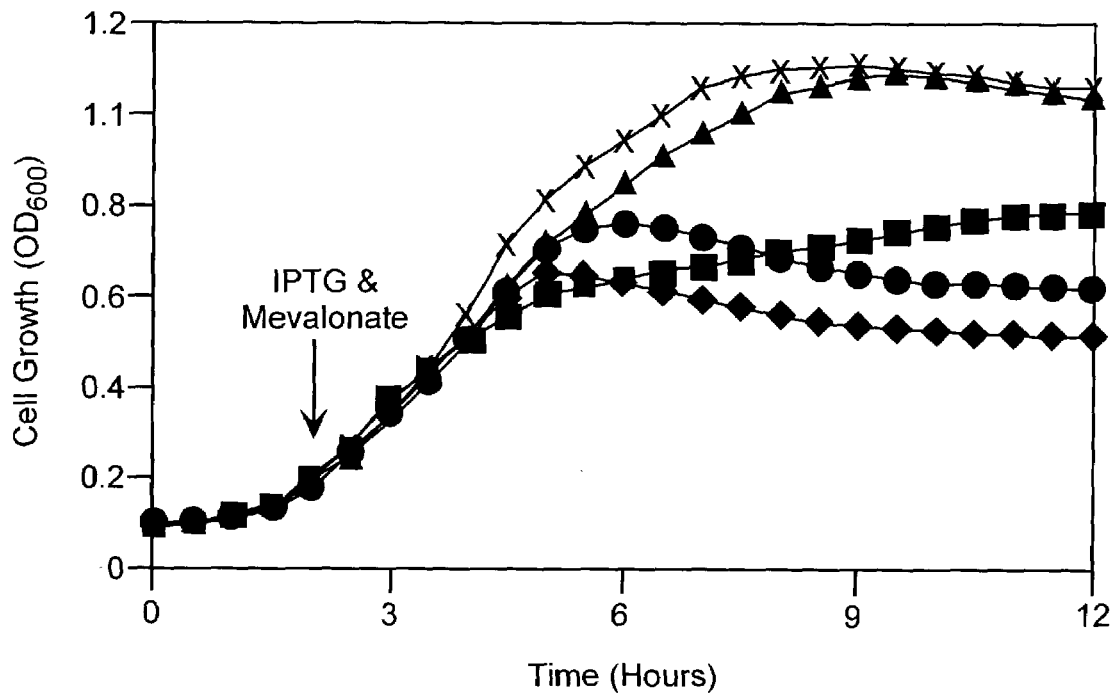
Figure 11B:
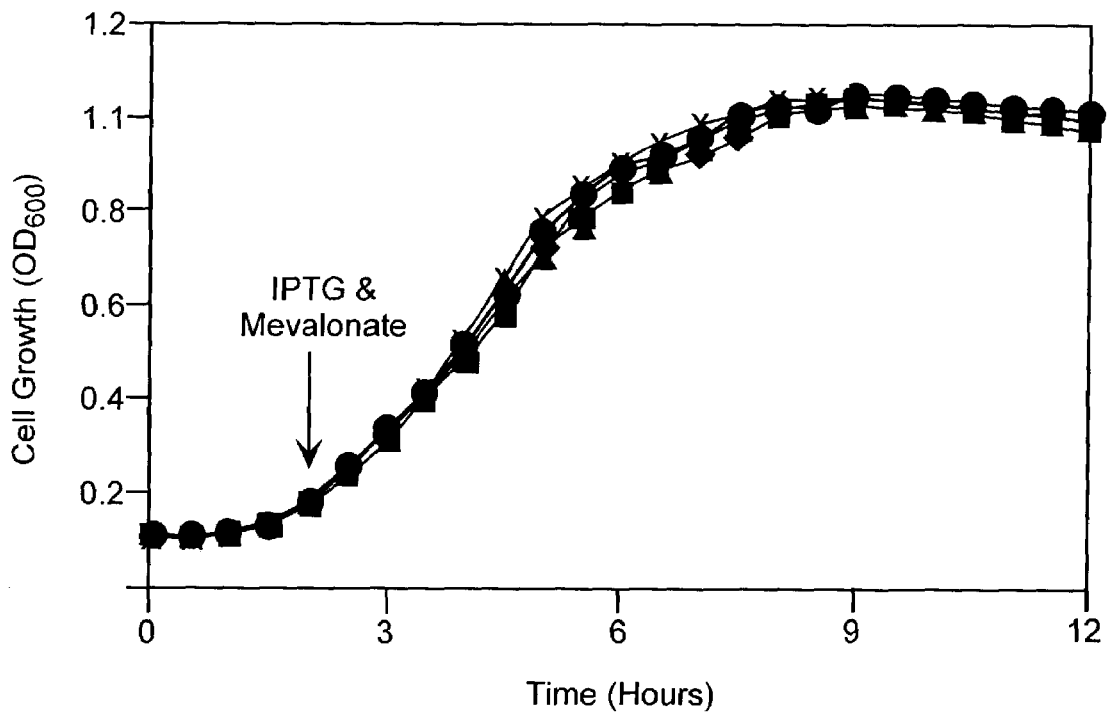

FIGS. 11A and 11B are graphs representing the effect of expression of the amorpha-4,11-diene synthase on the growth of *E. coli* harboring pMBIS and the empty expression vector pTrc99A (with ADS, FIG. 11A), and pADS expressing the amorpha-4,11-diene synthase (without ADS, FIG. 11B). LB medium was supplemented with 0 mM (x), 5 mM (solid triangle), 10 mM (solid square), 20 mM (solid diamond) or 40 mM (solid circle) of (±)-mevalonate.

Figure 12:
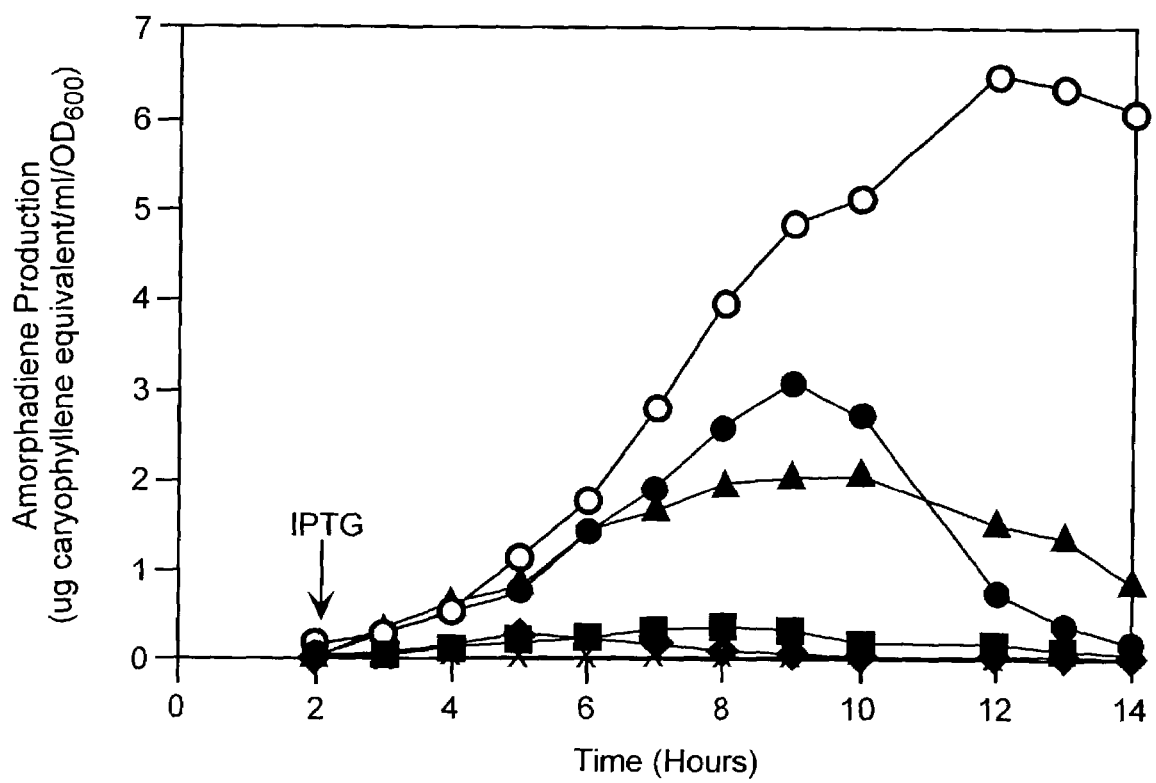

FIG. 12 is a comparison of the amorpha-4,11-diene production between *E. coli* expressing the native DXP pathway and the engineered isoprenoid pathways. The symbols represent amorpha-4,11-diene production from cells supplying FPP to synthase using the native DXP pathway (pLac33, pBBR1MCS-3, x); the engineered DXP pathway (pSOE4, pBBR1MCS-3, solid triangle); the mevalonate bottom pathway in the absence of (±)-mevalonate (pLac33, pMBIS, solid square); the mevalonate bottom pathway in medium supplemented with 30 mM (±)-mevalonate (pLac33, pMBIS, solid diamond); the complete mevalonate pathway (pMevT, pMBIS, solid circle) and the complete mevalonate pathway in medium supplemented with 0.8% glycerol (hollow circle).

DETAILED DESCRIPTION OF THE INVENTION

Figure 7:
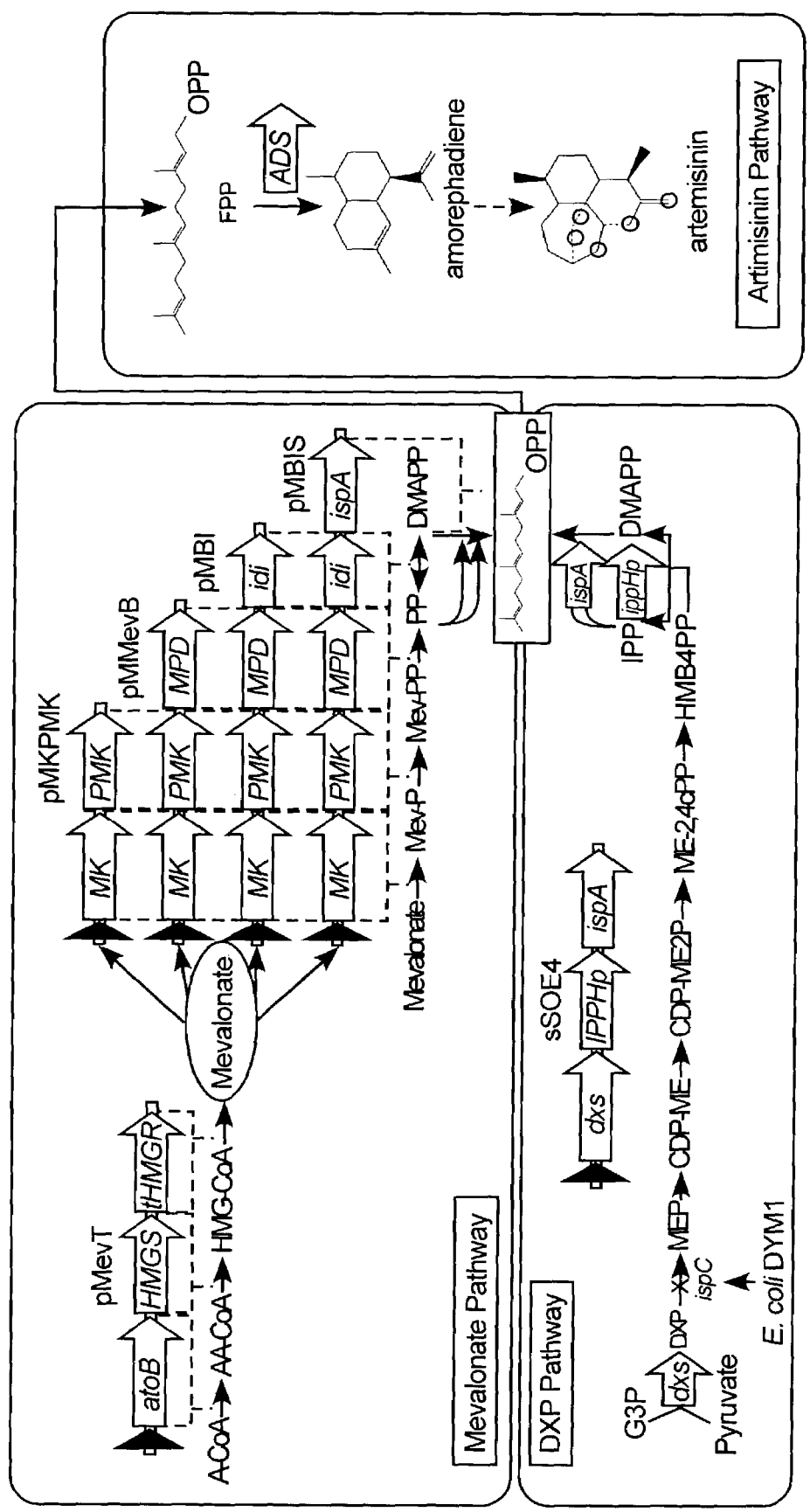
FIG. 7 schematically illustrates the production of amorpha-4,11-diene by the DXP or the mevalonate isoprenoid pathway and depiction of the synthetic operons used in the examples. The solid triangles represent the $P_{LAC}$ promoter and tHMGR refers to an N-terminal truncated product of the native HMGR gene. The abbreviations of the gene and pathway intermediates are as follows: atoB, acetoacetyl-CoA thiolase; HMGS, HMG-CoA synthase; tHMGR, truncated HMG-CoA reductase; MK, mevalonate kinase; PMK, phosphomevalonate kinase; MPD, mevalonate pyrophosphate decarboxylase; idi, IPP isomerase from *E. coli*; IPPHp, IPP isomerase from *Haematococcus pluvialis*; dxs, 1-deoxy-D-xylulose-5-phosphate synthase; ispC, 1-deoxy-D-xylulose-5-phosphate reductoisomerase; ispA, FPP synthase; ADS, amorpha-4,11-diene synthase; G3P, glyceraldehyde 3-phosphate; DXP, 1-deoxy-D-xylulose-5-phosphate; MEP, 2-C-methyl-D-erythritol 4-phosphate; CDP-ME, 4-diphosphocytidyl-2-C-methyl-D-erythritol; CDP-ME2P, 4-diphosphocytidyl-2-C-methyl-D-erythritol 2-phosphate; ME-2, 4cPP, 2C-methyl-D-erythritol 2,4-cyclopyrophosphate; HMB4PP, 1-hydroxy-2-methyl-2-(E)-butenyl 4-pyrophosphate; IPP, isopentenyl pyrophosphate; DMAPP, dimethylallyl pyrophosphate; FPP, farnesyl pyrophosphate; A-CoA, acetyl-CoA; AA-CoA acetoacetyl-CoA; HMG-CoA, hydroxymethylglutaryl-CoA; Mev-P, mevalonate-5-phosphate; Mev-PP, mevalonate pyrophosphate.

Isoprenoids are produced from the universal precursors isopentenyl pyrophosphate (IPP) and its isomer dimethylallyl pyrophosphate (DMAPP), which are synthesized by either of two biosynthetic pathways: the mevalonate-dependent (MEV) isoprenoid pathway or the mevalonate-independent or deoxyxylulose-5-phosphate (DXP) pathway (FIG. 7). Generally, eukaryotes use the MEV isoprenoid pathway, plants use both the MEV and the DXP pathways, and prokaryotes use the DXP pathway.

The DXP pathway may be tied to unknown physiological and control elements in *E. coli*. Therefore, this invention bypasses this pathway by engineering the expression of the *Saccharomyces cerevisiae* mevalonate-dependent pathway in *E. coli*. It was found that expression of this heterologous pathway in *E. coli* led to such an abundance of isoprenoid precursors that cells either ceased to grow or mutated to overcome the toxicity.

As described above, the first gene isolated from *Artemisia annua* L. encoded the amorpha-4,11-diene synthase. However, the production of sesquiterpenes using native plant genes has shown that poor expression of the plant genes in *E. coli* will restrict the terpene yields. Therefore, the instant invention is directed to expressing terpene synthase genes in a microbial host that is engineered to produce high levels of the IPP precursor, as well as GPP, FPP and GGPP, for enhanced yields of terpene olefins. The simultaneous expression of a synthetic amorpha-4,11-diene synthase gene (Mercke et al. (2000) *Arch. Biochem. Biophys.* 381:173–180) in the engineered strain of the invention, thus provides for high-level production of amorpha-4,11-diene, as well as alleviating growth inhibition.

The engineered expression of this synthetic amorpha-4, 11-diene synthase gene and the mevalonate isoprenoid pathway from *Saccharomyces cerevisiae* in *E. coli* is expected to be useful in providing platform host strains for the production of any terpenoid compound for which the biosynthetic synthase gene is available.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

In this specification and in the claims that follow, reference will be made to a number of terms that shall be defined to have the following meanings.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host microorganism" and "cell" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus. A preferred prokaryotic cell is *E. coli*. Preferred eukaryotic cells are those derived from fungal, insect, or mammalian cell lines.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochemistry* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In a first embodiment, the invention provides a method for synthesizing isopentenyl pyrophosphate, the fundamental building block of isoprenoids, in a host microorganism.

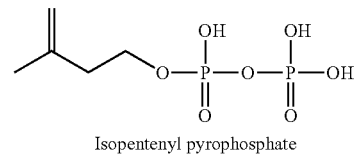

Isopentenyl pyrophosphate

Isopentenyl pyrophosphate is also known as "isopentenyl diphosphate" and is commonly abbreviated as "IPP." The method comprises introducing into the host microorganism a plurality of heterologous nucleic acid sequences each coding for a different enzyme in the mevalonate pathway for producing isopentenyl pyrophosphate. As stated previously, the mevalonate pathway for producing isopentenyl pyrophosphate in living organisms begins with acetyl-CoA and involves a mevalonate intermediate.

In another method for synthesizing isopentenyl pyrophosphate, an intermediate in the mevalonate pathway is introduced into the host microorganism. Although any method for introducing the intermediate may be used, it is preferred to add the intermediate to the culture medium used to grow the host microorganism. In this way, the intermediate is transported, e.g., via passive diffusion, across the cellular membrane and into the host microorganism.

Either before or after the intermediate is introduced, nucleic acid sequence(s) are introduced that code for those enzymes of the mevalonate pathway necessary to convert the intermediate into isopentenyl pyrophosphate. As will be appreciated by one of ordinary skill in the art, the conversion from the intermediate into isopentenyl pyrophosphate may require one, two, three, or more steps. Although any of the intermediates, i.e., acetyl Co-A, acetoacetyl-CoA, HMG-CoA, mevalonate, mevalonate 5-phosphate, and mevalonate 5-diphosphate, may be used, introduction of DL-mevalonate is a particularly preferred intermediate when using this method in the production of isopentenyl pyrophosphate. Enantiomers of any of the intermediates, such as the bioactive enantiomer D-mevalonate, may be used as well.

Figure 1A:
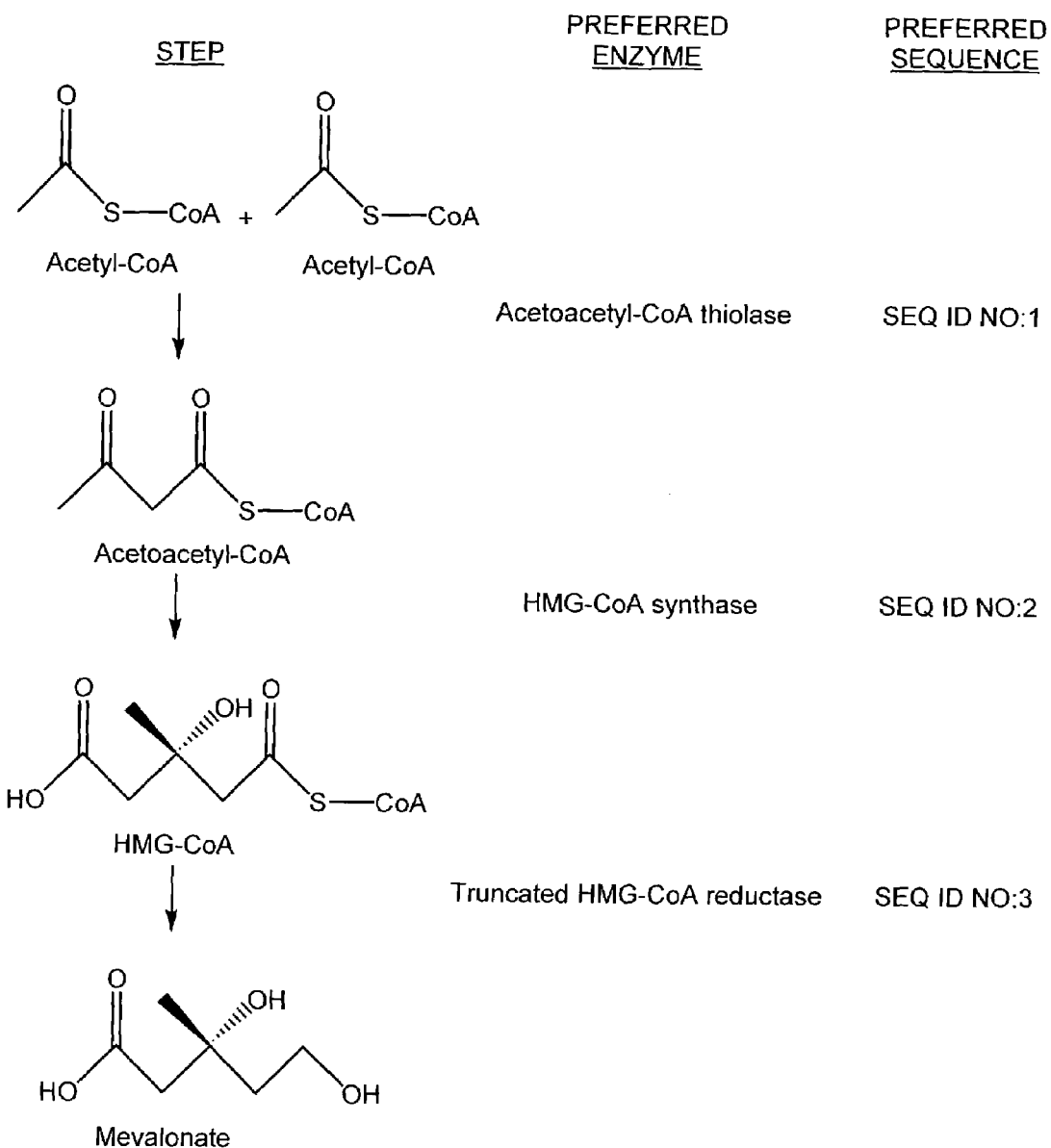
FIGS. 1A and 1B schematically illustrate the mevalonate pathway of isopentenyl pyrophosphate synthesis, along with preferred enzymes involved and nucleic acid sequences coding for such enzymes.
Figure 1B:
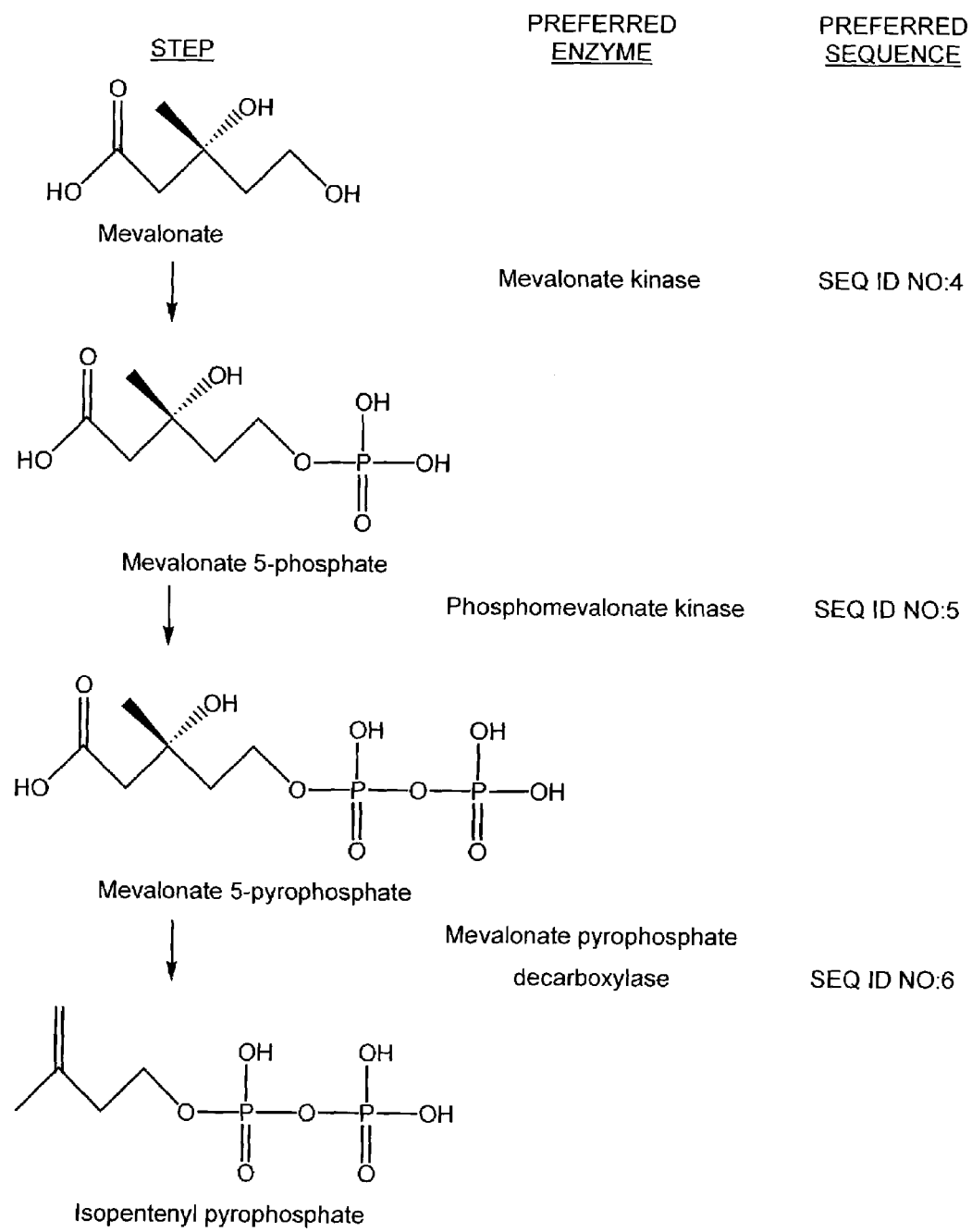

As shown in the schematic of FIGS. 1A and 1B, the mevalonate pathway comprises six steps and involves six intermediates. Initially, two molecules of acetyl-coenzyme A (more commonly referred to as "acetyl-CoA") are combined. Acetyl-CoA is produced naturally by the host microorganism when it is in the presence of a suitable carbon source. For example, eukaryotic cells naturally synthesize acetyl-CoA from compounds derived from sugars and fats. An enzyme capable of condensing two molecules of acetyl-CoA to acetoacetyl-CoA is used in this first step of synthesizing isopentenyl pyrophosphate via the mevalonate pathway.

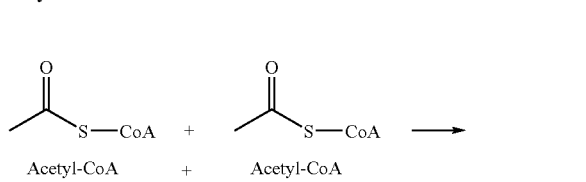

Acetyl-CoA + Acetyl-CoA →

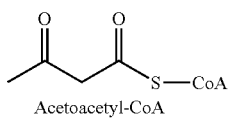
Acetoacetyl-CoA

Thus, any DNA fragment coding for an enzyme capable of carrying out this step may be used in the present method. Preferably, however, the DNA fragment codes for an acetoacetyl-CoA thiolase. Genes for such thiolases are known to those of ordinary skill in the art and include, for example, the genes of acetyl-CoA thiolase from *Ralstonia eutrophus* (Peoples et al. (1989) *J. Biol. Chem.* 264(26): 5293–15297); *Saccharomyces cerevisiae* (*S. cerevisiae*) (Hiser et al. (1994) *J. Biol. Chem.* 269(50): 31383–31389); and *E. coli*. It is particularly preferred, however, that the thiolase encoded by the nucleotide sequence of SEQ ID NO:1 be used in the present method.

The next step in the mevalonate pathway requires the condensation of acetoacetyl-CoA, formed from the preceding step, with yet another molecule of acetyl-CoA to form 3-hydroxy-3-methylglutaryl-CoA (HMG-CoA). This step is catalyzed enzymatically using an enzyme that will condense acetoacetyl-CoA with acetyl-CoA.

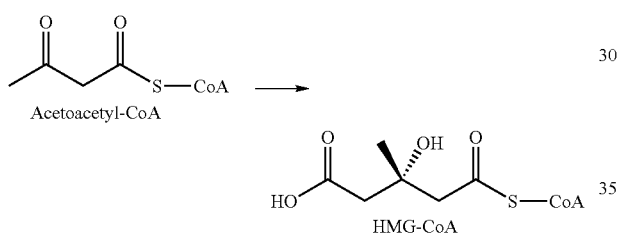

Although any DNA fragment that codes for an enzyme capable of carrying out this step may be used, it is preferred that the DNA fragment code for an HMG-CoA synthase. Known genes for HMG-CoA synthases include, without limitation, the synthases from *Blattella germanica* (Martinez-Gonzalez et al. (1993) *Eur. J. Biochem.* 217(2):691–699); and *S. cerevisiae*, and thus, are preferred. A particularly preferred synthase is encoded by the nucleotide sequence of SEQ ID NO:2.

The third step converts HMG-CoA to mevalonate. As with the other steps, this conversion is enzymatically controlled.

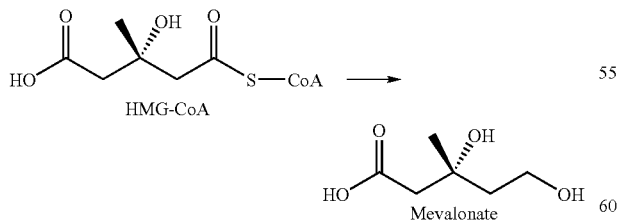

According to the present method, a DNA fragment coding for an enzyme that is capable of converting HMG-CoA into mevalonate is included in the expression vector. The HMG-CoA reductase genes from *Sulfolobus solfataricus* (Bochar (1997) *J. Bacteriol.* 179(11):3632–3638); *Haloferax volcanii* (Bischoff et al. (1996) *J. Bacteriol.* 178(1):19–23); and *S. cerevisiae* (Basson et al. (1988) *Mol Cell Biol.* 8(9): 3797–808) are known, and are consequently preferred for the present methods. It is particularly preferred, however, that the nucleotide sequence of SEQ ID NO:3 that encodes an HMG-CoA reductase be used in the present methods.

The nucleotide sequence defined by SEQ ID NO:3 that encodes an HMG-CoA reductase is a truncated version of the *S. cerevisiae* gene coding for HMG-CoA reductase, HMG1. The protein coded for by HMG1 is an integral membrane protein located in the endoplasmic reticulum of *S. cerevisiae*; it consists of a membrane-spanning, regulatory domain in its N-terminal region (amino acids 1–552) and a catalytically active domain in its C-terminal region. (See Polakowski (1998) *Appl. Microbiol Biotechnol.* 49:66–71) The nucleotide sequence defined by SEQ ID NO:3 comprises an artificial start codon, followed by nucleotides 1660–3165 of the HMG1 sequence. Therefore, the nucleotide sequence defined by SEQ ID NO:3 codes for only the catalytically active portion of *S. cervisiae* HMG-CoA reductase.

The fourth step in the mevalonate pathway involves the enzymatic phosphorylation of mevalonate to form mevalonate 5-phosphate.

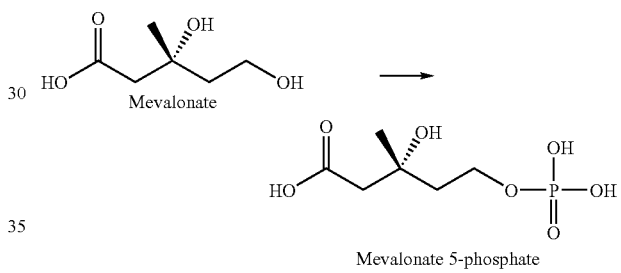

Although any DNA fragment coding for an enzyme capable of mevalonate phosphorylation may be used, it is preferred that a DNA fragment coding specifically for mevalonate kinase be used. Genes for such kinases are known to those of ordinary skill in the art and include, for example, the mevalonate kinase of *S. cerevisiae* (Oulmouden et al. (1991), *Curr. Genet.* 19(1): 9–14). A particularly preferred sequence that codes for this particular kinase is identified in SEQ ID NO:4.

The fifth step in the mevalonate pathway requires the addition of a second phosphate group to mevalonate 5-phosphate. An enzyme catalyzes this step.

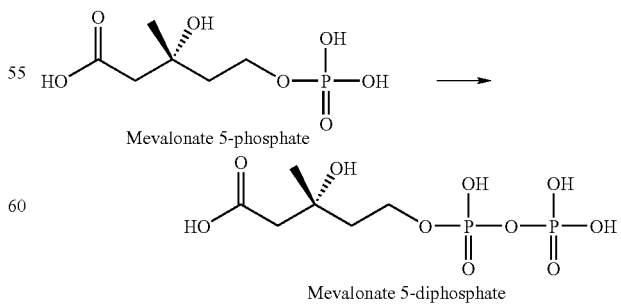

In the present method, a DNA fragment that codes for an enzyme capable of adding a second phosphate group to mevalonate 5-phosphate is used in the expression vector. Preferably, the DNA fragment codes for a phosphomevalonate kinase, such as the gene of the same name obtained from *S. cerevisiae* (Tsay et al. (1991) *Mol. Cell. Biol.* 11(2):620–31). Such kinases are known to those of ordinary skill in the art and include, for example, the kinase coded by the nucleotide sequence of SEQ ID NO:5.

The sixth and final step of the mevalonate pathway is the enzymatic conversion of mevalonate 5-pyrophosphate into isopentenyl pyrophosphate.

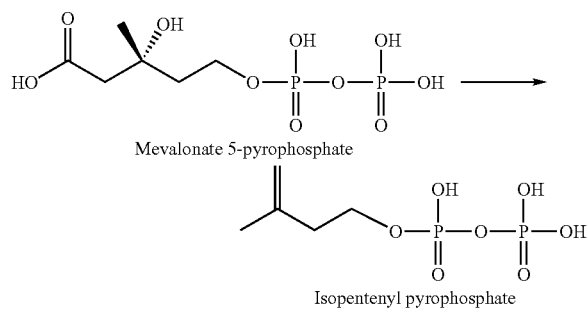

Although any DNA fragment coding for a mevalonate pyrophosphate decarboxylase may be used, it is particularly preferred that the gene from *S. cerevisiae* (Toth et al. (1996) *J. Biol. Chem.* 271(14):7895–7898) be used. A particularly preferred DNA fragment is the nucleotide sequence of SEQ ID NO:6.

When an intermediate is introduced, the method additionally requires introduction of DNA fragments that code for enzymes responsible for catalyzing those steps of the mevalonate pathway located "downstream" from the introduced intermediate. With reference to the mevalonate pathway described above and to the biosynthetic schemes provided in FIGS. 1A and 1B, one of ordinary skill in the art can readily determine which DNA fragments and enzymatic steps are necessary when a given intermediate is introduced into the host microorganism.

The mevalonate pathway is contrasted with the mevalonate-independent (or deoxyxylulose-5-phosphate) pathway. In some organisms, isopentenyl pyrophosphate production proceeds by condensation of pyruvate and glyceraldehyde-3-phosphate, via 1-deoxyxylulose-5-phosphate (DXP) as an intermediate. (See Rohmer et al. (1993) *Biochem. J.* 295:517–524.) While some organisms have genes for only one pathway, other organisms have genes for both pathways. For a discussion of both the mevalonate and deoxyxylulose 5-phosphate pathways, reference is made to Lange et al. (2000) *Proc. Natl. Acad. Sci. USA* 97(24): 13172–13177.

Amorpha-4,11-diene is then synthesized by introducing into the host, a DNA fragment coding for an enzyme capable of converting isopentenyl pyrophosphate to dimethylallyl pyrophosphate, introducing into the host microorganism a DNA fragment coding for a farnesyl pyrophosphate synthase gene, and then introducing a DNA fragment coding for an optimized synthetic amorpha-4,11-diene synthase gene. A particularly preferred DNA fragment that codes for a farnesyl pyrophosphate synthase gene is the nucleotide sequence of SEQ ID NO:11. A particularly preferred DNA fragment that codes for an optimized synthetic amorpha-4,11-diene synthase gene is the nucleotide sequence of SEQ ID NO:37.

Epi-cedrol can also be synthesized in a similar manner, except that a DNA fragment coding for an optimized synthetic epi-cedrol synthase gene is introduced in the final step. A particularly preferred DNA fragment that codes for an optimized synthetic epi-cedrol synthase gene is the nucleotide sequence of SEQ ID NO:39.

Any prokaryotic or eukaryotic host microorganism may be used in the present method so long as it remains viable after being transformed with a sequence of nucleic acids. Generally, although not necessarily, the host microorganism is bacterial. Examples of bacterial host microorganisms include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus* taxonomical classes. Preferably, the host microorganism is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host microorganism's own metabolic processes and those processes involved with the mevalonate pathway.

Those of ordinary skill in the art can readily identify suitable host microorganisms. For example, cross-talk is minimized or eliminated entirely when the host microorganism relies exclusively on the "deoxyxylulose 5-phosphate" (or "DXP") pathway for synthesizing isopentenyl pyrophosphate. In such host microorganisms, the mevalonate pathway does not inherently influence (save for the additional synthesis of isopentenyl pyrophosphate) the host microorganism, since it lacks any genes that are equipped to process the proteins (i.e., enzymes) or intermediates associated with the mevalonate pathway. Such organisms relying exclusively or predominately on the deoxyxylulose 5-phosphate pathway include, for example, *E. coli*. Of course, it will be recognized by those of ordinary skill in the art that the host microorganism used in the method may also conduct isopentenyl pyrophosphate synthesis via the mevalonate pathway, either exclusively or in combination with the deoxyxylulose 5-phosphate pathway.

Sequences of nucleic acids coding for the desired enzymes of the mevalonate pathway are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in D. M. Matteuci et al. (1980) *Tet. Lett.* 521:719; U.S. Pat. No. 4,500,707 to Caruthers et al.; and U.S. Pat. Nos. 5,436,327 and 5,700,637 to Southern et al.). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions. (See, for example, U.S. Pat. No. 4,683,195 to Mullis.)

Once each of the individual nucleic acid sequences necessary for carrying out the desired steps of the mevalonate pathway has been determined, as well as those sequences needed to produce the desired isoprenoid, each sequence must be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art. (See, for example, U.S. Pat. No. 4,683,195 to Minshull et al.)

For example, each of the desired nucleic acid sequences can be initially generated in a separate polymerase chain reaction (PCR). Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3–9 nucleotides in length and located 3–11 nucleotides upstream of the initiation codon in *Escherchia coli*. See Shine et al. (1975) *Nature* 254:34 and Steitz, in *Biological Regulation and Development: Gene Expression* (ed. R. F. Goldberger), vol. 1, p. 349, 1979, Plenum Publishing, N.Y., for discussions of ribosome binding sites in *E. coli*.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example includes the tac promoter. (See deBoer et al. (1983) *Proc. Natl. Acad. Sci. U.S.A.* 80:21–25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage; as well as mutant phages, such as λgt-λβ. Of course, such expression vectors may only be suitable for a particular host microorganism. One of ordinary skill in the art, however, can readily determine through routine experimentation whether any particular expression vector is suited for any given host microorganism. For example, the expression vector can be introduced into the host organism, which is then monitored for viability and expression of the sequences contained in the vector. In addition, reference may be made to the relevant texts and literature, which describe expression vectors and their suitability to any particular host microorganism.

The expression vectors of the invention must be introduced or transferred into the host microorganism. Such methods for transferring the expression vectors into host microorganisms are well known to those of ordinary skill in the art. For example, one method for transforming *Escherichia coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequence(s) provides the ability to transfect host microorganisms. Other means, such as lipid complexes, liposomes, and dendrimers, may also be employed. Those of ordinary skill in the art can transfect a host microorganism with a desired sequence using these or other methods.

For identifying a transfected host microorganism, a variety of methods are available. For example, a culture of potentially transfected host microorganisms may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host microorganism is transformed with at least one expression vector. When only a single expression vector is used (without the addition of an intermediate), the vector will contain all of the nucleic acid sequences necessary for carrying out isopentenyl pyrophosphate synthesis via the mevalonate pathway. Although such an all-encompassing expression vector may be used when an intermediate is introduced, only those nucleic acid sequence(s) necessary for converting the intermediate to isopentenyl pyrophosphate are required.

When two versions of an expression vector are used (without the addition of an intermediate), nucleic acid sequences coding for some of the six proteins (i.e., enzymes) necessary for isopentenyl synthesis via the mevalonate pathway, as well as the sequences needed to produce the desired isoprenoid, may be contained in a first expression vector, while the remainder are contained in a second expression vector. Again, the nucleic acid sequence(s) necessary for converting an introduced intermediate into isopentenyl pyrophosphate will be contained in the expression vector(s). As will be appreciated by those of ordinary skill in the art, a number of different arrangements are possible, and the invention is not limited with respect to the particular arrangement used.

Once the host microorganism has been transformed with the expression vector, the host microorganism is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, the starting material necessary for isopentenyl pyrophosphate production in the mevalonate pathway, is ensured. When added, the intermediate is present in an excess amount in the culture medium.

As the host microorganism grows and/or multiplies, expression of the proteins (i.e., enzymes) necessary for carrying out the mevalonate pathway, or for carrying out one or more steps within the pathway, is effected. Once expressed, the enzymes catalyze the steps necessary for carrying out the steps of the mevalonate pathway, i.e., converting acetyl-CoA into isopentenyl pyrophosphate. If an intermediate has been introduced, the expressed enzymes catalyze those steps necessary to convert the intermediate into isopentenyl pyrophosphate. Any means for recovering the isopentenyl pyrophosphate from the host microorganism may be used. For example, the host microorganism may be harvested and subjected to hypotonic conditions, thereby lysing the cells. The lysate may then be centrifuged and the supernatant subjected to high performance liquid chromatography (HPLC). Once the isopentenyl pyrophosphate is recovered, modification may be carried out in the laboratory to synthesize the desired isoprenoid.

If desired, the isopentenyl pyrophosphate may be left in the host microorganism for further processing into the desired isoprenoid in vivo, e.g., for the production of amorpha-4,11-diene or epi-cedrol. For example, large amounts of the isoprenoid lycopene are produced in *E. coli* specially engineered with the expression vector pAC-LYC, as shown in Examples 3 and 4. Lycopene can be recovered using any art-known means, such as those discussed above with respect to recovering isopentenyl pyrophosphate. Lycopene is an antioxidant abundant in red tomatoes and may protect males from prostate cancer. (See Stahl et al. (1996) *Ach. Biochem. Biophys.* 336(1):1–9.) Of course, many other isoprenoids can be synthesized through other pathways, and the invention is not limited with respect to the particular "downstream" pathway. Thus, the present method not only provides methods for producing isopentenyl pyrophosphate, but offers methods for producing isoprenoids as well, with amorpha-4,11-diene and epi-cedrol being particularly described herein.

When isopentenyl pyrophosphate is retained in the host microorganism for further biochemical processing, it is preferred that the heterologous nucleic acid sequences introduced into the host microorganism also include a DNA fragment coding for an enzyme capable of converting isopentenyl pyrophosphate to dimethylallyl pyrophosphate. As appreciated by those of ordinary skill in the art, a suitable isomerase will catalyze the conversion of isopentenyl pyrophosphate into dimethylallyl pyrophosphate. Such isomerases are known to those of ordinary skill and include, for example, the isopentenyl pyrophosphate isomerase (idi) coded by the nucleotide sequence of SEQ ID NO:10. Isoprenoid biosynthetic pathways require dimethylallyl pyrophosphate, and increased expression of the isomerase ensures that the conversion of isopentenyl diphoshate into dimethylallyl pyrophosphate does not represent a rate-limiting step in the overall pathway.

The present methods thus provide for the biosynthetic production of isopentenyl pyrophosphate and the isoprenoids amorpha-4,11-diene and epi-cedrol derived therefrom. As stated above, isopentenyl pyrophosphate has been available only in relatively small amounts, and the present methods provide a means for producing relatively large amounts of this important compound.

Further, the invention provides the ability to synthesize increased amounts of isoprenoids. As stated above, isoprenoids represent an important class of compounds and include, for example, food and feed supplements, flavor and odor compounds, and anticancer, antimalarial, antifungal, and antibacterial compounds. Preferred isoprenoids are those selected from the group consisting of monoterpenes, sesquiterpenes, diterpenes, sesterterpenes, triterpenes, tetraterpenes, and steroids. As a class, terpenes are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged terpenes.

Monoterpenes include, for example, flavors such as limonene, fragrances such as citranellol, and compounds having anticancer activity, such as geraniol. Sesquiterpenes include, without limitation: periplanone B, a cockroach hormone used to lure cockroaches into traps; artemisinin, an antimalarial drug; ginkgolide B, a platelet-activating factor antagonist; forskolin, an inhibitor of adenylate cyclase; and farnesol, a compound shown to have anticancer activity. Nonlimiting examples of diterpenes include the antibacterial and antifungal compound casbene and the drug paclitaxel. Among triterpenes ($C_{30}$) and tetraterpenes ($C_{40}$) are carotenoids, which are used as antioxidants, coloring agents in food and cosmetics, and nutritional supplements (e.g., as vitamin A precursors). As pathways to these and other isoprenoids are already known, the invention can advantageously be incorporated into an overall scheme for producing relatively large amounts of a desired isoprenoid.

It is known that the microbial production of plant sesquiterpenes in *E. coli* provides for poor expression of the synthase genes, thus limiting high terpene olefin yields from this host (Martin et al. (2001) *Biotechnol. Bioeng.* 75:497–503). To circumvent this limitation, the invention is directed to the synthesis of an amorpha-4,11-diene synthase gene from oligonucleotides using the *E. coli* codon preferences, which can greatly improve gene expression (Hale et al. (1998) *Protein Exper. Purif.* 12:185–188).

Comparison of sesquiterpene production between *E. coli* expressing the native sesquiterpene synthase genes and the synthetic ADS gene of the invention indicated a significant 10- to 300-fold improvement in terpene synthesis.

Accordingly, in one embodiment of this invention, a codon-optimized amorpha-4,11-diene synthase (ADS) gene (SEQ ID NO:37), designed for high-level expression in *E. coli.*, was synthesized and expressed. By the expression of this codon-optimized synthase, the limitations of microbial terpene synthesis are expected to shift from the expression of the synthase gene to the supply of the precursor by the isoprenoid pathway. The gene synthesis, which used a two-step assembly and one-step amplification PCR reactions, yielded the expected 1.7 kb product (Example 6, section b). Sequence analysis of three ADS genes from independent clones identified two mutations or more in each of the genes. A functional ADS gene was assembled together from two clones and two site-directed mutagenesis reactions.

The use of microbes as platform hosts for the synthesis of isoprenoids offers several advantages over existing methods since they are better suited for the engineering enzymes and biochemical pathways. For example, the amorpha-4,11-diene gene described herein may be easily replaced with any terpene synthase for high-level production of the new terpene. Furthermore, in vitro evolution and combinatorial biosynthesis of sesquiterpene biochemical pathways in microbes may lead to artemisinin derivatives or even new sesquiterpene lead compounds.

Insufficient supply of the prenyl pyrophosphate precursor by the native DXP pathway has been known to limit carotenoid and taxadiene yields in *E. coli*. Metabolic engineering of the DXP pathway has been previously shown to increase the flux as measured by 2- to 40-fold increases in carotenoid accumulation over incubation periods of 20 to 50 hours. Likewise, in this study a 3-fold increase in sesquiterpene accumulation after 5 hours was observed using a similar engineering strategy (FIG. 12). These observations may infer that this approach to engineering the DXP pathway results in only a modest increase in flux, which may only be detectable using carotenoid biosynthesis as a reporter and long incubation periods. In this invention, the mevalonate isoprenoid pathway is shown to be a superior biosynthetic route to deliver high-level isoprenoid precursors to terpene synthases for large-scale production. By engineering the *S. cerevisiae* mevalonate-dependent isoprenoid pathway into *E. coli*, the mevalonate pathway's native regulatory elements found in yeast have been circumvented while bypassing those of *E. coli*'s native DXP pathway. In fact, the heterologous pathway leads to such a vast excess of prenyl pyrophosphates that cell growth was inhibited. Co-expression of a synthetic sesquiterpene synthase consumes the excess pool of precursor thereby eliminating growth inhibition and providing high yields of amorpha-4,11-diene. Although total biosynthesis of artemisinin was not achieved in this study, the engineered biochemical pathway could readily be extended to produce artemisinic acid. Artemisinic acid can then converted in high yields (40%) to artemisinin or one of the derivatives via a photooxidation cyclization reaction (Jung et al. (1990) *Planta Med.* 56:624).

Epi-cedrol synthase is involved in plant synthesis of epi-cedrol, which is believed to be an insecticide. Accordingly, in one embodiment of this invention, a codon-optimized epi-cedrol synthase gene (SEQ ID NO:40), designed for high-level expression in *E. coli.*, was synthesized and expressed. The amino acid sequence is also provided (SEQ ID NO:39).

Conveniently, the invention also provides sequences, enzymes, expression vectors, and host cells or microorganisms for carrying out the present methods. For example, the six genes necessary for isopentenyl pyrophosphate synthesis from acetyl-CoA are conveniently provided in SEQ ID NO:7. SEQ ID NO:7 has a $P_{BAD}$ promoter and the strong ribosomal terminators start at nucleotide 8828. The isopentenyl pyrophosphate isomerase (idi) gene (SEQ ID NO:10) corresponds to nucleotide sequence 97–645 of SEQ ID NO:7. The acetoacetyl-CoA thiolase gene (SEQ ID NO:1) corresponds to nucleotide sequence 684–1868 of SEQ ID NO:7. The HMG-CoA synthase gene (SEQ ID NO:2) corresponds to nucleotide sequence 1882–3357 of SEQ ID NO:7. The truncated HMG-CoA reductase gene (SEQ ID NO:3) corresponds to nucleotide sequence 3371–4879 of SEQ ID NO:7. The mevalonate kinase gene (SEQ ID NO:4) corresponds to nucleotide sequence 4907–6238 of SEQ ID NO:7. The phosphomevalonate kinase gene (SEQ ID NO:5) corresponds to nucleotide sequence 6251–7606 of SEQ ID NO:7. The mevalonate pyrophosphate decarboxylase gene (SEQ ID NO:6) corresponds to nucleotide sequence 7619–8809 of SEQ ID NO:7.

In addition, the invention also provides sequences for the first three genes and the last three genes in SEQ ID NO:8 and SEQ ID NO:9, respectively. SEQ ID NO:8 has a $P_{BAD}$ promoter and the strong ribosomal terminators start at nucleotide 4335. The acetoacetyl-CoA thiolase gene (SEQ ID NO:1) corresponds to nucleotide sequence 115–1299 of SEQ ID NO:8. The HMG-CoA synthase gene (SEQ ID NO:2) corresponds to nucleotide sequence 1313–2788 of SEQ ID NO:8. The truncated HMG-CoA reductase gene (SEQ ID NO:3) corresponds to nucleotide sequence 2802–4310 of SEQ ID NO:8. SEQ ID NO:9 has a Lac promoter. The mevalonate kinase gene (SEQ ID NO:4) corresponds to nucleotide sequence 254–1585 of SEQ ID NO:9. The phosphomevalonate kinase gene (SEQ ID NO:5) corresponds to nucleotide sequence 1598–2953 of SEQ ID NO:9. The mevalonate pyrophosphate decarboxylase gene (SEQ ID NO:6) corresponds to nucleotide sequence 2966–4156 of SEQ ID NO:9.

Finally, the invention also provides sequences for the last three genes in SEQ ID NO:12 and SEQ ID NO:13. SEQ ID NO:12 has a Lac promoter. The mevalonate kinase gene (SEQ ID NO:4) corresponds to nucleotide sequence 254–1585 of SEQ ID NO:12. The phosphomevalonate kinase gene (SEQ ID NO:5) corresponds to nucleotide sequence 1598–2953 of SEQ ID NO:12. The mevalonate pyrophosphate decarboxylase gene (SEQ ID NO:6) corresponds to nucleotide sequence 2966–4156 of SEQ ID NO:12. The isopentenyl pyrophosphate decarboxylase gene corresponds to nucleotide sequence 4183–4731 of SEQ ID NO:12. SEQ ID NO:13 has a Lac promoter. The mevalonate kinase gene (SEQ ID NO:4) corresponds to nucleotide sequence 254–1585 of SEQ ID NO:13. The phosphomevalonate kinase gene (SEQ ID NO:5) corresponds to nucleotide sequence 1598–2953 of SEQ ID NO:13. The mevalonate pyrophosphate decarboxylase gene (SEQ ID NO:6) corresponds to nucleotide sequence 2966–4156 of SEQ ID NO:13. The isopentenyl pyrophosphate isomerase (idi) gene (SEQ ID NO:10) corresponds to nucleotide sequence 4183–4731 of SEQ ID NO:13. The farnesyl pyrophosphate synthase (ispA) gene (SEQ ID NO:11) corresponds to nucleotide sequence 4786–5685 of SEQ ID NO:13.

All the aforementioned sequences can easily be included in an expression vector using techniques described herein or other techniques well known to those of ordinary skill in the art. In addition, the invention also provides host cells transformed with one or more of these expression vectors for use in carrying out the present methods.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

Experimental

The practice of the present invention will employ, unless otherwise indicated, conventional techniques of the biosynthetic industry and the like, which are within the skill of the art. Such techniques are explained fully in the literature.

In the following examples, efforts have been made to ensure accuracy with respect to numbers used (e.g., amounts, temperature, etc.), but some experimental error and deviation should be accounted for. Unless indicated otherwise, temperature is in degrees Celsius and pressure is at or near atmospheric pressure at sea level. All reagents, unless otherwise indicated, were obtained commercially.

EXAMPLE 1

Cloning of the Mevalonate Pathway Operons a) Assembly of the Mevalonate Operons

Individual genes for a mevalonate-isoprenoid pathway were assembled to form artificial complete and at least one functional operon. Cloning of the nucleic acid sequences coding for the enzymes of the mevalonate pathway was carried out and the reproduced sequences were divided into two operons. In one of the two operons, the last three genes of the biosynthetic pathway (mevalonate kinase (MK), SEQ ID NO:4; phosphomevalonate kinase (PMK, SEQ ID NO:5; and mevalonate pyrophosphate decarboxylase (MPD, SEQ ID NO:6) were cloned by a polymerase chain reaction (PCR) as one operon by splicing the genes together using overlap extensions (SOEing). This operon is referred to as the mevalonate bottom (MevB) operon (SEQ ID NO:9). In the second of the two operons, the first three genes of the pathway (acetoacetyl-CoA thiolase (atoB, SEQ ID NO:1; HMG-CoA synthase (HMGS, SEQ ID NO:2; and a truncated version of HMG-CoA reductase (tHMGR, SEQ ID NO:3) were cloned as a separate artificial operon using the same technique. This operon is referred to as the mevalonate top (MevT) operon (SEQ ID NO:8). The individual genes were isolated by PCR from genomic DNA of *Saccharomyces cerevisiae* and *E. coli* prepared by established microbiologic protocols. (See Sambrook et al., *Molecular Cloning: a Laboratory Manual*, $3^{rd}$ ed., Cold Harbor Springs Laboratory Press.) The 100 µL PCR reactions contained 1×Pfu buffer, 1.5 mM MgSO$_4$ (Stratagene, La Jolla, Calif.), 200 µM of each dNTP (Gibco BRL™, Life Technologies, Inc., Gaithersburg, Md.), 500 µM of each primer, 100 to 500 ng of template DNA, 5% dimethyl sulfoxide (Sigma, St. Louis, Mo.), and 2.5 U of Pfu Turbo DNA polymerase (Stratagene). The reactions were carried out in a PTC-200 Peltier Thermal Cycler from MJ Research (South San Francisco, Calif.) with the following temperature cycling program: an initial heating step up to 95° C. for four minutes was followed by 30 cycles of 30 seconds of denaturing at 95° C., 30 seconds of annealing at 50° C., and 100 seconds of extension at 72° C., followed by one cycle at 72° C. for ten minutes. Once each gene of the operon was amplified from genomic DNA preparations, the operons were assembled by PCR reactions similar to the procedure described above, but using the amplified DNA of all three genes as template DNA and only the forward primer of the outermost 5' gene and the reverse primer of the outermost 3' gene. The assembled operons were isolated on 0.7% agarose gels and purified using a Qiagen gel purification kit (Valencia, Calif.) according to the manufacturer's instructions.

b) Cloning Mevalonate Operons into Sequencing and Expression Vectors

As expression of biochemical pathways is often suboptimal from high-copy plasmids containing strong promoters, the artificial mevalonate operon(s) were cloned in a variety of expression vectors to determine the effect of plasmid copy number and promoter strength on expression of the cloned pathway. Prior to testing for pathway expression, the assembled operons were cloned into the pCR4 TOPO vector using the Invitrogen TOPO TA cloning system (Carlsbad, Calif.) for sequencing purposes. Ligation into pCR4 TOPO vector and transformation of *E. coli* TOP10 cells were carried out according to the manufacturer's instructions. The synthetic operons were excised from the sequenced pCR4 TOPO vectors using restriction enzymes and ligated into the high-copy vector pBAD24, which contains the arabinose-inducible araBAD promoter (Guzman et al. (1995) *J. Bacteriology* 177:4121–4130); pTrc99A, which contains the IPTG-inducible tac promoter (Amann et al. (1988) *Gene* 69:301–315); or into pBBR1MCS-3 (Kovach et al. (1995) *Gene* 166:175–176) or pUC19 (Yanisch-Perron et al. (1985) *Gene* 33:103–119), which contain the unregulated Lac promoters (no plasmid-encoded LacI). The MevB operon was digested with PstI and ligated using T4 DNA ligase (New England Biolabs, Inc., Beverly, Mass.) into the PstI site of the low-copy vector, pBBR1MCS-3, containing $P_{Lac}$ promoter and tetracycline resistance marker. The resulting plasmid, which encodes the enzymes responsible for the conversion of mevalonate to isopentenyl pyrophosphate, was named pBBRMevB. The MevT operon was cloned into the SalI site of pBAD24 by digesting with SalI restriction enzyme and ligating with T4 DNA ligase. The resulting plasmid, which encodes the enzymes responsible for the conversion of acetyl-CoA to mevalonate, was named pBAD-MevT.

c) Addition of Isopentenyl Pyrophosphate Isomerase to MevB Operon

The syntheses of geranyl pyrophosphate (GPP), farnesyl pyrophosphate (FPP), and geranylgeranyl pyrophosphate (GGPP) require both isopentenyl pyrophosphate (IPP) and its isomer, dimethylallyl pyrophosphate (DMAPP), to create the backbone structure of all isoprenoids. To ensure sufficient production of DMAPP from IPP, an additional gene, idi (encoding isopentenyl pyrophosphate isomerase, SEQ ID NO:10), was amplified by PCR from *E. coli* genomic DNA using primers containing an XmaI restriction enzyme site at the 5' ends. Both the amplified product (containing idi) and pBBRMevB were digested with XmaI and ligated, thereby placing idi at the 3' end of the MevB artificial operon. The resulting operon, containing the MevB operon and idi, is designated MBI (SEQ ID NO:12). The resulting plasmid (containing the operon of genes that encode for enzymes that convert mevalonate to IPP and DMAPP) was named pBBRMBI-2.

d) Addition of Polyprenyl Pyrophosphate Synthase(s) to MBI Operon

In order to direct products of the mevalonate pathway operons to the different classes of isoprenoids (monoterpenes, sesquiterpenes, diterpenes, etc.), various polyprenyl pyrophosphate synthases were cloned into the MBI operon, such as geranyl diphosposphate (GPP) synthase, farnesyl pyrophosphate (FPP) synthase, and geranylgeranyl pyrophosphate (GGPP) synthase. Polyprenyl pyrophosphate synthases were cloned by PCR using forward primers with a SacII restriction site and reverse primers with a SacI restriction site. Using restriction enzymes and T4 DNA ligase, the polyprenyl pyrophosphate synthases were cloned between the SacII and SacI sites of pBBRMBI-2. For example, farnesyl pyrophosphate synthase gene ispA (SEQ ID NO:11) was isolated by PCR from *E. coli* genomic DNA and cloned between the SacII and SacI sites of pBBRMBI-2, 3' of idi and the MevB operon. The resulting operon, containing the MevB operon, idi, and ispA (SEQ ID NO:11) has been designated MBIS (SEQ ID NO:13). The plasmid, which encodes the enzymes responsible for the synthesis of farnesyl pyrophosphate (FPP) from mevalonate, was named pBBRMBIS-2.

EXAMPLE 2

Functionality of the Engineered Mevalonate Operon(s) by Growth/No-Growth Phenotype Functionality of the various genetic constructs was shown by expression of the artificial mevalonate-isoprenoid pathway. The plasmids were introduced into an *E. coli* host in which the mevalonate-independent (DXP) isoprenoid pathway was inactivated. *E. coli* strain DMY1 (Kuzuyama et al. (1999) *Biosci. Biotechnol. Biochem.* 63:776–778) contains a mutation (insertion/deletion) in the gene encoding for 1-deoxyxylulose 5-phosphate reductoisomerase (or DXR, the second step of the DXP pathway) that causes inactivation of the mevalonate-independent pathway. Since this mutation is lethal to *E. coli*, the strain must be propagated in Luria-Bertoni (LB) medium (available from, for example, Sigma, St. Louis, Mo.) containing 0.5 mM of methylerithrytol (ME), the product of DXR; or it must have an alternate pathway for the production of isopentenyl pyrophosphate.

Cultures of *E. coli* strain DMY1 were made electrocompetent according to the method of Sambrook et al. (above) and transformed with pBBRMBI-2, or both pBBRMBI-2 and pBADMevT. Newly transformed DMY1 cells were first allowed to recover on LB agar plates overnight, and were supplemented with 0.5 mM ME and appropriate antibiotics at 37° C. prior to testing growth on media devoid of ME. DMY1 cells transformed with only pBBRMBI-2 were plated on LB agar devoid of ME, but supplemented with 1 mM DL-mevalonate prepared by incubating 1 volume of 2 M DL-mevalonic acid lactone (Sigma, St. Louis, Mo.) with 1.02 volumes of 2 M KOH at 37° C. for 30 minutes. DMY1 cells transformed with both pBBRMBI-2 and pBADMevT plasmids were plated on LB agar with antibiotics only (no ME or DL-mevalonate). All test plates were incubated for 48 hours at 37° C.

*E. coli* strain DMY1 cells containing pBBRMBI-2 were able to grow on LB agar plates with 1 mM DL-mevalonate, whereas *E. coli* DMY1 cells without the plasmid or with pBBR1MCS-3 (empty vector control) did not grow. The MBI operon successfully converted the supplemented mevalonate to isopentenyl pyrophosphate and dimethylallyl pyrophosphate, thereby complementing the dxr deletion.

*E. coli* strain DMY1 cells containing pBADMevT and pBBRMBI-2 were able to grow on LB agar plates not supplemented with DL-mevalonate, whereas *E. coli* DMY1 cells without either of the plasmids could not grow on LB agar alone. The expression of the MevT and MBI operons successfully converted acetyl-CoA to isopentenyl pyrophosphate and dimethylallyl pyrophosphate in vivo, thereby restoring growth to *E. coli* strain DMY1, in which the native DXP isoprenoid pathway is inactive.

EXAMPLE 3

Production of Carotenoids from Mevalonate Using the MBI Artificial Operon

The production of a carotenoid was used to demonstrate the benefits of expressing the artificial mevalonate-dependent IPP biosynthetic pathway over the native *E. coli* DXP-isoprenoid pathway. The increased productivity of the mevalonate-dependent isopentenyl pyrophosphate biosynthetic pathway encoded by the synthetic operons was assayed by coupling isopentenyl pyrophosphate production to the production of lycopene. This was accomplished by co-transforming *E. coli* with pAC-LYC, a low-copy broad-host plasmid that expresses the genes encoding the pathway for lycopene production from farnesyl pyrophosphate. The genes expressed from pAC-LYC are crtE (geranylgeranyl pyrophosphate synthase), crtB (phytoene synthase), and crtI (phytoene desaturase) from *Erwinia herbicola*, which were cloned into pACYC184 using methods similar to those described in Examples 1 and 2. *E. coli* naturally produces farnesyl pyrophosphate from two molecules of isopentenyl pyrophosphate and one molecule of dimethylallyl pyrophosphate through the enzyme farnesyl pyrophosphate synthase, ispA (SEQ ID NO:11). Alternatively, more flux can be directed from the mevalonate pathway to the lycopene pathway by including the *E. coli* gene encoding farnesyl pyrophosphate synthase into the artificial operon(s).

From previous experiments (not described herein), it was found that the production of isopentenyl pyrophosphate from the mevalonate pathway operons was greater in the *E. coli* strain DH10B than in the *E. coli* strain DMY1. In order to demonstrate isopentenyl pyrophosphate production from the mevalonate pathway only, the gene encoding 1-deoxyxylulose 5-phosphate reductoisomerase, dxr, was inactivated in *E. coli* strain DH10B by the method detailed by Datsenko et al. (2000) *PNAS* 97:6640–6645. In the resulting *E. coli* strain, named DPDXR1, the mevalonate independent pathway (or DXP pathway) is inactive, and in order to survive, the strain must either be propagated in LB medium containing 0.5 mM of methylerithrytol (ME) or have an alternate pathway for the production of isopentenyl pyrophosphate.

Figure 2:
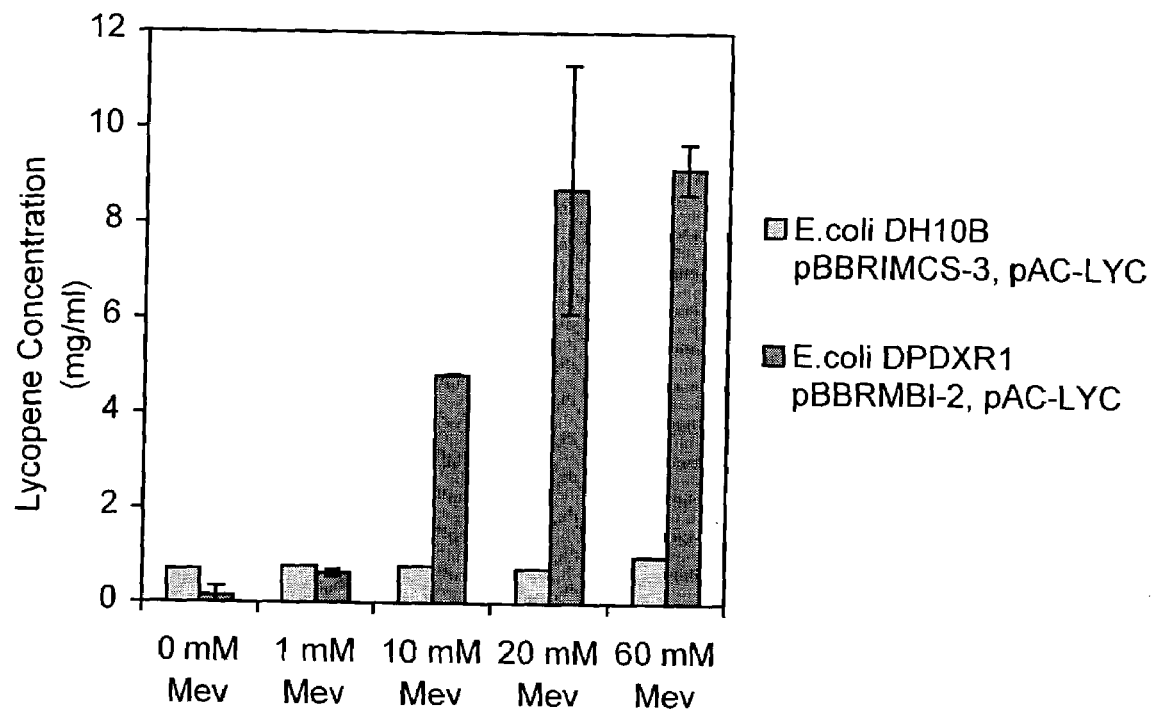
FIG. 2 is a graph illustrating the difference in the concentration of lycopene produced from natural levels of isopentenyl pyrophosphate in non-engineered *E. coli* and from *E. coli* engineered to overproduce isopentenyl pyrophosphate from a partial mevalonate-isoprenoid pathway, at different concentrations of mevalonate (Mev).

*E. coli* strain DPDXR1 was transformed with pAC-LYC and pBBRMBI-2, while *E. coli* strain DH10B was transformed with pAC-LYC and pBBR1MCS-3 (control) by electroporation. Transformants were selected on LB agar plates supplemented with 50 µg/ml chloramphenicol, 10 µg/ml tetracycline, and 1 mM DL-mevalonate by incubating overnight at 37° C. One colony of each strain (*E. coli* DPDXR1 harboring pAC-LYC and pBBRMBI-2 or *E. coli* DH10B harboring pAC-LYC and pBBR1MCS-3) was transferred from the LB agar selection plate to 5 ml of LB liquid medium also supplemented with 50 µg/ml chloramphenicol, 10 µg/ml tetracycline, and 1 mM DL-mevalonate. These seed cultures were incubated at 37° C. until they reached a stationary growth phase. The cell density of each seed culture was determined by measuring the optical density of the culture at a wavelength of 600 nm ($OD_{600}$). These seed cultures were then used to inoculate 5 ml test cultures of LB medium with appropriate antibiotics and increasing concentrations of DL-mevalonate. The volume of seed culture used to inoculate each fresh 5 ml culture was calculated to give an initial $OD_{600}$ value of 0.03. Test cultures were incubated for 48 hours at 30° C., after which growth was arrested by chilling the cultures on ice. The optical density of each culture was measured. One ml of each culture was harvested by centrifugation (25000×g, 30 seconds), the supernatant was removed, and cell pellets were suspended in 500 μL of acetone by rapid mixing with a Fisher Vortex Genie 2™ mixer (Scientific Industries, Inc., Bohemia, N.Y.). The acetone/cell mixtures were incubated at 55° C. for 10 minutes to aid in the extraction of lycopene from the cells. Extracted samples were centrifuged (25000×g, 7 minutes) to remove cell debris, and the cleared acetone supernatants were transferred to fresh tubes. The lycopene concentration of each acetone extraction was assayed by absorbance at 470 nm using a Beckman™ DU640 Spectrophotometer (Beckman Coulter, Inc., Fullerton, Calif.) and a 400 μL quartz cuvette. Absorbance values at 470 nm were converted to lycopene concentrations using linear regressions from a standard curve produced using pure lycopene (Sigma, St. Louis, Mo.). Final lycopene concentrations of each strain at increasing concentration of substrate is reported in FIG. 2. As shown in FIG. 2, lycopene production as a function of substrate concentration following shaking for 48 hours at 30° C. demonstrated that lycopene produced from natural levels of isopentenyl pyrophosphate in non-engineered *E. coli* strain DH10B (vertical stripes) remains relatively constant, while lycopene produced from isopentenyl pyrophosphate generated by engineered *E. coli* strain DPDXR1 harboring the plasmid, pBBRMBI-2 (horizontal stripes), significantly increases at mevalonate substrate concentrations of 10 mM and higher.

EXAMPLE 4

Production of Carotenoids from Luria-Bertoni Broth Using the Complete Mevalonate Pathway It was demonstrated that significantly higher levels of isopentenyl pyrophosphate and isoprenoids derived therefrom were produced using the complete mevalonate-isoprenoid operon when compared to the native DXP pathway. The complete mevalonate-isoprenoid pathway was expressed using the two operons, MevT and MBI, which were expressed from pBADMevT and pBBRMBI-2, respectively, and coupled to pAC-LYC to demonstrate the in vivo production of the carotenoid lycopene, using precursors produced by primary cellular metabolism.

Figure 3:
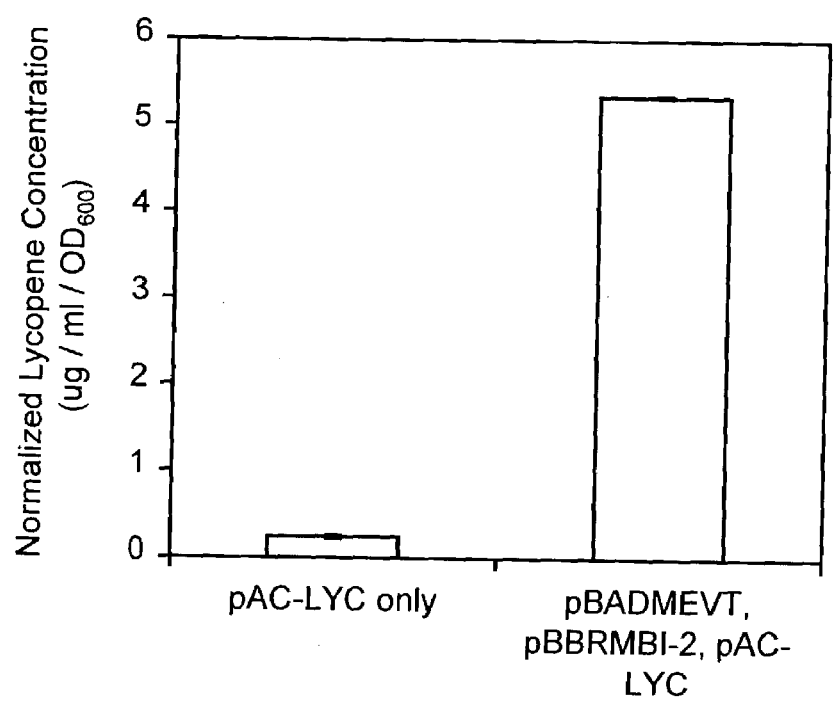
FIG. 3 is a graph illustrating the difference in normalized lycopene concentration produced from natural levels of isopentenyl pyrophosphate in non-engineered *E. coli* and from *E. coli* engineered to overproduce isopentenyl pyrophosphate from the complete mevalonate-isoprenoid pathway.

*E. coli* strain DH10B was transformed with pBADMevT, pBBRMBI-2, and pAC-LYC by electroporation. Transformants were selected on LB agar plates containing 50 μg/ml carbenicillin, 10 μg/ml tetracycline, and 50 μg/ml chloramphenicol. A single colony of the strain was transferred from the LB agar plate to 5 ml of LB liquid medium containing the same antibiotics. This seed culture was incubated by shaking at 37° C. until growth reached a stationary phase. The cell density of each seed culture was measured at $OD_{600}$, and the cells were used to inoculate 5 ml test cultures of fresh LB medium plus the same antibiotics to give an $OD_{600}$ of 0.03. The test cultures were incubated for 48 hours at 30° C., after which growth was arrested by chilling the cultures on ice. The remainder of the experimental procedure was followed as described in Example 3. Final lycopene production (μg/ml lycopene per $OD_{600}$) of the pBAD-MevT, pBBRMBI-2, pAC-LYC plasmid system was compared to the lycopene production from pAC-LYC plasmid only (control) in the *E. coli* DH10B strain, as shown in FIG. 3. This figure illustrates, in graph form, the amount of lycopene produced for each strain, normalized for cell density, after shaking for 48 hours at 30° C. The column on the left represents the amount of lycopene produced naturally in a non-engineered *E. coli* strain (containing only pAC-LYC as a control). The column on the right represents the amount of lycopene produced from an *E. coli* strain engineered to overproduce isopentenyl pyrophosphate from the mevalonate-isprenoid pathway.

EXAMPLE 5

Production of Terpenes by Coupling of Artificial Mevalonate Operon(s) to Terpene Cyclases Many valuable natural products were produced from the isoprenoid biosynthetic pathways described herein. Depending on the desired isoprenoid, the described operon(s) were modified, and/or additional operons or other means for chemical synthesis were provided to produce the precursors for the various classes. The following experiments demonstrated the synthesis of sesquiterpenes using the farnesyl pyrophosphate synthase, ispA (SEQ ID NO:11), as well as the means by which other classes of isoprenoids, such as diterpenes, were synthesized by varying the synthase cloned into the operon(s) to create the desired precursor.

a) In Vivo Production of Sesquiterpenes

Amorpha-4,11-diene, a precursor to the antimalarial drug artemisinin, was produced from the co-expression of the mevalonate-isoprenoid pathway, along with a sesquiterpene cyclase-encoding amorpha-4,11-diene synthesis. The MBIS operon expressed from pBBRMBIS-2 was coupled with amorpha-4,11-diene synthase (ADS) for the in vivo production of the sesquiterpene amorpha-4,11-diene in *E. coli*.

A gene coding for amorpha-4,11-diene synthase (ADS) was constructed so that, upon translation, the amino acid sequence would be identical to that described by Merke et al. (2000) *Ach. Biochem. Biophys.* 381(2):173–180. The ADS gene contains recognition sequences 5' and 3' of the coding DNA corresponding to the restriction endonucleases NcoI and XmaI, respectively. The ADS gene was digested to completion with the restriction endonucleases, along with DNA for the plasmid pTrc99A. The 1644-bp gene fragment and the 4155-bp plasmid fragment were purified using 0.7% agarose gels and a Qiagen gel purification kit (Valencia, Calif.) according to the manufacturer's instructions. The two fragments were then ligated using T4 DNA ligase from New England Biolabs (Beverly, Mass.), resulting in plasmid pTRCADS. The insert was verified by sequencing to be the amorpha-4,11-diene synthase gene.

*E. coli* strain DH10B was transformed with both the pBBRMBIS-2 and pTRCADS plasmids by electroporation. Bacterial colonies were then grown on Luria-Bertoni (LB) agar containing 50 μg/ml carbenicillin and 10 μg/ml tetracycline. A single bacterial colony was transferred from the agar plates to 5 ml LB liquid medium containing the same antibiotics and cultured by shaking at 37° C. for 16–18 hours. Five hundred μL of this culture was transferred into 5 ml fresh LB liquid medium with the same antibiotics, then cultured by shaking at 37° C. to an optical density of 0.816 at 600 nm ($OD_{600}$). A 1.6 ml portion of this culture was used to inoculate a flask containing 100 ml of LB liquid medium with 50 µg/ml carbenicillin and 10 µg/ml tetracycline, which was cultured by shaking at 37° C. After 1.5 hours, 1 ml of 1 M mevalonate and 100 µL of 500 mM isopropylthio-β-D-galactoside (IPTG) were added to the culture, and it continued to be shaken at 37° C. Amorpha-4,11-diene concentration was determined by extracting 700 µl samples (taken hourly) with 700 µl of ethyl acetate in glass vials. The samples were then shaken at maximum speed on a Fisher Vortex Genie 2™ mixer (Scientific Industries, Inc., Bohemia, N.Y.) for three minutes. The samples were allowed to settle in order to separate the ethyl acetate-water emulsions. Prior to gas chromatography-mass spectrometry analysis, the ethyl acetate layer was transferred with a glass Pasteur pipette to a clean glass vial.

Ethyl acetate culture extracts were analyzed on a Hewlett-Packard 6890 gas chromatograph/mass spectrometer (GC/MS). A 1 µl sample was separated on the GC using a DB-5 column (available from, for example, Agilent Technologies, Inc., Palo Alto, Calif.) and helium carrier gas. The oven cycle for each sample was 80° C. for two minutes, increasing temperature at 30° C./minute to a temperature of 160° C., increasing temperature at 3° C./min to 170° C., increasing temperature at 50° C./minute to 300° C., and a hold at 300° C. for two minutes. The resolved samples were analyzed by a Hewlett-Packard model 5973 mass selective detector that monitored ions 189 and 204 m/z. Previous mass spectra demonstrated that the amorpha-4,11-diene synthase product was amorpha-4,11-diene and that amorpha-4,11-diene had a retention time of 7.9 minutes using this GC protocol. Since pure standards of amorpha-4,11-diene are not available, the concentrations must be quantified in terms of caryophyllene equivalence. A standard curve for caryophyllene has been determined previously, based on a pure standard from Sigma (St. Louis, Mo.). The amorpha-4,11-diene concentration is based on the relative abundance of 189 and 204 m/z ions to the abundance of the total ions in the mass spectra of the two compounds.

Figure 4:
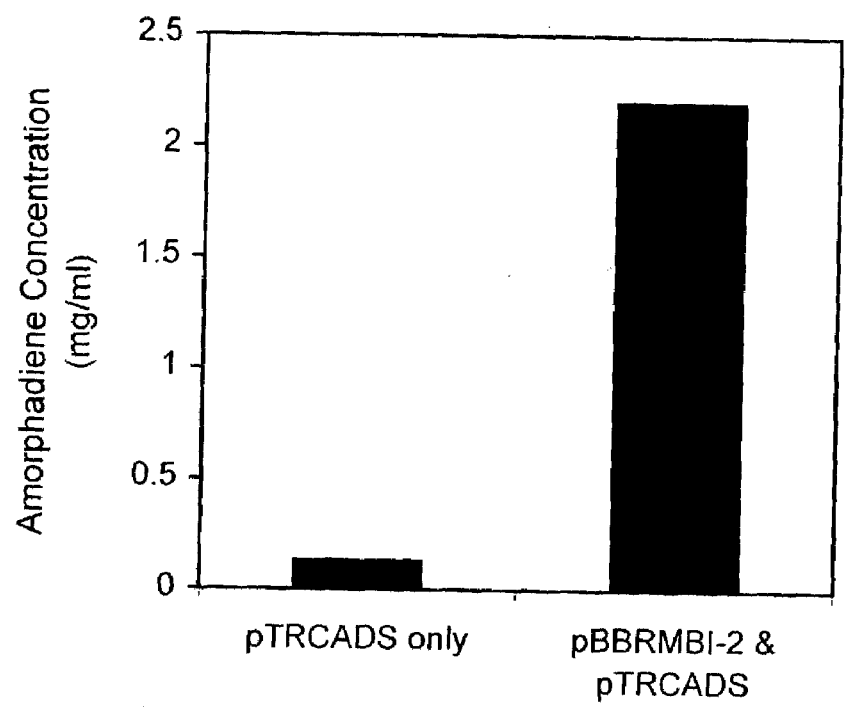
FIG. 4 is a graph illustrating the difference in amorpha-4,11-diene concentration produced from natural levels of isopentenyl pyrophosphate in non-engineered *E. coli* and from *E. coli* engineered to overproduce isopentenyl pyrophosphate from a partial mevalonate-isoprenoid pathway.

The amorpha-4,11-diene concentration of the cultures seven hours after the addition of IPTG and mevalonate is shown in FIG. 4. The figure shows the concentration of amorpha-4,11-diene produced seven hours after the addition of mevalonate and isopropylthio-β-D-galactoside (IPTG). The column on the left shows the concentration of amorpha-4,11-diene produced from non-engineered *E. coli* harboring the pTRCADS plasmid alone. The column on the right shows the concentration of amorpha-4,11-diene produced from engineered *E. coli* harboring the pBBRMBIS-2 and pTRCADS plasmids. The *E. coli* strain engineered to make farnesyl pyrophosphate from the mevalonate isoprenoid pathway produced 2.2 µg/ml amorpha-4,11-diene, whereas the non-engineered strain (without the mevalonate isoprenoid pathway) produced only 0.13 µg/ml.

b) In Vivo Production of Diterpenes

The plasmid pBBRMBIS-2 was modified to include a gene encoding geranylgeranyl pyrophosphate synthase (instead of farnesyl pyrophosphate synthase). To demonstrate the utility of the artificial mevalonate-isoprenoid for in vivo diterpene production, this modified expression system was coupled with a plasmid expressing casbene synthase. Casbene synthase cDNA cloned into expression vector pET21-d (Hill et al. (1996), *Arch Biochem. Biophys.* 336:283–289) was cut out with SalI (New England Biolabs, Beverly, Mass.) and NcoI (New England Biolabs, Beverly, Mass.) and re-cloned into high-copy-number expression vector pTrc99A. The gene fragment and the plasmid fragment were purified with 0.7% agarose gels using a Qiagen gel purification kit (Valencia, Calif.) according to the manufacturer's instructions. The two fragments were then ligated using T4 DNA ligase from New England Biolabs (Beverly, Mass.), resulting in plasmid pTrcCAS.

*E. coli* strain DH10B was transformed with both the modified pBBRMBIS-2 and pTrcCAS plasmids by electroporation. Bacterial colonies were then grown on Luria-Bertoni (LB) agar containing 50 µg/ml carbenicillin and 10 µg/ml tetracycline. A single bacterial colony was transferred from the agar plates to 5 ml LB liquid medium containing the same antibiotics and cultured by shaking at 37° C. for 16–18 hours. Five hundred microliters of this culture was transferred into 5 ml fresh LB liquid medium with 50 µg/ml carbenicillin and 10 µg/ml tetracycline, and cultured by shaking at 37° C. to an optical density of 0.816 at 600 nm ($OD_{600}$). A 150 µL portion of this culture was used to inoculate a flask containing 25 ml of LB liquid medium with 50 µg/ml carbenicillin, 10 µg/ml tetracycline, and 20 mM mevalonate. This mixture was cultured by shaking at 37° C. After 1.5 hours, 250 µL of 100 mM IPTG were added to the culture, and it continued to be shaken at 37° C. Casbene concentration of the culture was determined hourly by extracting 450 µl samples. To these samples was added 450 µL of ethyl acetate in a glass vial. The samples were then shaken on a Fisher Vortex Genie 2™ mixer (Scientific Industries, Inc., Bohemia, N.Y.) for three minutes. The samples were allowed to settle in order to separate the ethyl acetate-water emulsion. The ethyl acetate layer was transferred with a glass Pasteur pipette to a clean vial.

Figure 5:
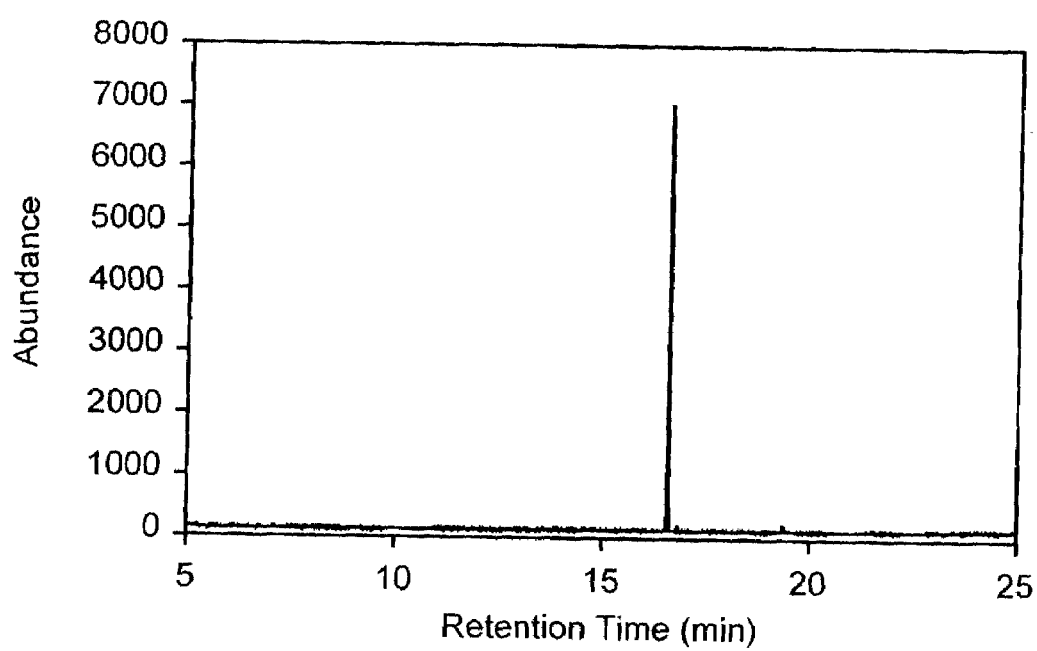
FIG. 5 is a gas chromatographic spectrum illustrating the production of diterpene using ethyl acetate extracts from *E. coli* engineered to produce isoprenoids from the artificial, modified MBIS operon (a partial mevalonate-isoprenoid pathway), and expressing a casbene cyclase.
Figure 6:
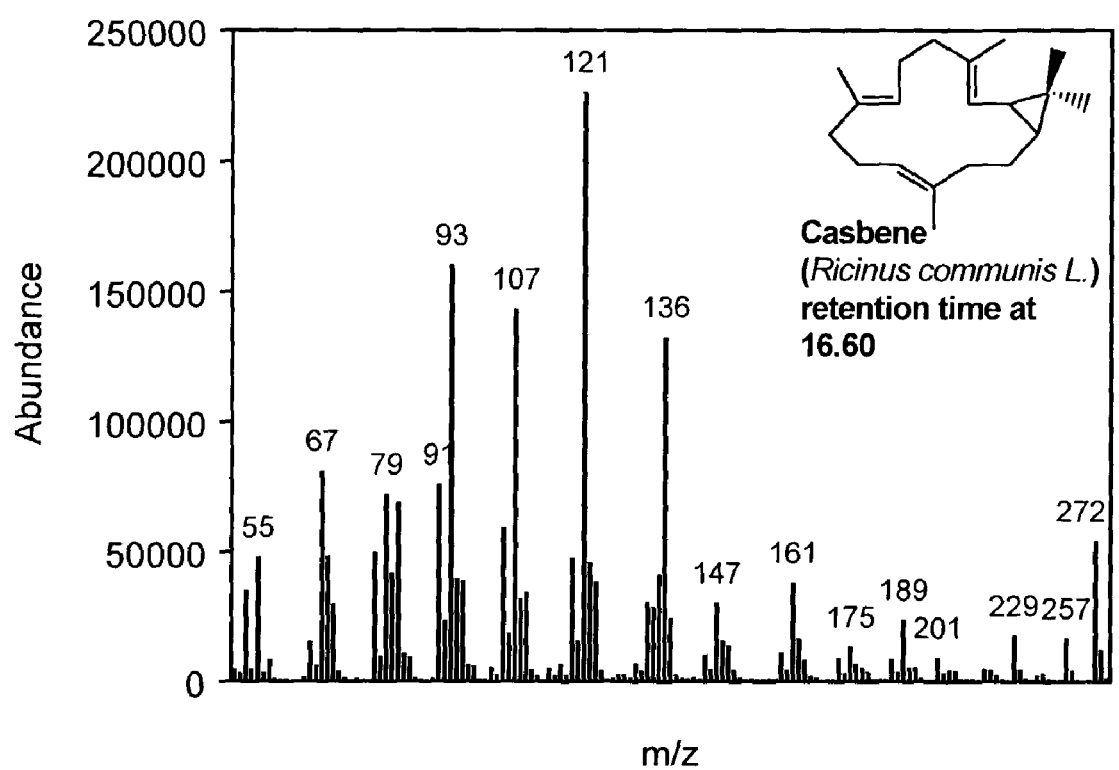
FIG. 6 is the mass spectrum of the isoprenoid casbene.

Ethyl acetate culture extracts were analyzed on a Hewlett-Packard 6890 gas chromatograph/mass spectrometer (GC/MS). A 1 µl sample was separated on the GC using a DB-5 column (available from, for example, Agilent Technologies, Inc., Palo Alto) and helium carrier gas. The oven cycle for each sample was 80° C. for two minutes, increasing temperature at 10° C./minute to a temperature of 300° C., and a hold at 300° C. for two minutes. The resolved samples were analyzed by a Hewlett-Packard model 5973 mass selective detector that monitored ions 229, 257, and 272 m/z. Previous mass spectra had demonstrated that the casbene synthase product was casbene and that casbene had a retention time of 16.6 minutes using this GC protocol. FIG. 5 shows the gas chromatographic analysis and resulting GC/MS chromatogram for the ethyl acetate extracts taken seven hours after addition of IPTG from *E. coli* engineered to produce isoprenoids from the artificial modified MBIS operon, thereby expressing the casbene cyclase from the pTrcCAS plasmid. As a reference, FIG. 6 shows the spectrogram for casbene.

EXAMPLE 6

Production of the Antimalarial Drug Precursor amorpha-4,11-diene Via an Engineered Mevalonate Pathway in *Escherichia coli*

To increase the intracellular concentration of FPP substrate supplied to the amorpha-4,11-diene synthase, the genes encoding the mevalonate-dependent isoprenoid pathway from *S. cerevisiae* were assembled into operons and expressed in *E. coli*. To simplify the task of engineering an eight-gene biosynthetic pathway, the genes were divided into two operons, referred to as the "top" and "bottom", as described in Example 1. The top operon, MevT, transforms the ubiquitous precursor acetyl-CoA to (R)-mevalonate in three enzymatic steps (FIG. 7). The bottom operon converts the (R)-mevalonate to IPP, DMAPP and/or FPP depending on the construct (FIG. 7). To test the functionality of the heterologous pathway, an *E. coli* strain deficient in isoprenoid synthesis (strain DYM1) was transformed with plasmids expressing the three different bottom operon constructs pMevB, pMBI and pMBIS (FIG. 7). Strain DYM1 has a deletion in the ispC gene (Kuzuyama, et al. (1999) *Biosci. Biotechnol. Biochem.* 63:776–778) and therefore, cannot synthesize 2-C-methyl-D-erythritol 4-phosphate, an intermediate in the endogenous isoprenoid biosynthetic pathway (FIG. 7).

a) Strains and Media

*E. coli* DH10B was used as the cloning and isoprenoid expression strain. Table 1 provides a summary of the strains and plasmids used in this example.

TABLE 1

Summary of strains and plasmids used

| Strain or Plasmid | Description | Source |
|---|---|---|
| E.coli DH10B | | Gibco-Life Technologies |
| E.coli DYM1 | dxr E. coli strain | Kuzuyama, et al. (1999) Biosci. Biotechnol. Biochem. 63:776–778 |
| pCR4 | TA cloning vector; Ap$^R$ | Invitrogen |
| pTrc99A | High-copy expression plasmid; Ap$^R$ | Pharmacia |
| pBBR1MCS-3 | Low-copy broad-host expression plasmid; Tc$^R$ | Kovach et al. (1995) Gene 166:175–176 |
| pBAD33 | Low-copy broad-host expression plasmid; Cm$^R$ | Guzman et al. (1995) J.Bacteriol. 177:4121–4130 |
| pLac33 | Low-copy broad-host expression plasmid; Cm$^R$ | this example |
| pSOE4 | SOE4 operon expression plasmid; Cm$^R$ | this example |
| pAC-LYC04 | Plasmid expressing the IPP isomerase (ippHp) isolated from *Haematococcus pluvialis*; Cm$^R$ | Cunningham et al. (1994) Plant Cell 6:1107–1121 |
| pMevB | MevB operon expression plasmid.; Tc$^R$ | this example |
| pMBI | MBI operon expression plasmid.; Tc$^R$ | this example |
| pMBIS | MBIS operon expression plasmid; Tc$^R$ | this example |
| pMevT | MevT operon expression plasmid; Cm$^R$ | this example |
| pADS | Synthetic amorpha-4,11-diene synthase expression plasmid; Ap$^R$ | this example |

For the growth studies, the optical density of cultures expressing the various recombinant pathways was measured with a microtiter plate reader (SpectraMax, Molecular Devices) from 200 μl cultures of LB broth in 96-well plates incubated at 37° C. with continuous shaking. (±)-Mevalonolactone was purchased from Sigma-Aldrich (St. Louis, Mo.) and 2-C-methyl-D-erythritol was synthesized from citraconic anhydride according to the protocol of Duvold et al. (1997) *Tetrahedron Lett.* 38:4769–4772. The ispC mutant *E. coli* strain DYM1 (Kuzuyama et al. (1999) *Biosci. Biotechnol. Biochem.* 63:776–778), kindly provided by Dr. Haruo Seto at the University of Tokyo, was used to test the functionality of the synthetic mevalonate operons. The DYM1 strain was propagated on LB medium containing 0.5 mM 2-C-methyl-D-erythritol (ME) and transformed DYM1 cells were first allowed to recover on plates supplemented with ME before streaking them on test media. Media used to test the functionality of the operons were supplemented with 1 mM DL-mevalonate prepared by mixing 1 volume of 2 M DL-mevalonolactone with 1.02 volumes of 2 M KOH and incubating at 37° C. for 30 min (Campos et al. (2001) *Biochem. J.* 353:59–67).

As expected, all strains grew in the presence of ME, but only the strains harboring pMBI or pMBIS and not pMevB grew on plates supplemented with 1 mM mevalonate in the absence of ME. These results established that the synthetic MBI and MBIS operons were functional and capable of supplying IPP and DMAPP required for the growth of *E. coli*. Because the DXP pathway supplies the cells with IPP and DMAPP from a branch point (Rohdich et al. (2002) *Proc. Natl. Acad. Sci. USA* 99:1158–1163), a mutation in ispC prohibits the synthesis of both pyrophosphate precursors. Although *E. coli* maintains a nonessential copy of the IPP isomerase gene on its chromosome (Hahn et al. (1999) *J. Bacteriol.* 181:4499–4504), the expression of the gene appeared to be too low to support the growth of *E. coli* when only IPP is supplied by the MevB operon.

b) Synthesis of amorpha-4,11-diene Synthase Gene

The synthetic amorpha-4,11-diene synthase (ADS) gene (SEQ ID NO:37) was designed using Calcgene (Hale et al. (1998) *Protein Exper. Purif.* 12:185–188) and the protein sequence of the synthase (SEQ ID NO:38) isolated by the method described in Mercke et al. (2000) *Arch. Biochem. Biophys.* 381:173–180.

Eighty-four overlapping oligonucleotides (Gibco BRL) were used to produce the ADS gene: T-1 to T-41 (SEQ ID NO:41 to SEQ ID NO:81; stop sequence, SEQ ID NO:82) and B-1 to B-41 (SEQ ID NO:83 to SEQ ID NO:123; stop sequence, SEQ ID NO:124). To assemble the ADS gene, each of the eighty-four overlapping oligonucleotides, was dissolved in dH$_2$O to a final concentration of 100 μM. A mixture was prepared by combining 10 μL of each of the individual oligonucleotides. The first PCR reaction in the two-step PCR assembly of ADS contained in 100 μL, 1×Pfu polymerase buffer (20 mM Tris-HCl pH 8.8, 2 mM MgSO$_4$ 10 mM KCl, 10 mM (NH$_4$)$_2$SO$_4$, 0.1% Triton X100, 0.1% mg/mL BSA), 0.25 mM of each dNTP, 1 μM of oligonucleotides mixture and 5 U Pfu polymerase (Stratagene). The PCR cycling program was 94° C. for 30 s, 40° C. for 2 min, 72° C. for 10 s followed by 40 cycles of 94° C. for 15 s, 40° C. for 30 s, 72° C. for 20 s+3 s per cycle. The second PCR reaction contained in 100 μL, 33 μL of the first assembly reaction, 1×Pfu buffer, 0.25 mM of each dNTP and 5U Pfu polymerase. The PCR program for the second step of the assembly was as follows: 94° C. for 30 s, 40° C. for 10 s, 72° C. for 10 s followed by 25 cycles of 94° C. for 15 s, 40° C. for 30 s, 72° C. for 45 s+1 s per cycle. The DNA smear in the range of 1.7 kb was gel purified and used as template for a third and final PCR reaction containing in 100 μL, 1×Pfu buffer, 0.25 mM of each dNTP, 250 nM each of the two outside primers (T-1 and B-42), 10 μL of the gel purified DNA and 5 U Pfu polymerase. The PCR program was 40 cycles of 94° C. for 45 s and 72° C. for 4 min followed by a final step at 72° C. for 10 min. The expected 1.7 kb band was gel purified and ligated into pTrc99A using 5'-NcoI and 3'-XmaI sites designed into the gene sequence, thereby generating pADS. Two rounds of site-directed mutagenesis were needed to eliminate point mutations and generate a functional gene.

c) Construction of the DXP Pathway Operon

The dxs gene of *E. coli* was spliced to the IPP isomerase gene (ippHp) from pAC-LYC04 (Cunningham et al. (1994) *Plant Cell* 6:1107–1121) using overlapping extensions and PCR primers dxs1 (SEQ ID NO:30), dxs2 (SEQ ID NO:31), ippHp1 (SEQ ID NO:32) and ippHp2 (SEQ ID NO:33)

```
                                               (SEQ ID NO:30)
5'-TTGGGCTAGCAGGAGGAATTCACCATGAGTTTTGATATTGCCAAATA
C-3'

(SEQ ID NO:31)
5'-TCTGAGCAACGAACGAAGCATATATTTATGTCCTCCAGGCCTTGATT
TTG-3'

(SEQ ID NO:32)
5'-CAAAATCAAGGCCTGGAGGACATAAATATATGCTTCGTTCGTTGCTC
AGA-3'

(SEQ ID NO:33)
5'-GCATCCATGGTATCATCCTCCGTTGATGTGATG-3'
```

The E. coli ispA gene was isolated by PCR using primers ispa1 (SEQ ID NO:34) and ipsa2 (SEQ ID NO:35) and ligated to the NcoI site 3' to ippHp. The three-gene DXP operon was amplified with primers SOE-f (SEQ ID NO:36) and ispa2 (SEQ ID NO:35) and cloned into the KpnI-PstI sites of pMevT thereby replacing the MevT operon with the SOE4 operon.

```
                                               (SEQ ID NO:34)
5'-TGATACCATGGACTTTCCGCAGCAACTCG-3'

(SEQ ID NO:35)
5'-GTACATGCATTTATTTATTACGCTGGATGATG-3'

(SEQ ID NO:36)
5'-TGGGTACCGGGCCCCCCCTCGCCTCTAGAGTCGACTAGGAGGAATTC
ACCATGAGTTTTG-3'
``` d) Construction of the Mevalonate Pathway Operons

To complete the mevalonate pathway and allow the synthesis of sesquiterpene precursors from a simple and inexpensive carbon source, the pMevT plasmid expressing the remaining three genes (atoB, HMGS and tHMGR) of the mevalonate isoprenoid pathway was co-transformed with either pMBI or pMBIS. Co-expression of the two operons, which together encode a complete pathway for the synthesis of isoprenoids from acetyl-CoA, was able to complement the ispC deletion even in the absence of mevalonate, indicating that the MevT operon was functional (data not shown).

First, the Saccharomyces cerevisiae mevalonate pathway was engineered as two separate, independently expressed operons. The genes encoding the last three enzymes of the biosynthetic pathway, mevalonate kinase (MK or ER G12), phosphomevalonate kinase (PMK or ERG18) and mevalonate pyrophosphate decarboxylase (MPD or ERG19) were isolated by PCR from chromosomal DNA preparations of S. cerevisiae. The individual genes were spliced together (MevB) using overlapping extensions from primers MK-f (SEQ ID NO:14), MK-r (SEQ ID NO:15), PMK-f (SEQ ID NO:16), PMK-r (SEQ ID NO:17), MPD-f (SEQ ID NO:18) and MPD-r (SEQ ID NO:19).

```
                                               (SEQ ID NO:14)
5'-GATCTGCAGTAGGAGGAATTAACCATGCATTACCGTTCTTAACT-3'

(SEQ ID NO:15)
5'-TTGATCTGCCTCCTATGAAGTCCATGGTAAATT-3'

(SEQ ID NO:16)
5'-ACTTCATAGGAGGCAGATCAAATGTCAGAGTTGAGAGCCTTC-3'

(SEQ ID NO:17)
5'-GAGTATTACCTCCTATTTATCAAGATAAGTTTC-3'

(SEQ ID NO:18)
5'-GATAAATAGGAGGTAATACTCATGACCGTTTACACAGCATCC-3'

(SEQ ID NO:19)
5'-TACCTGCAGTTATTCCTTTGGTAGACCAGT-3'
```

The genes encoding the first three enzymes of the mevalonate pathway, the acetoacetyl-CoA thiolase from E. coli (AACT or atoB), 3-hydroxy-3-methylglutaryl-CoA synthase (HMGS or ERG13) and a truncated version of 3-hydroxy-3-methylglutaryl-CoA reductase (Polakowski et al. (1998) Appl. Microbiol. Biotechnol. 49:66–71) (tHMGR1) were isolated and spliced together as a single operon (MevT) using the following primers: atoB-f (SEQ ID NO:20), atoB-r (SEQ ID NO:21), HMGS-f (SEQ ID NO:22), HMGS-r (SEQ ID NO:23), tHMGR-f (SEQ ID NO:24) and tHMGR-r (SEQ ID NO:25).

```
                                               (SEQ ID NO:20)
5'-GATGTCGACTAGGAGGAATATAAAATGAAAAATTGTGTCATCGTC-
3'

(SEQ ID NO:21)
5'-TTAGCTGTCCTCCTTAATTCAACCGTTCAATCAC-3'

(SEQ ID NO:22)
5'-GATGTCGACAGGAGGACAGCTAAATGAAACTCTCAACTAAACTTTG-
3'

(SEQ ID NO:23)
5'-AGTGTAATCCTCCTTATTTTTAACATCGTAAG-3'

(SEQ ID NO:24)
5'-TTAAAAAATAAGGAGGATTACACTATGGTTTTAACCAATAAAACAG-
3'

(SEQ ID NO:25)
5'-ATCGTCGACTTAGGATTTAATGCAGGTGACGGACC-3'
```

Individual genes were isolated via PCR using Pfu DNA polymerase and a standard PCR protocol. The synthetic operons were ligated into pCR4 (TA vector from Invitrogen), after the addition of 3' A-overhangs, and sequenced to ensure accuracy. The MevB operon was ligated into the PstI site of pBBR1MCS-3 (Kovach et al., Gene 166:175–176, 1995) generating pMevB. The idi gene was ligated into the XmaI site, 3' to MevB using primers idi-f (SEQ ID NO:26) and idi-r (SEQ ID NO:27).

```
                                               (SEQ ID NO:26)
5'-ATCCCGGGAGGAGGATTACTATATGCAAACGGAACACGTC-3'

(SEQ ID NO:27)
5'-ATCCCGGGTTATTTAAGCTGGGTAAATG-3'
```

The MBI operon was moved to the SalI-SacI sites of pBBR1MCS-3 to generate pMBI. The ispA gene from E. coli was ligated into the SacI-SacII sites of pMBI using primers ispa-f (SEQ ID NO:28) and ispa-r (SEQ ID NO:29) thereby producing pMBIS.

```
                                               (SEQ ID NO:28)
5'-AGATCCGCGGAGGAGGAATGAGTAATGGACTTTCCGCAGCAAC-3'

(SEQ ID NO:29)
5'-AGTGAGAGCTCTTATTTATTACGCTGGATGATG-3'
```

The MevT operon was ligated into the XmaI-PstI sites of pBAD33 (Guzman et al., J. Bacteriol. 177:4121–4130, 1995). To place the operon under control of the $P_{LAC}$ promoter, the araC-$P_{BAD}$ NsiI-XmaI fragment was replaced with the NsiI-XmaI fragment of pBBR1MCS thereby generating pMevT. To generate pLac33, the MevT operon was excised from pMevT with SalI.

e) GC-MS Analysis of amorpha-4,11-diene

To achieve high-level production of amorpha-4,11-diene and to determine if the supply of FPP to the terpene synthase was limiting amorpha-4,11-diene yields, the mevalonate pathway was coupled to amorpha-4,11-diene synthesis in *E. coli*. Cells harboring the ADS gene co-expressed with the MBIS bottom operon were grown in medium supplemented with exogenous mevalonate.

Amorpha-4,11-diene production by the various strains was measured by GC-MS as described in Martin et al. (2001) *Biotechnol. Bioeng.* 75:497–503, by scanning only for two ions, the molecular ion (204 m/z) and the 189 m/z ion. Cells were grown in LB medium at 37° C. for 2 hrs and induced to express the ADS and the mevalonate pathway by the simultaneous addition of 0.5 mM IPTG ((FIG. 8A) and varying concentrations of (±)-mevalonate (FIG. 8B). Amorpha-4,11-diene concentrations were converted to caryophyllene equivalents using a caryophyllene standard curve and the relative abundance of ions 189 and 204 m/z of the two compounds. The sesquiterpene caryophyllene was purchased from Sigma-Aldrich (St. Louis, Mo.).

Figure 8A:
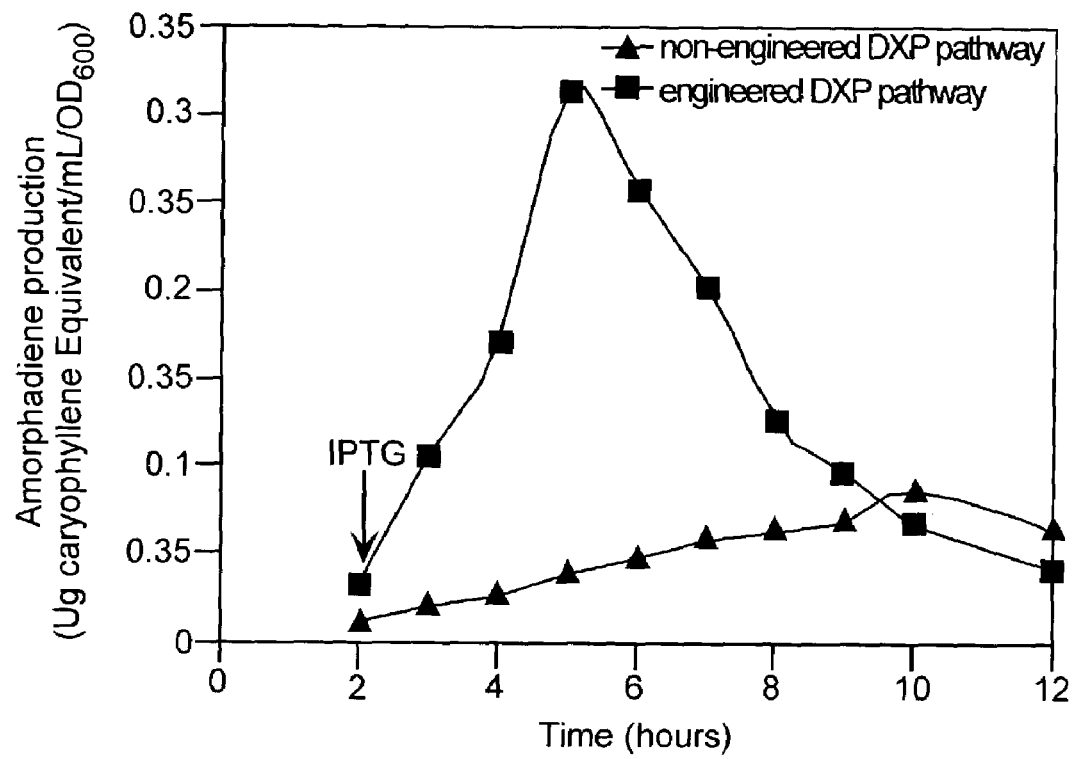
FIGS. 8A and 8B are graphs that compare production of amorpha-4,11-diene in LB medium.
Figure 8B:
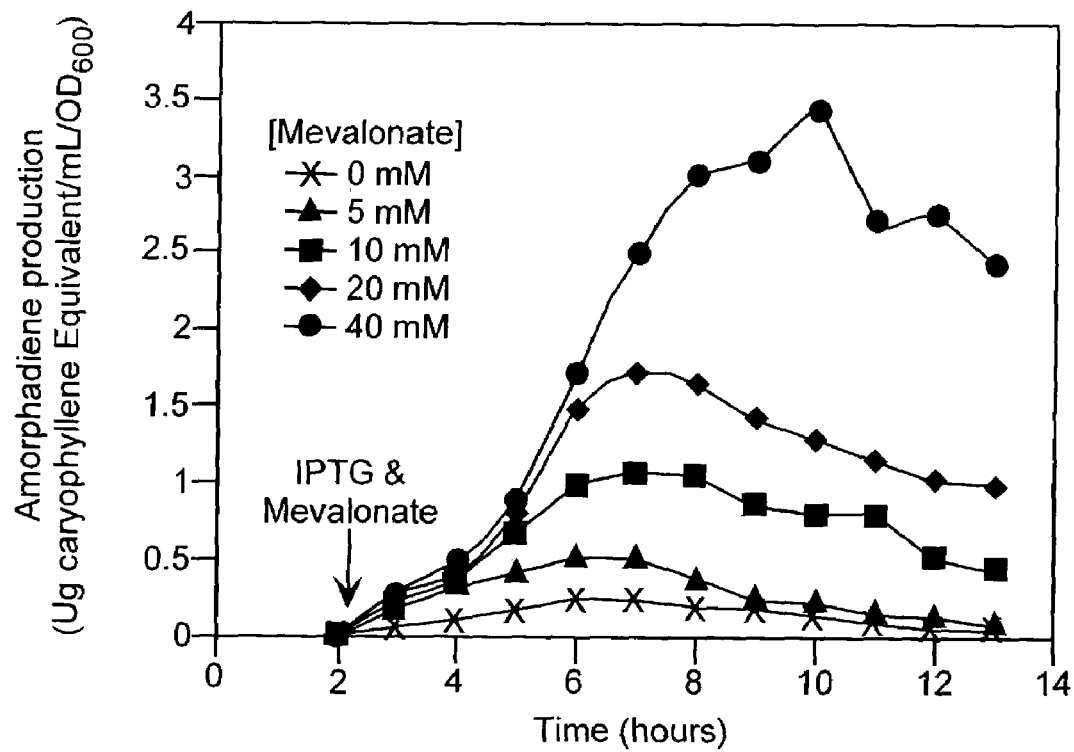

Expression of the synthetic ADS gene in *E. coli* DH10B resulted in a peak concentration of amorpha-4,11-diene of 0.086 µg caryophyllene equivalent/mL/$OD_{600}$ after 10 hours of growth in LB medium (FIG. 8A). The peak concentration of amorpha-4,11-diene increased to 0.313 µg caryophyllene equivalent/mL/$OD_{600}$ (FIG. 8A) upon co-expression with the SOE4 operon encoding DXS, IPPHp and IspA (FIG. 7), which are rate-limiting enzymes of the native DXP isoprenoid pathway. Although a 3.6-fold increase in amorpha-4,11-diene concentration was observed from the co-expression of the SOE4 operon and the synthetic ADS gene, is it believed that FPP synthesis and not ADS expression limited amorpha-4,11-diene production in this engineered host.

GC-MS analysis of the culture extracts revealed that the peak amorpha-4,11-diene concentration from these cultures was proportional to the amount of mevalonate added to the medium, up to a concentration of 40 mM mevalonate (FIG. 8B). These results indicated that flux from the MBIS operon did not limit amorpha-4,11-diene production at the highest mevalonate concentration used. Cultures supplemented with 40 mM mevalonate produced a peak concentration of 3.4 µg caryophyllene equivalents/mL/$OD_{600}$, which is a 40- and 11-fold increase over the endogenous and engineered DXP pathway, respectively. The drop in amorpha-4,11-diene concentration with time was due to the loss of the volatile terpene to the headspace, which means that these reported production values are certainly underestimated.

Figure 9A:
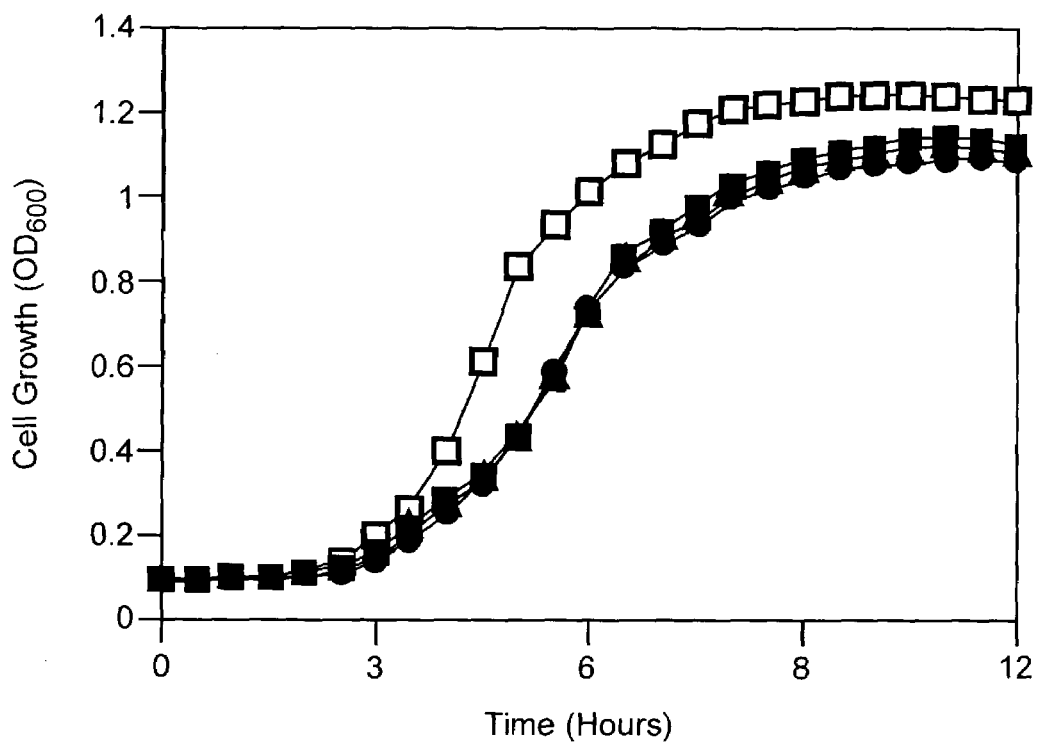
FIGS. 9A, 9B and 9C are growth curves of *E. coli* showing the inhibition effect cause by increasing concentrations of (±)-mevalonate in the LB medium. The *E. coli* strains are harboring either the pBBR1MCS-3 (empty plasmid control) (empty square), pMKPMK (solid circle), pMevB (solid diamond), pMBI (solid triangle) or pMBIS (solid square) plasmids expressing the various mevalonate operons described in FIG. 7. Each figure illustrates a different mevalonate concentration: 1 mM (FIG. 9A), 5 mM (FIG. 9B), and 10 mM (FIG. 9C).
Figure 9B:
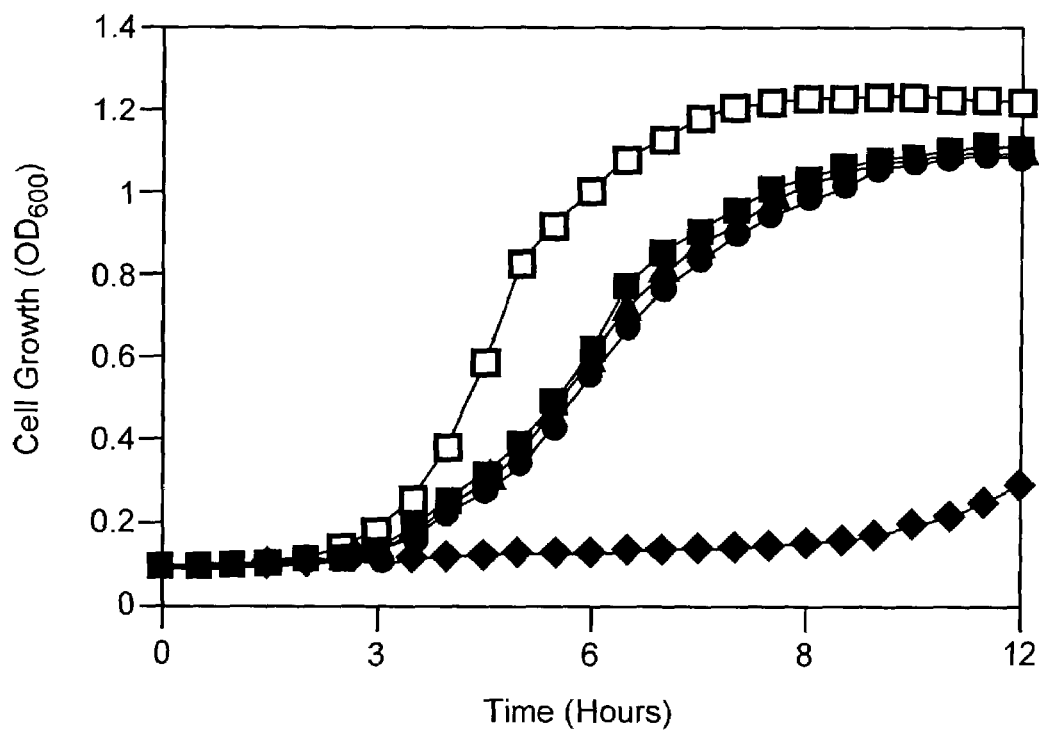
Figure 9C:
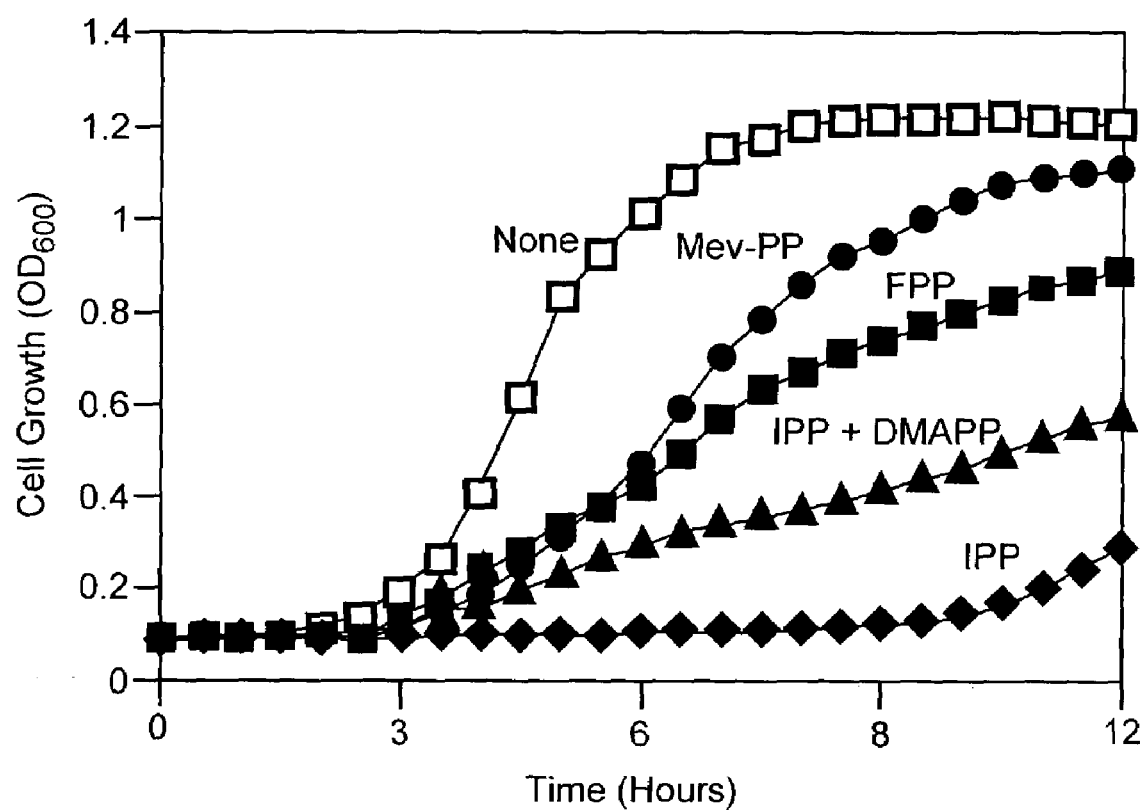

Severe growth inhibition was observed upon addition of greater than 10 mM mevalonate in the control cultures where the amorpha-4,11-diene synthase was not expressed (FIG. 9C). To investigate the cause of this inhibition, measurements were made of the growth of *E. coli* DH10B from strains harboring either the pMKPMK, pMevB, pMBI or pMBIS plasmid in media supplemented with increasing concentrations of exogenous Mevalonate. While the addition of 5 mM mevalonate to the media inhibited the growth of cells harboring pMevB, this concentration of mevalonate did not affect the growth of cells harboring pMKPMK, pMBI or pMBIS (FIG. 9B). Expression of the operons in the absence of mevalonate or in media supplemented with 1 mM mevalonate resulted in only a slight decrease in growth (FIG. 9A). Thus, from this data it was hypothesized that the accumulation of IPP, which occurs in cells with high flux through the mevalonate pathway, is toxic and inhibits normal cell growth.

f) Radio-HPLC Analysis of Intracellular Prenyl Pyrophosphates

To compare the intracellular prenyl pyrophosphate pools in the same strains, resting cells harboring the different mevalonate operon constructs were fed radiolabeled mevalonate and the labeled metabolites were tracked. Intracellular IPP+DMAPP and FPP levels were measured using a resting cell suspension assay supplemented with (R)-[5-$^3$H]-mevalonate (39 Ci/mmol, PerkinElmer Life Sciences, Boston Mass.). Cells induced with 0.5 mM IPTG cells then grown in LB broth at 37° C. to an $OD_{600}$ of ~0.6, harvested, washed once and suspended to 20-X concentration in 100 mM $KPO_4$ buffer (pH 7.4). Unlabeled (±)-mevalonate (10 mM) and $^3$H-radiolabeled (R)-mevalonate (60 µCi) were added to 8 mL of cell suspension and incubated at 37° C. Cells from 1.5 mL aliquots were washed twice with cold $KPO_4$ buffer and the intracellular IPP+DMAPP and FPP were extracted from cell pellets with 1 mL of methanol:chloroform (2:1). The cell extracts were dephosphorylated using potato acid phosphatase as previously described by Fujii et al. (1982) *Biochem. Biophys. Acta* 712:716–718. The prenyl alcohols were resolved on a reverse phase C-18 column (4.5 mm×250 mm 5µ particle size, Alltech) by HPLC (Agilent Technologies model 1100) using the method of Zhang et al. (1993) *Anal. Biochem.* 213:356–361, and detected with a flow-through scintillation counter (Packard BioScience, Radiomatic model 500TR).

Figure 10A:
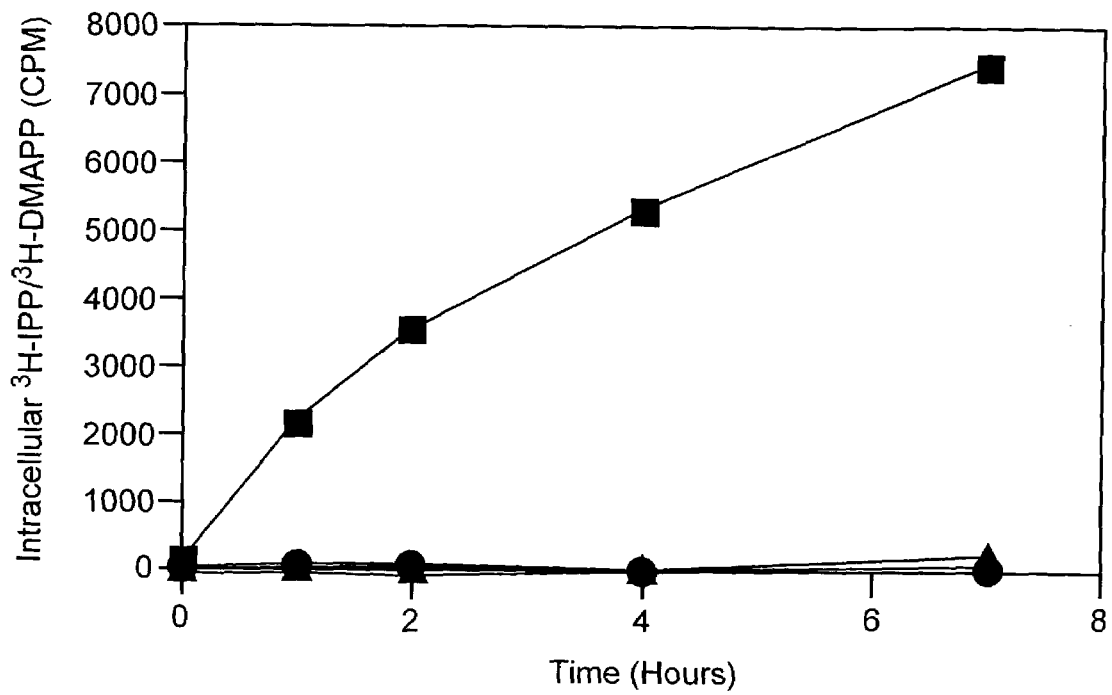
FIGS. 10A and 10B show the intracellular accumulation of $^3$H-isopentenyl pyrophosphate (IPP) and $^3$H-dimethylallyl pyrophosphate (DMAPP) (FIG. 10A), and $^3$H-farnesyl pyrophosphate (FPP) (FIG. 10B) from cell suspensions of *E. coli* harboring pMevB+pTrc99A (solid square), pMBI+ pTrc99A (solid triangle), pMBIS+pTrc99A (solid diamond) or pMBIS+pADS (solid circle). The HPLC method used to analyze IPP and DMAPP could not resolve the two intermediates. Therefore, the counts per minute (CPM) reported as IPP+DMAPP are from a single HPLC peak.
Figure 10B:
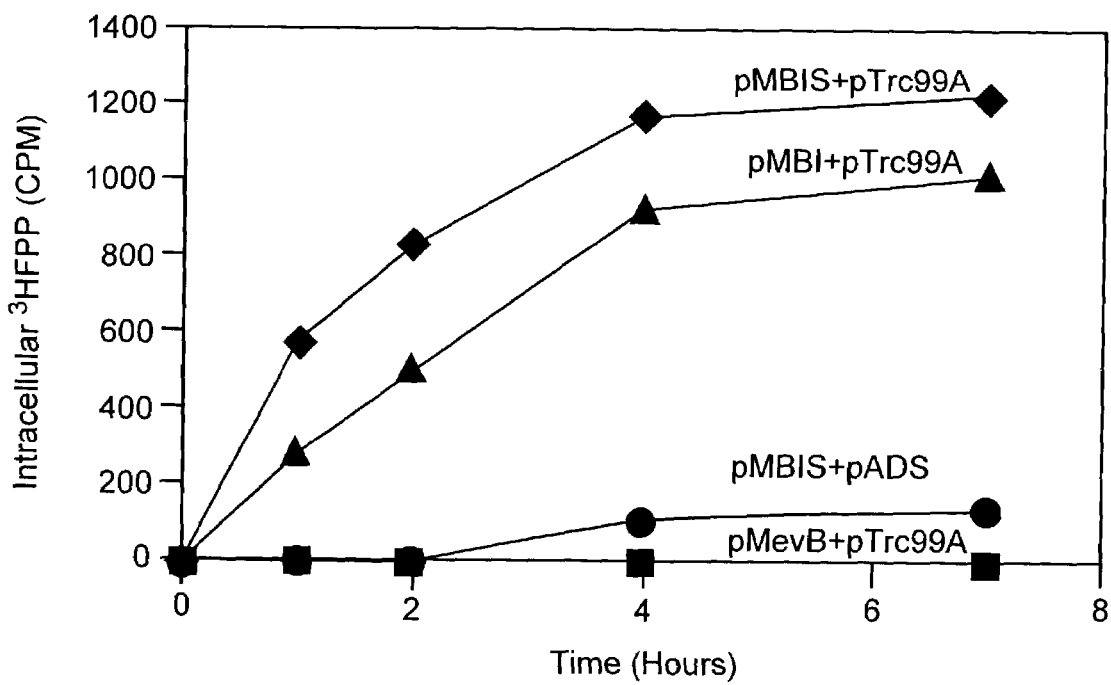

As predicted, the strain expressing MevB accumulated IPP but not FPP, whereas the MBI and MBIS strains accumulated FPP but did not build up measurable levels of intracellular IPP (FIGS. 10A and 10B). Simultaneous expression of the amorpha-4,11-diene synthase consumed the excess FPP pool accumulated in the MBIS host, as shown by a decrease in intracellular FPP.

Because cells expressing MBIS accumulated FPP and exhibited growth inhibition in the presence of 10 mM mevalonate, it was believed that the co-expression of the amorpha-4,11-diene synthase would alleviate the growth inhibition by channeling the intracellular prenyl pyrophosphate intermediates to the volatile terpene olefin. As expected, growth inhibition was only observed in strains lacking the ADS gene approximately 2 hours after addition of 10–40 mM mevalonate and IPTG (FIG. 11A). In contrast, cells co-expressing the MBIS operon and the synthase gene both under control of IPTG-inducible promoters exhibited normal growth rates at all mevalonate concentrations (FIG. 11B). As shown previously, amorpha-4,11-diene production from these cultures increased proportionally with the addition of exogenous mevalonate (FIG. 8B), further supporting the conclusion that the conversion of FPP to amorpha-4,11-diene plays a key role in minimizing growth inhibition. Taken together, these data strongly suggest that the engineered mevalonate pathway produces high levels of the pyrophosphate precursors. However, in the absence of the IPP isomerase, FPP synthase and terpene synthase to channel the pathway intermediates to the terpene olefin, toxic levels of intracellular pyrophosphates, especially IPP, may accumulate.

g) Amorpha-4,11-diene Synthesis from acetyl-CoA

To achieve amorpha-4,11-diene production from a simple and inexpensive carbon source, the pMevT plasmid was introduced into *E. coli* harboring the pMBIS and pADS plasmids. This strain was tested for its ability to produce amorpha-4,11-diene in the absence of exogenous mevalonate. Peak amorpha-4,11-diene production from the complete mevalonate pathway reached 3.1 µg caryophyllene equivalent/mL/$OD_{600}$ after 9 hrs of growth. This represents 36- and 10-fold improvements over the production from the strains with the native and engineered DXP pathway, which peaked at 0.086 and 0.31 µg caryophyllene equivalents/mL/$OD_{600}$, respectively (FIG. 12). From the comparison of the amorpha-4,11-diene production between the complete (FIG. 12) and the bottom (FIG. 8B) pathways, it was estimated that the MevT pathway produced the equivalent of approximately 40 mM of exogenous (±)-mevalonate. Glycerol was amended to the cultures to investigate the effect of supplementing an additional carbon source on amorpha-4,11-diene yields. The addition of 0.8% glycerol to the LB medium led to higher culture optical densities and prolonged amorpha-4,11-diene production well into stationary phase. The glycerol-amended culture reached optical densities of 3.7 and amorpha-4,11-diene concentrations of 24 µg caryophyllene equivalent per mL. Using the rate of amorpha-4,11-diene loss from the LB culture (FIG. 12) and assuming that the cells no longer produced amorpha-4,11-diene after 11 hours, the mass transfer coefficient was estimated to be 0.87/h. By using this coefficient to account for the loss of amorpha-4,11-diene to the headspace, it was estimated that a total production of approximately 22.6 and 112.2 mg/L from the LB and LB+0.8% glycerol cultures, respectively, was obtained. From these data, it is clear that the expression of the mevalonate-dependent isoprenoid biosynthetic pathway delivers high levels of isoprenoid precursor for the production of sesquiterpenes from a simple carbon source and that optimization of fermentation conditions should yield terpene production titers in the g/L range.

We claim:

1. A method for synthesizing amorpha-4,11-diene in a host microorganism, the method comprising:
    culturing a transformed host microorganism in a suitable medium, wherein the microorganism is a prokaryote that does not normally synthesize isopentenyl pyrophosphate (IPP) via a mevalonate pathway,
    wherein the microorganism comprises one or more nucleic acids heterologous to the microorganism, wherein the one or more heterologous nucleic acids comprises nucleotide sequences that encode two or more mevalonate pathway enzymes, wherein said two or more mevalonate pathway enzymes comprises an enzyme that condenses two molecules of acetyl-CoA to acetoacetyl-CoA as the first step in the synthesis of IPP via the mevalonate pathway, and one or more additional mevalonate pathway enzymes selected from:
    (i) an enzyme that condenses acetoacetyl-CoA with acetyl-CoA to form HMG-CoA;
    (ii) an enzyme that converts HMG-CoA to mevalonate;
    (iii) an enzyme that phosphorylates mevalonate to mevalonate 5-phosphate;
    (iv) an enzyme that converts mevalonate 5-phosphate to mevalonate 5-pvrophosphate; and
    (v) an enzyme that converts mevalonate 5-pyrophosphate to isopentenyl pvrophosphate;
    (b) an enzyme that converts isopentenyl pyrophosphate to dimethylallyl pyrophosphate;
    (c) a farnesyl pyrophosphate synthase; and
    (d) amorpha-4,11-diene synthase, wherein said culturing provides for production of said enzymes, and wherein said production of said enzymes results in production of amorpha-4,11-diene.

2. The method of claim 1, wherein the nucleic acid comprising a nucleotide sequence coding for synthetic amorpha-4,11-diene synthase comprises the nucleotide sequence of SEQ ID NO:37.

3. The method of claim 1, wherein the nucleic acid comprising a nucleotide sequence coding for a farnesyl pyrophosphate synthase comprises the nuelcotide sequence of SEQ ID NO:11.

4. The method of claim 1, wherein the one or more heterologous nucleic acids is integrated into the chromosome of the host microorganism.

5. The method of claim 1, wherein the one or more heterologous nucleic acids is contained in at least one extrachromosomal expression vector.

6. The method of claim 5, wherein the wherein the one or more heterologous nucleic acids is present in a single expression vector.

7. The method of claim 6, wherein the single expression vector comprises the nucleotide sequence set forth in SEQ ID NO:7.

8. The method of claim 5, wherein each of the one or more heterologous nucleic acids is contained within a separate expression vector.

9. The method of claim 5, wherein at least two of the one or more heterologous nucleic acids are contained in a single expression vector.

10. The method of claim 5, wherein the one or more heterologous nucleic acids is contained in two expression vectors.

11. The method of claim 10, wherein the first expression vector comprises the nucleotide sequence set forth in SEQ ID NO:8, and the second expression vector comprises the nucleotide sequence set forth in SEQ ID NO:9.

12. A method for synthesizing amorpha-4,11-diene in a host microorganism, the method comprising:
    culturing a transformed host microorganism in a suitable medium, the transformed host microorganism comprising one or more nucleic acids heterologous to the host microorganism, wherein the host microorganism is a prokaryote that does not normally synthesize isopentenyl pyrophosphate (IPP) via a mevalonate pathway, wherein the one or more nucleic acids comprises nucleotide sequences encoding:
    a) two or more enzymes selected from:
    i) an enzyme that condenses two molecules of acetyl-CoA to acetoacetyl-CoA, wherein said enzyme is from *Ralstonia, Saccharomyces,* or *Escherichia coli,* wherein said enzyme that condenses two molecules of acetyl-CoA to acetoacetyl-coA is present as the first step in the synthesis of IPP via the mevalonate pathway;
    ii) an enzyme that condenses acetoacetyl-CoA with acetyl-CoA to form HMG-CoA, wherein said enzyme is from *Blattella* or *Saccharomyes;*
    iii) an enzyme that converts HMG-CoA to mevalonate, wherein said enzyme is from *Sulfolobus, Haloferax,* or *Saccharomyces;* iv) a *Saccharomyces* enzyme that phosphorylates mevalonate to mevalonate 5-phosphate;
v) a *Saccharomyces* enzyme that converts mevalonate 5-phosphate to mevalonate 5-pyrophosphate; and
vi) a *Saccharomyces* enzyme that converts mevalonate 5-pyrophosphate to isopentenyl pyrophosphate;
b) an *Escherichia coli* enzyme that converts isopentenyl pyrophosphate to dimethylallyl pyrophosphate;
(c) an *Escherichia coli* farnesyl pyrophosphate synthase; and
(d) an amorpha-4,11-diene synthase encoded by the nucleotide sequence set forth in SEQ ID NO:37,
wherein said culturing provides for production of said enzymes, and wherein said production of said enzymes results in production of amorpha-4,11-diene.

13. The method of claim 12, wherein the one or more heterologous nucleic acids comprises: the nucleotide sequence of SEQ ID NO:1; the nucleotide sequence of SEQ ID NO:2; the nucleotide sequence of SEQ ID NO;3; the nucleotide sequence of SEQ ID NO:4; the nucleotide sequence of SEQ ID NO:5; and the nucleotide sequence of SEQ ID NO:6.

14. The method of claim 1, wherein the amorpha-4,11-diene is oxidized in the presence of at least one enzyme to provide artemisinic acid, which then undergoes an oxidation cyclization to form artemisinin.

15. The method of claim 1, wherein the host microorganism is a prokaryote.

16. The method of claim 15, wherein the prokaryote is *Eseherichia coli*.

17. A method for synthesizing amorpha-4,11-diene in a host microorganism, the method comprising:
culturing a transformed host microorganism in a suitable medium, the transformed host microorganism comprising one or more nucleic acids heterologous to the host microorganism, wherein the host microorganism is a prokaryote that does not normally synthesize isopentenyl pyrophosphate (IPP) via a mevalonate pathway, wherein the one or more nucleic acids comprises:
a) a nucleotide sequence encoding an acetoacetyl-CoA thiolase, wherein the acetoacetyl-CoA thiolase is present as the first step in the synthesis of IPP via the mevalonate pathway;
(b) a nucleotide sequence encoding a farnesyl pyrophosphate synthase; and
(c) a nucleotide sequence encoding amorpha-4,11-diene synthase, wherein said culturing provides for production of said enzymes, and wherein said production of said enzymes results in production of amorpha-4,11-diene.

18. The method of claim 17, wherein the amorpha-4,11-diene is oxidized in the presence of at least one enzyme to provide artemisinic acid, which then undergoes an oxidation cyclization to form artemisinin.

19. The method of claim 17, wherein the host microorganism is a prokaryote.

20. The method of claim 17, wherein the prokaryote is *Escherichia coli*.

21. A method for synthesizing amorpha-4,11-diene in a host microorganism, the method comprising:
culturing a transformed host microorganism in a suitable medium, the transformed host microorganism comprising one or more nucleic acids heterologous to the host microorganism, wherein the host microorganism is a prokaryote that does not normally synthesize isopentenyl pyrophosphate via a mevalonate pathway, wherein the one or more nucleic acids comprises:
(a) the nucleotide sequence set forth in SEQ ID NO:8;
(b) the nucleotide sequence set forth in SEQ ID NO:9;
(c) a nucleotide sequence encoding an enzyme that converts isopentenyl pyrophosphate to dimethylallyl pyrophosphate;
(d) a nucleotide sequence encoding a farnesyl pyrophosphate synthase; and
(e) a nucleotide sequence encoding amorpha-4,11-diene synthase, wherein said culturing provides for production of said enzymes, and wherein said production of said enzymes results in production of amorpha-4,11-diene.

22. The method of claim 21, wherein the one or more heterologous nucleic acids is contained in two separate expression vectors.

23. The method of claim 22, wherein the first expression vector comprises the nucleotide sequence set forth in SEQ ID NO:8, and the second expression vector comprises the nucleotide sequence set forth in SEQ ID NO:9.

24. The method of claim 21, wherein the amorpha-4,11-diene is oxidized in the presence of at least one enzyme to provide artemisinic acid, which then undergoes an oxidation cyclization to form artemisinin.

25. The method of claim 21, wherein the host microorganism is a prokaryote.

26. The method of claim 21, wherein the prokaryote is *Escherichia coli*.

27. A method for synthesizing amorpha-4,11-diene in a host microorganism, the method comprising:
culturing a transformed host microorganism in a suitable medium, the transformed host microorganism comprising one or more nucleic acids heterologous to the host microorganism, wherein the host microorganism is a prokaryote that does not normally synthesize isopentenyl pyrophosphate via a mevalonate pathway, wherein the one or more nucleic acids comprises:
(a) the nucleotide sequence set forth in SEQ ID NO:1, the nucleotide sequence of SEQ ID NO:2; the nucleotide sequence of SEQ ID NO:3; the nucleotide sequence of SEQ ID NO:4; the nucleotide sequence of SEQ ID NO:5; and the nucleotide sequence of SEQ ED NO:6;
(b) a nucleotide sequence encoding an enzyme that converts isopentenyl pyrophosphate to dimethylallyl pyrophosphate;
(c) a nucleotide sequence encoding a farnesyl pyrophosphate synthase; and
(d) a nucleotide sequence encoding amorpha-4,11-diene synthase, wherein said culturing provides for production of said enzymes, and wherein said production of said enzymes results in production of amorpha-4,11-diene.

28. The method of claim 27, wherein the amorpha-4,11-diene is oxidized in the presence of at least one enzyme to provide artemisinic acid, which then undergoes an oxidation cyclization to form artemisinin.

29. The method of claim 27, wherein the host microorganism is a prokaryote.

30. The method of claim 27, wherein the prokaryote is *Escherichia coli*.

31. The method of claim 1, wherein expression of the one or more nucleic acids results in production of amorpha-4,11-diene in a recoverable amount of at least about 1 mg/T.

32. The method of claim 1, wherein the transformed host microorganism comprises at least two operons, each operon comprising the one or more nucleic acids.

33. The method of claim 1, wherein the enzyme that converts isopentenyl pyrophosphate to dimethylallyl pyrophosphate is a heterologous isopentenyl pyrophosphate isomerase.

* * * * *

UNITED STATES PATENT AND TRADEMARK OFFICE
CERTIFICATE OF CORRECTION

PATENT NO. : 7,192,751 B2
APPLICATION NO. : 10/411066
DATED : March 20, 2007
INVENTOR(S) : Jay D. Keasling et al.

It is certified that error appears in the above-identified patent and that said Letters Patent is hereby corrected as shown below:

In claim 3, column 115, line 63, the word "nueleotide" should be replaced with --nucleotide-- as shown below:

3. The method of claim 1, wherein the nucleic acid comprising a nucleotide sequence coding for a farnesyl pyrophosphate synthase comprises the ~~nueleotide~~ nucleotide sequence of SEQ ID NO:11.

In claim 12, column 116, line 60, the word "coA" should be replaced with --CoA-- as shown below:

12. A method for synthesizing amorpha-4, 11-diene in a host microorganism, the method comprising:
culturing a transformed host microorganism in a suitable medium, the transformed host microorganism comprising one or more nucleic acids heterologous to the host microorganism, wherein the host microorganism is a prokaryote that does not normally synthesize isopentenyl pyrophosphate (IPP) via a mevalonate pathway, wherein the one or more nucleic acids comprises nucleotide sequences encoding:
   a) two or more enzymes selected from:
   i) an enzyme that condenses two molecules of acetyl-CoA to acetoacetyl-CoA, wherein said enzyme is from *Ralstonia*, *Saccharomyces*, or *Escherichia coli*, wherein said enzyme that condenses two molecules of acetyl-CoA to acetoacetyl-[[coA]] CoA is present as the first step in the synthesis of IPP via the mevalonate pathway;
   ii) an enzyme that condenses acetoacetyl-CoA with acetyl-CoA to form HMG-CoA, wherein said enzyme is from *Blattella* or *Saccharomyes*;
   iii) an enzyme that converts HMG-CoA to mevalonate, wherein said enzyme is from *Sulfolobus*, *Haloferax*, or *Saccharomyces*;
   iv) a *Saccharomyces* enzyme that phosphorylates mevalonate to mevalonate 5-phosphate;
   v) a *Saccharomyces* enzyme that converts mevalonate 5-phosphate to mevalonate 5- pyrophosphate; and
   vi) a *Saccharomyces* enzyme that converts mevalonate 5-pyrophosphate to isopentenyl pyrophosphate;
   b) an *Escherichia coli* enzyme that converts isopentenyl pyrophosphate to dimethylallyl pyrophosphate;
   (c) an *Escherichia coli* farnesyl pyrophosphate synthase; and
   (d) an amorpha-4,11-diene synthase encoded by the nucleotide sequence set forth in SEQ ID NO:37,
   wherein said culturing provides for production of said enzymes, and wherein said production of said enzymes results in production of amorpha-4,11-diene.

UNITED STATES PATENT AND TRADEMARK OFFICE
CERTIFICATE OF CORRECTION

PATENT NO. : 7,192,751 B2
APPLICATION NO. : 10/411066
DATED : March 20, 2007
INVENTOR(S) : Jay D. Keasling et al.

It is certified that error appears in the above-identified patent and that said Letters Patent is hereby corrected as shown below:

In claim 16, column 117, line 28, the word "*Eseherichia*" should be replaced with --*Escherichia*-- as shown below:

16. The method of claim 15, wherein the prokaryote is ~~*Eseherichia*~~ *Escherichia* coli.

Signed and Sealed this

Eighteenth Day of September, 2007

JON W. DUDAS
*Director of the United States Patent and Trademark Office*

SEQUENCE LISTING

<160> NUMBER OF SEQ ID NOS: 124

<210> SEQ ID NO 1
<211> LENGTH: 1185
<212> TYPE: DNA
<213> ORGANISM: Escherichia coli

<400> SEQUENCE: 1

```
atgaaaaatt gtgtcatcgt cagtgcggta cgtactgcta tcggtagttt taacggttca      60
ctcgcttcca ccagcgccat cgacctgggg gcgacagtaa ttaaagccgc cattgaacgt     120
gcaaaaatcg attcacaaca cgttgatgaa gtgattatgg gtaacgtgtt acaagccggg     180
ctggggcaaa atccggcgcg tcaggcactg ttaaaaagcg ggctggcaga aacggtgtgc     240
ggattcacgg tcaataaagt atgtggttcg ggtcttaaaa gtgtggcgct tgccgcccag     300
gccattcagg caggtcaggc gcagagcatt gtggcggggg gtatggaaaa tatgagttta     360 gcccctact tactcgatgc aaaagcacgc tctggttatc gtcttggaga cggacaggtt     420
tatgacgtaa tcctgcgcga tggcctgatg tgcgccaccc atggttatca tatggggatt     480
accgccgaaa acgtggctaa agagtacgga attacccgtg aaatgcagga tgaactggcg     540
ctacattcac agcgtaaagc ggcagccgca attgagtccg gtgctttac agccgaaatc     600 gtcccggtaa atgttgtcac tcgaaagaaa accttcgtct tcagtcaaga cgaattcccg     660
aaagcgaatt caacggctga agcgttaggt gcattgcgcc cggccttcga taaagcagga     720
acagtcaccg ctgggaacgc gtctggtatt aacgacggtg ctgccgctct ggtgattatg     780
gaagaatctg cggcgctggc agcaggcctt acccccctgg ctcgcattaa aagttatgcc     840
agcggtggcg tgccccccgc attgatgggt atggggccag tacctgccac gcaaaaagcg     900
ttacaactgg cggggctgca actggcggat attgatctca ttgaggctaa tgaagcattt     960
gctgcacagt tccttgccgt tgggaaaaac ctgggctttg attctgagaa agtgaatgtc    1020
aacggcgggg ccatcgcgct cgggcatcct atcggtgcca gtggtgctcg tattctggtc    1080
acactattac atgccatgca ggcacgcgat aaaacgctgg ggctggcaac actgtgcatt    1140
ggcggcggtc agggaattgc gatggtgatt gaacggttga attaa                    1185
```

<210> SEQ ID NO 2
<211> LENGTH: 1475

<212> TYPE: DNA
<213> ORGANISM: Saccharomyces cerevisiae

<400> SEQUENCE: 2

```
atgaaactct caactaaact ttgttggtgt ggtattaaag gaagacttag gccgcaaaag      60
caacaacaat acacaataca aacttgcaaa tgactgaact aaaaaaacaa agaccgctg     120
aacaaaaaac cagacctcaa aatgtcggta ttaaaggtat ccaaatttac atcccaactc    180
aatgtgtcaa ccaatctgag ctagagaaat tgatggcgt ttctcaaggt aaatacacaa     240
ttggtctggg ccaaaccaac atgtcttttg tcaatgacag agaagatatc tactcgatgt    300
ccctaactgt tttgtctaag ttgatcaaga gttacaacat cgacaccaac aaaattggta    360
gattagaagt cggtactgaa actctgattg acaagtccaa gtctgtcaag tctgtcttga    420
tgcaattgtt tggtgaaaac actgacgtcg aaggtattga cacgcttaat gcctgttacg    480
gtggtaccaa cgcgttgttc aactctttga actggattga atctaacgca tgggatggta    540
gagacgccat tgtagtttgc ggtgatattg ccatctacga taagggtgcc gcaagaccaa    600
ccggtggtgc cggtactgtt gctatgtgga tcggtcctga tgctccaatt gtatttgact    660
ctgtaagagc ttcttacatg aacacgcct acgatttta caagccagat ttcaccagcg      720
aatatcctta cgtcgatggt catttttcat taacttgtta cgtcaaggct cttgatcaag    780
tttacaagag ttattccaag aaggctattt ctaaagggtt ggttagcgat cccgctggtt    840
cggatgcttt gaacgttttg aaatatttcg actacaacgt tttccatgtt ccaacctgta    900
aattggtcac aaaatcatac ggtagattac tatataacga tttcagagcc atcctcaat    960
tgttcccaga agttgacgcc gaattagcta ctcgcgatta tgacgaatct ttaaccgata   1020
agaacattga aaaaactttt gttaatgttg ctaagccatt ccacaaagag agagttgccc   1080
aatctttgat tgttccaaca acacaggta acatgtacac cgcatctgtt tatgccgcct    1140
ttgcatctct attaaactat gttggatctg acgacttaca aggcaagcgt gttggtttat   1200
tttcttacgg ttccggtttta gctgcatctc tatattcttg caaaattgtt ggtgacgtcc   1260
aacatattat caaggaatta gatattacta acaaattagc caagagaatc accgaaactc   1320
caaaggatta cgaagctgcc atcgaattga gagaaaatgc ccatttgaag aagaacttca   1380
aacctcaagg ttccattgag catttgcaaa gtggtgttta ctacttgacc aacatcgatg   1440
acaaatttag aagatcttac gatgttaaaa aataa                              1475
```

<210> SEQ ID NO 3
<211> LENGTH: 1508
<212> TYPE: DNA
<213> ORGANISM: Saccharomyces cerevisiae

<400> SEQUENCE: 3

```
atggttttaa ccaataaaac agtcatttct gatcgaaagt caaaagttta tcatctgcgc      60
aatcgagctc atcaggacct tcatcatcta gtgaggaaga tgattcccgc gatattgaaa    120
gcttggataa gaaatacgt cctttagaag aattagaagc attattaagt agtgaaata     180
caaaacaatt gaagaacaaa gaggtcgctg ccttggttat tcacggtaag ttacctttgt    240
acgctttgga gaaaaaatta ggtgatacta cgagagcggt tgcggtacgt aggaaggctc    300
tttcaatttt ggcagaagct cctgtattag catctgatcg tttaccatat aaaaattatg    360
actacgaccg cgtatttggc gcttgttgtg aaaatgttat aggttacatg cctttgcccg    420
ttggtgttat aggcccccttg gttatcgatg gtacatctta tcatatacca atggcaacta   480
```

```
cagagggttg tttggtagct tctgccatgc gtggctgtaa ggcaatcaat gctggcggtg      540
gtgcaacaac tgttttaact aaggatggta tgacaagagg cccagtagtc cgtttcccaa      600
ctttgaaaag atctggtgcc tgtaagatat ggttagactc agaagaggga caaaacgcaa      660
ttaaaaaagc ttttaactct acatcaagat ttgcacgtct gcaacatatt caaacttgtc      720
tagcaggaga tttactcttc atgagattta gaacaactac tggtgacgca atgggtatga      780
atatgatttc taaaggtgtc gaatactcat taaagcaaat ggtagaagag tatggctggg      840
aagatatgga ggttgtctcc gtttctggta actactgtac cgacaaaaaa ccagctgcca      900
tcaactggat cgaaggtcgt ggtaagagtg tcgtcgcaga agctactatt cctggtgatg      960
ttgtcagaaa agtgttaaaa agtgatgttt ccgcattggt tgagttgaac attgctaaga     1020
atttggttgg atctgcaatg gctgggtctg ttggtggatt taacgcacat gcagctaatt     1080
tagtgacagc tgttttcttg gcattaggac aagatcctgc acaaaatgtt gaaagttcca     1140
actgtataac attgatgaaa gaagtggacg gtgatttgaa aatttccgta tccatgccat     1200
ccatcgaagt aggtaccatc ggtggtggta ctgttctaga accacaaggt gccatgttgg     1260
acttattagg tgtaagaggc ccgcatgcta ccgctcctgg taccaacgca cgtcaattag     1320
caagaatagt tgcctgtgcc gtcttggcag gtgaattatc cttatgtgct gccctagcag     1380
ccggccattt ggttcaaagt catatgaccc acaacaggaa acctgctgaa ccaacaaaac     1440
ctaacaattt ggacgccact gatataaatc gtttgaaaga tgggtccgtc acctgcatta     1500
aatcctaa                                                              1508

<210> SEQ ID NO 4
<211> LENGTH: 1332
<212> TYPE: DNA
<213> ORGANISM: Saccharomyces cerevisiae

<400> SEQUENCE: 4 tgtcattac cgttcttaac ttctgcaccg ggaaaggtta ttattttttgg tgaacactct        60 gctgtgtaca acaagcctgc cgtcgctgct agtgtgtctg cgttgagaac ctacctgcta      120
ataagcgagt catctgcacc agatactatt gaattggact tcccggacat tagctttaat      180
cataagtggt ccatcaatga tttcaatgcc atcaccgagg atcaagtaaa ctcccaaaaa      240
ttggccaagg ctcaacaagc caccgatggc ttgtctcagg aactcgttag tcttttggat      300
ccgttgttag ctcaactatc cgaatccttc cactaccatg cagcgttttg tttcctgtat      360
atgtttgttt gcctatgccc ccatgccaag aatattaagt tttctttaaa gtctacttta      420
cccatcggtg ctgggttggg ctcaagcgcc tctatttctg tatcactggc cttagctatg      480
gcctacttgg gggggttaat aggatctaat gacttggaaa agctgtcaga aaacgataag      540
catatagtga atcaatgggc cttcataggt gaaaagtgta ttcacggtac cccttcagga      600
atagataacg ctgtggccac ttatggtaat gccctgctat ttgaaaaaga ctcacataat      660
ggaacaataa acacaaacaa tttttaagttc ttagatgatt tcccagccat tccaatgatc      720
ctaacctata ctagaattcc aaggtctaca aaagatcttg ttgctcgcgt tcgtgtgttg      780
gtcaccgaga aatttcctga agttatgaag ccaattctag atgccatggg tgaatgtgcc      840
ctacaaggct tagagatcat gactaagtta agtaaatgta aaggcaccga tgacgaggct      900
gtagaaacta ataatgaact gtatgaacaa ctattggaat tgataagaat aaatcatgga      960
ctgcttgtct caatcggtgt ttctcatcct ggattgaaac ttattaaaaa tctgagcgat     1020
gatttgagaa ttggctccac aaaaacttacc ggtgctggtg gcggcggttg ctctttgact     1080
```

```
ttgttacgaa gagacattac tcaagagcaa attgacagct tcaaaaagaa attgcaagat   1140
gattttagtt acgagacatt tgaaacagac ttgggtggga ctggctgctg tttgttaagc   1200
gcaaaaaatt tgaataaaga tcttaaaatc aaatccctag tattccaatt atttgaaaat   1260
aaaactacca caaagcaaca aattgacgat ctattattgc aggaaacac gaatttacca    1320 tggacttcat ag                                                      1332
```

<210> SEQ ID NO 5
<211> LENGTH: 1356
<212> TYPE: DNA
<213> ORGANISM: Saccharomyces cerevisiae

<400> SEQUENCE: 5

```
atgtcagagt tgagagcctt cagtgcccca gggaaagcgt tactagctgg tggatattta    60
gttttagata caaatatga agcatttgta gtcggattat cggcaagaat gcatgctgta    120
gcccatcctt acggttcatt gcaagggtct gataagtttg aagtgcgtgt gaaaagtaaa   180
caatttaaag atggggagtg gctgtaccat ataagtccta aaagtggctt cattcctgtt    240
tcgataggcg gatctaagaa ccctttcatt gaaaaagtta tcgctaacgt atttagctac   300
tttaaaccta acatggacga ctactgcaat agaaacttgt tcgttattga tattttctct   360
gatgatgcct accattctca ggaggatagc gttaccgaac atcgtggcaa cagaagattg   420
agttttcatt cgcacagaat tgaagaagtt cccaaaacag gctgggctc ctcggcaggt    480 ttagtcacag ttttaactac agctttggcc tccttttttg tatcggacct ggaaaataat   540
gtagacaaat atagaagt tattcataat ttagcacaag ttgctcattg tcaagctcag     600
ggtaaaattg gaagcgggtt tgatgtagcg gcggcagcat atggatctat cagatataga   660
agattcccac ccgcattaat ctctaatttg ccagatattg gaagtgctac ttacggcagt   720
aaactggcgc atttggttga tgaagaagac tggaatatta cgattaaaag taaccattta   780
ccttcgggat taactttatg gatgggcgat attaagaatg gttcagaaac agtaaaactg   840
gtccagaagg taaaaaattg gtatgattcg catatgccag aaagcttgaa aatatataca    900
gaactcgatc atgcaaattc tagatttatg gatggactat ctaaactaga tcgcttacac   960
gagactcatg acgattacag cgatcagata tttgagtctc ttgagaggaa tgactgtacc   1020
tgtcaaaagt atcctgaaat cacagaagtt agagatgcag ttgccacaat tagacgttcc   1080
tttagaaaaa taactaaaga atctggtgcc gatatcgaac ctcccgtaca aactagctta   1140
ttggatgatt gccagacctt aaaaggagtt cttacttgct taatacctgg tgctggtggt    1200
tatgacgcca ttgcagtgat tactaagcaa gatgttgatc ttagggctca aaccgctaat   1260
gacaaaagat tttctaaggt tcaatggctg gatgtaactc aggctgactg gggtgttagg   1320
aaagaaaaag atccggaaac ttatcttgat aaatag                             1356
```

<210> SEQ ID NO 6
<211> LENGTH: 1191
<212> TYPE: DNA
<213> ORGANISM: Saccharomyces cerevisiae

<400> SEQUENCE: 6

```
atgaccgttt acacagcatc cgttaccgca cccgtcaaca tcgcaaccct taagtattgg    60
gggaaaaggg acacgaagtt gaatctgccc accaattcgt ccatatcagt gactttatcg   120
caagatgacc tcagaacgtt gacctctgcg gctactgcac ctgagtttga acgcgacact   180
```

-continued

```
ttgtggttaa atggagaacc acacagcatc gacaatgaaa gaactcaaaa ttgtctgcgc      240
gacctacgcc aattaagaaa ggaaatggaa tcgaaggacg cctcattgcc cacattatct      300
caatggaaac tccacattgt ctccgaaaat aactttccta cagcagctgg tttagcttcc      360
tccgctgctg gctttgctgc attggtctct gcaattgcta agttatacca attaccacag      420
tcaacttcag aaatatctag aatagcaaga aggggtctg gttcagcttg tagatcgttg        480
tttggcggat acgtggcctg ggaaatggga aaagctgaag atggtcatga ttccatggca      540
gtacaaatcg cagacagctc tgactggcct cagatgaaag cttgtgtcct agttgtcagc      600
gatattaaaa aggatgtgag ttccactcag ggtatgcaat tgaccgtggc aacctccgaa      660
ctatttaaag aaagaattga acatgtcgta ccaaagagat ttgaagtcat gcgtaaagcc      720
attgttgaaa aagatttcgc cacctttgca aaggaaacaa tgatggattc caactctttc      780
catgccacat gtttggactc tttccctcca atattctaca tgaatgacac ttccaagcgt      840
atcatcagtt ggtgccacac cattaatcag ttttacggag aaacaatcgt tgcatacacg      900
tttgatgcag gtccaaatgc tgtgttgtac tacttagctg aaaatgagtc gaaactcttt      960
gcatttatct ataaattgtt tggctctgtt cctggatggg acaagaaatt tactactgag     1020
cagcttgagg ctttcaacca tcaatttgaa tcatctaact ttactgcacg tgaattggat     1080
cttgagttgc aaaaggatgt tgccagagtg attttaactc aagtcggttc aggcccacaa     1140
gaaacaaacg aatctttgat tgacgcaaag actggtctac caaggaata a               1191
```

<210> SEQ ID NO 7
<211> LENGTH: 9253
<212> TYPE: DNA
<213> ORGANISM: Artificial Sequence
<220> FEATURE:
<223> OTHER INFORMATION: Description of Artificial Sequence: Synthetic "single operon" nucleotide sequence

<400> SEQUENCE: 7

```
gacgcttttt atcgcaactc tctactgttt ctccataccc gttttttttgg gctagcagga       60 ggaattcacc atggtacccg ggaggaggat tactatatgc aaacggaaca cgtcatttta      120
ttgaatgcac agggagttcc cacgggtacg ctggaaaagt atgccgcaca cacggcagac      180
acccgcttac atctcgcgtt ctccagttgg ctgtttaatg ccaaaggaca attattagtt      240
acccgccgcg cactgagcaa aaaagcatgg cctggcgtgt ggactaactc ggtttgtggg      300
cacccacaac tggagaaaag caacgaagac gcagtgatcc gccgttgccg ttatgagctt      360
ggcgtggaaa ttacgcctcc tgaatctatc tatcctgact ttcgctaccg cgccaccgat      420
ccgagtggca ttgtggaaaa tgaagtgtgt ccggtatttg ccgcacgcac cactagtgcg      480
ttacagatca atgatgatga agtgatggat tatcaatggt gtgatttagc agatgtatta      540
cacggtattg atgccacgcc gtgggcgttc agtccgtgga tggtgatgca ggcgacaaat      600
cgcgaagcca gaaacgatt atctgcattt acccagctta ataacccgg ggatcctcta         660 gagtcgacta ggaggaatat aaaatgaaaa attgtgtcat cgtcagtgcg gtacgtactg      720
ctatcggtag ttttaacggt tcactcgctt ccaccagcgc catcgacctg ggggcgacag      780
taattaaagc cgccattgaa cgtgcaaaaa tcgattcaca acacgttgat gaagtgatta      840
tgggtaacgt gttacaagcc gggctggggc aaaatccggc gcgtcaggca ctgttaaaaa      900
gcgggctggc agaaacggtg tgcggattca cggtcaataa agtatgtggt tcgggtctta      960
aaagtgtggc gcttgccgcc caggccattc aggcaggtca ggcgcagagc attgtggcgg     1020
```

-continued

```
ggggtatgga aaatatgagt ttagccccct acttactcga tgcaaaagca cgctctggtt   1080
atcgtcttgg agacggacag gtttatgacg taatcctgcg cgatggcctg atgtgcgcca   1140
cccatggtta tcatatgggg attaccgccg aaaacgtggc taaagagtac ggaattaccc   1200
gtgaaatgca ggatgaactg gcgctacatt cacagcgtaa agcggcagcc gcaattgagt   1260
ccggtgcttt tacagccgaa atcgtcccgg taaatgttgt cactcgaaag aaaaccttcg   1320
tcttcagtca agacgaattc ccgaaagcga attcaacggc tgaagcgtta ggtgcattgc   1380
gcccggcctt cgataaagca ggaacagtca ccgctgggaa cgcgtctggt attaacgacg   1440
gtgctgccgc tctggtgatt atggaagaat ctgcggcgct ggcagcaggc cttaccccc   1500
tggctcgcat aaaagttat gccagcggtg gcgtgccccc cgcattgatg ggtatggggc   1560
cagtacctgc cacgcaaaaa gcgttacaac tggcggggct gcaactggcg atattgatc   1620
tcattgaggc taatgaagca tttgctgcac agttccttgc cgttgggaaa aacctgggct   1680
ttgattctga gaaagtgaat gtcaacggcg gggccatcgc gctcgggcat cctatcggtg   1740
ccagtggtgc tcgtattctg gtcacactat acatgccat gcaggcacgc gataaaacgc   1800
tggggctgga aacactgtgc attggcgcg gtcagggaat gcgatggtg attgaacggt   1860
tgaattaagg aggacagcta atgaaactc tcaactaaac tttgttggtg tggtattaaa   1920
ggaagactta ggccgcaaaa gcaacaacaa ttacacaata caaacttgca aatgactgaa   1980
ctaaaaaac aaaagaccgc tgaacaaaaa accagacctc aaaatgtcgg tattaaaggt   2040
atccaaattt acatcccaac tcaatgtgtc aaccaatctg agctagagaa atttgatggc   2100
gtttctcaag gtaaatacac aattggtctg ggccaaacca acatgtcttt tgtcaatgac   2160
agagaagata tctactcgat gtccctaact gttttgtcta agttgatcaa gagttacaac   2220
atcgacacca acaaaattgg tagattagaa gtcggtactg aaactctgat tgacaagtcc   2280
aagtctgtca agtctgtctt gatgcaattg tttggtgaaa acactgacgt cgaaggtatt   2340
gacacgctta atgcctgtta cggtggtacc aacgcgttgt tcaactcttt gaactggatt   2400
gaatctaacg catgggatgg tagagacgcc attgtagttt gcggtgatat tgccatctac   2460
gataagggtg ccgcaagacc aaccggtggt gccggtactg ttgctatgtg gatcggtcct   2520
gatgctccaa ttgtatttga ctctgtaaga gcttcttaca tggaacacgc ctacgatttt   2580
tacaagccag atttcaccag cgaatatcct tacgtcgatg gtcatttttc attaacttgt   2640
tacgtcaagg ctcttgatca agtttacaag agttattcca agaaggctat ttctaaaggg   2700
ttggttagcg atcccgctgg ttcggatgct ttgaacgttt tgaaatattt cgactacaac   2760
gttttccatg ttccaacctg taattggtc acaaaatcat acggtagatt actatataac   2820
gatttcagag ccaatcctca attgttccca gaagttgacg ccgaattagc tactcgcgat   2880
tatgacgaat cttaaccga taagaacatt gaaaaaactt ttgttaatgt tgctaagcca   2940
ttccacaaag agagagttgc ccaatctttg attgttccaa caaacacagg taacatgtac   3000
accgcatctg tttatgccgc ctttgcatct ctattaaact atgttggatc tgacgactta   3060
caaggcaagc gtgttggttt attttcttac ggttccggtt tagctgcatc tctatattct   3120
tgcaaaattg ttggtgacgt ccaacatatt atcaaggaat tagatattac taacaaatta   3180
gccaagagaa tcaccgaaac tccaaaggat tacgaagctg ccatcgaatt gagagaaaat   3240
gcccatttga agaagaactt caaacctcaa ggttccattg agcatttgca agtggtgtt   3300
tactacttga ccaacatcga tgacaaattt agaagatctt acgatgttaa aaaataagga   3360
ggattacact atggttttaa ccaataaaac agtcatttct ggatcgaaag tcaaaagttt   3420
```

-continued

```
atcatctgcg caatcgagct catcaggacc ttcatcatct agtgaggaag atgattcccg    3480
cgatattgaa agcttggata agaaaatacg tcctttagaa gaattagaag cattattaag    3540
tagtggaaat acaaaacaat tgaagaacaa agaggtcgct gccttggtta ttcacggtaa    3600
gttacctttg tacgctttgg agaaaaaatt aggtgatact acgagagcgg ttgcggtacg    3660
taggaaggct ctttcaattt tggcagaagc tcctgtatta gcatctgatc gtttaccata    3720
taaaaattat gactacgacc gcgtatttgg cgcttgttgt gaaaatgtta taggttacat    3780
gcctttgccc gttggtgtta taggccccett ggttatcgat ggtacatctt atcatatacc    3840
aatggcaact acagagggtt gtttggtagc ttctgccatg cgtggctgta aggcaatcaa    3900
tgctggcggt ggtgcaacaa ctgttttaac taaggatggt atgacaagag cccagtagt    3960
ccgtttccca actttgaaaa gatctggtgc ctgtaagata tggttagact cagaagaggg    4020
acaaaacgca attaaaaaag cttttaactc tacatcaaga tttgcacgtc tgcaacatat    4080
tcaaacttgt ctagcaggag atttactctt catgagattt agaacaacta ctggtgacgc    4140
aatgggtatg aatatgattt ctaaaggtgt cgaatactca ttaaagcaaa tggtagaaga    4200
gtatggctgg gaagatatgg aggttgtctc cgtttctggt aactactgta ccgacaaaaa    4260
accagctgcc atcaactgga tcgaaggtcg tggtaagagt gtcgtcgcag aagctactat    4320
tcctggtgat gttgtcagaa aagtgttaaa aagtgatgtt ccgcattgg ttgagttgaa    4380
cattgctaag aatttggttg gatctgcaat ggctgggtct gttggtggat ttaacgcaca    4440
tgcagctaat ttagtgacag ctgttttctt ggcattagga caagatcctg cacaaaatgt    4500
tgaaagttcc aactgtataa cattgatgaa agaagtggac ggtgatttga gaatttccgt    4560
atccatgcca tccatcgaag taggtaccat cggtggtggt actgttctag aaccacaagg    4620
tgccatgttg gacttattag gtgtaagagg cccgcatgct accgctcctg gtaccaacgc    4680
acgtcaatta gcaagaatag ttgcctgtgc cgtcttggca ggtgaattat ccttatgtgc    4740
tgccctagca gccggccatt tggttcaaag tcatatgacc cacaacagga aacctgctga    4800
accaacaaaa cctaacaatt tggacgccac tgatataaat cgtttgaaag atgggtccgt    4860
cacctgcatt aaatcctaag tcgacctgca gtaggaggaa ttaccatgt cattaccgtt    4920
cttaacttct gcaccgggaa aggttattat ttttggtgaa cactctgctg tgtacaacaa    4980
gcctgccgtc gctgctagtg tgtctgcgtt gagaacctac ctgctaataa gcgagtcatc    5040
tgcaccagat actattgaat tggacttccc ggacattagc tttaatcata agtggtccat    5100
caatgatttc aatgccatca ccgaggatca agtaaactcc caaaaattgg ccaaggctca    5160
acaagccacc gatggcttgt ctcaggaact cgttagtctt ttggatccgt tgttagctca    5220
actatccgaa tccttccact accatgcagc gttttgtttc ctgtatatgt ttgtttgcct    5280
atgcccccat gccaagaata ttaagttttc tttaaagtct actttaccca tcggtgctgg    5340
gttgggctca agcgcctcta tttctgtatc actggcctta gctatggcct acttgggggg    5400
gttaatagga tctaatgact tggaaaagct gtcagaaaac gataagcata tagtgaatca    5460
atgggccttc ataggtgaaa agtgtattca cggtacccct tcaggaatag ataacgctgt    5520
ggccacttat ggtaatgccc tgctatttga aaaagactca cataatgaa caataaacac    5580
aaacaatttt aagttcttag atgatttccc agccattcca atgatcctaa cctatactag    5640
aattccaagg tctacaaaag atcttgttgc tcgcgttcgt gtgttggtca ccgagaaatt    5700
tcctgaagtt atgaagccaa ttctagatgc catgggtgaa tgtgccctac aaggcttaga    5760
```

```
gatcatgact aagttaagta aatgtaaagg caccgatgac gaggctgtag aaactaataa    5820
tgaactgtat gaacaactat tggaattgat aagaataaat catggactgc ttgtctcaat    5880
cggtgtttct catcctggat tagaacttat taaaaatctg agcgatgatt tgagaattgg    5940
ctccacaaaa cttaccggtg ctggtggcgg cggttgctct ttgactttgt tacgaagaga    6000
cattactcaa gagcaaattg acagcttcaa aaagaaattg caagatgatt ttagttacga    6060
gacatttgaa acagacttgg gtgggactgg ctgctgtttg ttaagcgcaa aaaatttgaa    6120
taaagatctt aaaatcaaat ccctagtatt ccaattattt gaaataaaa ctaccacaaa     6180 gcaacaaatt gacgatctat tattgccagg aaacacgaat ttaccatgga cttcatagga    6240
ggcagatcaa atgtcagagt tgagagcctt cagtgcccca gggaaagcgt tactagctgg    6300
tggatattta gttttagata caaaatatga agcatttgta gtcggattat cggcaagaat    6360
gcatgctgta gcccatcctt acggttcatt gcaagggtct gataagtttg aagtgcgtgt    6420
gaaaagtaaa caattaaaag atggggagtg gctgtaccat ataagtccta aaagtggctt    6480
cattcctgtt tcgataggcg gatctaagaa ccctttcatt gaaaaagtta tcgctaacgt    6540
atttagctac tttaaaccta acatggacga ctactgcaat agaaacttgt tcgttattga    6600
tattttctct gatgatgcct accattctca ggaggatagc gttaccgaac atcgtggcaa    6660
cagaagattg agttttcatt cgcacagaat tgaagaagtt cccaaaacag gctgggctc     6720 ctcggcaggt ttagtcacag ttttaactac agctttggcc tccttttttg tatcggacct    6780
ggaaaataat gtagacaaat atagagaagt tattcataat ttagcacaag ttgctcattg    6840
tcaagctcag ggtaaaattg aagcgggtt tgatgtagcg gcggcagcat atggatctat     6900
cagatataga agattcccac ccgcattaat ctctaatttg ccagatattg gaagtgctac    6960
ttacggcagt aaactggcgc atttggttga tgaagaagac tggaatatta cgattaaaag    7020
taaccattta ccttcgggat taactttatg gatgggcgat attaagaatg gttcagaaac    7080
agtaaaactg gtccagaagg taaaaaattg gtatgattcg catatgccag aaagcttgaa    7140
aatatataca gaactcgatc atgcaaattc tagatttatg gatggactat ctaaactaga    7200
tcgcttacac gagactcatg acgattacag cgatcagata tttgagtctc ttgagaggaa    7260
tgactgtacc tgtcaaaagt atcctgaaat cacagaagtt agagatgcag ttgccacaat    7320
tagacgttcc tttagaaaaa taactaaaga atctggtgcc gatatcgaac ctcccgtaca    7380
aactagctta ttggatgatt gccagaccct aaaaggagtt cttacttgct taatacctgg    7440
tgctggtggt tatgacgcca ttgcagtgat tactaagcaa gatgttgatc ttagggctca    7500
aaccgctaat gacaaaagat tttctaaggt tcaatggctg gatgtaactc aggctgactg    7560
gggtgttagg aaagaaaaag atccggaaac ttatcttgat aaataggagg taatactcat    7620
gaccgtttac acagcatccg ttaccgcacc cgtcaacatc gcaaccctta agtattgggg    7680
gaaaagggac acgaagttga atctgcccac caattcgtcc atatcagtga ctttatcgca    7740
agatgacctc agaacgttga cctctgcggc tactgcacct gagtttgaac gcgacacttt    7800
gtggttaaat ggagaaccac acagcatcga caatgaaaga actcaaaaatt gtctgcgcga    7860 cctacgccaa ttaagaaagg aaatggaatc gaaggacgcc tcattgccca cattatctca    7920
atggaaactc cacattgtct ccgaaaataa ctttcctaca gcagctggtt tagcttcctc    7980
cgctgctggc tttgctgcat tggtctctgc aattgctaag ttataccaat taccacagtc    8040
aacttcagaa atatctagaa tagcaagaaa ggggtctggt tcagcttgta gatcgttgtt    8100
tggcggatac gtggcctggg aaatgggaaa agctgaagat ggtcatgatt ccatggcagt    8160
```

-continued

```
acaaatcgca gacagctctg actggcctca gatgaaagct tgtgtcctag ttgtcagcga   8220
tattaaaaag gatgtgagtt ccactcaggg tatgcaattg accgtggcaa cctccgaact   8280
atttaaagaa agaattgaac atgtcgtacc aaagagattt gaagtcatgc gtaaagccat   8340
tgttgaaaaa gatttcgcca cctttgcaaa ggaaacaatg atggattcca actctttcca   8400
tgccacatgt ttggactctt tccctccaat attctacatg aatgacactt ccaagcgtat   8460
catcagttgg tgccacacca ttaatcagtt ttacggagaa acaatcgttg catacacgtt   8520
tgatgcaggt ccaaatgctg tgttgtacta cttagctgaa aatgagtcga aactctttgc   8580
atttatctat aaattgtttg gctctgttcc tggatgggac aagaaattta ctactgagca   8640
gcttgaggct ttcaaccatc aatttgaatc atctaacttt actgcacgtg aattggatct   8700
tgagttgcaa aaggatgttg ccagagtgat tttaactcaa gtcggttcag gcccacaaga   8760
aacaaacgaa tctttgattg acgcaaagac tggtctacca aaggaataac tgcaggcatg   8820
caagcttggc tgttttggcg gatgagagaa gattttcagc ctgatacaga ttaaatcaga   8880
acgcagaagc ggtctgataa aacagaattt gcctggcggc agtagcgcgg tggtcccacc   8940
tgaccccatg ccgaactcag aagtgaaacg ccgtagcgcc gatggtagtg tggggtctcc   9000
ccatgcgaga gtagggaact gccaggcatc aaataaaacg aaaggctcag tcgaaagact   9060
gggcctttcg ttttatctgt tgtttgtcgg tgaacgctct cctgagtagg acaaatccgc   9120
cgggagcgga tttgaacgtt gcgaagcaac ggcccggagg gtggcgggca ggacgcccgc   9180
cataaactgc caggcatcaa attaagcaga aggccatcct gacggatggc cttttgcgt   9240
ttctacaaac tct                                                     9253
```

<210> SEQ ID NO 8
<211> LENGTH: 4760
<212> TYPE: DNA
<213> ORGANISM: Artificial Sequence
<220> FEATURE:
<223> OTHER INFORMATION: Description of Artificial Sequence: Synthetic
      "MEVT" operon nucleotide sequence

<400> SEQUENCE: 8

```
gacgctttt atcgcaactc tctactgttt ctccataccc gttttttgg gctagcagga    60
ggaattcacc atggtacccg ggatcctct agagtcgact aggaggaata taaaatgaaa   120
aattgtgtca tcgtcagtgc ggtacgtact gctatcggta gttttaacgg ttcactcgct   180
tccaccagcg ccatcgacct gggggcgaca gtaattaaag ccgccattga acgtgcaaaa   240
atcgattcac aacacgttga tgaagtgatt atgggtaacg tgttacaagc cgggctgggg   300
caaaatccgg cgcgtcaggc actgttaaaa gcgggctgg cagaaacggt gtgcggattc   360
acggtcaata agtatgtgg ttcgggtctt aaaagtgtgg cgcttgccgc ccaggccatt   420
caggcaggtc aggcgcagag cattgtggcg gggggtatgg aaaatatgag tttagcccc   480
tacttactcg atgcaaaagc acgctctggt tatcgtcttg agacggaca ggtttatgac   540
gtaatcctgc gcgatggcct gatgtgcgcc acccatggtt atcatatggg gattaccgcc   600
gaaaacgtgg ctaaagagta cggaattacc cgtgaaatgc aggatgaact ggcgctacat   660
tcacagcgta aagcggcagc cgcaattgag tccggtgctt ttacagccga atcgtcccg   720
gtaaatgttg tcactcgaaa gaaaaccttc gtcttcagtc aagacgaatt cccgaaagcg   780
aattcaacgg ctgaagcgtt aggtgcattg cgcccggcct cgataaagc aggaacagtc   840
accgctggga acgcgtctgg tattaacgac ggtgctgccg ctctggtgat tatggaagaa   900
```

-continued

```
tctgcggcgc tggcagcagg ccttaccccc ctggctcgca ttaaaagtta tgccagcggt     960
ggcgtgcccc ccgcattgat gggtatgggg ccagtacctg ccacgcaaaa agcgttacaa    1020
ctggcggggc tgcaactggc ggatattgat ctcattgagg ctaatgaagc atttgctgca    1080
cagttccttg ccgttgggaa aaacctgggc tttgattctg agaaagtgaa tgtcaacggc    1140
ggggccatcg cgctcgggca tcctatcggt gccagtggtg ctcgtattct ggtcacacta    1200
ttacatgcca tgcaggcacg cgataaaacg ctggggctgg caacactgtg cattggcggc    1260
ggtcagggaa ttgcgatggt gattgaacgg ttgaattaag gaggacagct aaatgaaact    1320
ctcaactaaa ctttgttggt gtggtattaa aggaagactt aggccgcaaa agcaacaaca    1380
attacacaat acaaacttgc aaatgactga actaaaaaaa caaagaccg ctgaacaaaa     1440
aaccagacct caaaatgtcg gtattaaagg tatccaaatt tacatcccaa ctcaatgtgt    1500
caaccaatct gagctagaga aatttgatgg cgtttctcaa ggtaaataca caattggtct    1560
gggccaaacc aacatgtctt ttgtcaatga cagagaagat atctactcga tgtccctaac    1620
tgttttgtct aagttgatca agagttacaa catcgacacc aacaaaattg gtagattaga    1680
agtcggtact gaaactctga ttgacaagtc caagtctgtc aagtctgtct tgatgcaatt    1740
gtttggtgaa aacactgacg tcgaaggtat tgacacgctt aatgcctgtt acggtggtac    1800
caacgcgttg ttcaactctt tgaactggat tgaatctaac gcatgggatg gtagagacgc    1860
cattgtagtt tgcggtgata ttgccatcta cgataaggg tccgcaagac caaccggtgg     1920
tgccggtact gttgctatgt ggatcggtcc tgatgctcca attgtatttg actctgtaag    1980
agcttcttac atggaacacg cctacgattt ttacaagcca gatttcacca gcgaatatcc    2040
ttacgtcgat ggtcattttt cattaacttg ttacgtcaag gctcttgatc aagtttacaa    2100
gagttattcc aagaaggcta tttctaaagg gttggttagc gatcccgctg gttcggatgc    2160
tttgaacgtt ttgaaatatt tcgactacaa cgttttccat gttccaacct gtaaattggt    2220
cacaaaatca tacggtagat tactatataa cgatttcaga gccaatcctc aattgttccc    2280
agaagttgac gccgaattag ctactcgcga ttatgacgaa tctttaaccg ataagaacat    2340
tgaaaaaact tttgttaatg ttgctaagcc attccacaaa gagagagttg cccaatcttt    2400
gattgttcca acaaacacag gtaacatgta caccgcatct gtttatgccg cctttgcatc    2460
tctattaaac tatgttggat ctgacgactt acaaggcaag cgtgttggtt tattttctta    2520
cggttccggt ttagctgcat ctctatattc ttgcaaaatt gttggtgacg tccaacatat    2580
tatcaaggaa ttagatatta ctaacaaatt agccaagaga atcaccgaaa ctccaaagga    2640
ttacgaagct gccatcgaat tgagagaaaa tgcccatttg aagaagaact tcaaacctca    2700
aggttccatt gagcatttgc aaagtggtgt ttactacttg accaacatcg atgacaaatt    2760
tagaagatct tacgatgtta aaaataagg aggattacac tatggtttta accaataaaa     2820
cagtcatttc tggatcgaaa gtcaaaagtt tatcatctgc gcaatcgagc tcatcaggac    2880
cttcatcatc tagtgaggaa gatgattccc gcgatattga agcttggat aagaaaatac     2940
gtcctttaga agaattagaa gcattattaa gtagtggaaa tacaaaacaa ttgaagaaca    3000
aagaggtcgc tgccttggtt attcacggta agttaccttt gtacgctttg gagaaaaaat    3060
taggtgatac tacgagagcg gttgcggtac gtaggaaggc tctttcaatt ttggcagaag    3120
ctcctgtatt agcatctgat cgtttaccat ataaaaatta tgactacgac cgcgtatttg    3180
gcgcttgttg tgaaaatgtt ataggttaca tgcctttgcc cgttggtgtt ataggcccct    3240
```

-continued

```
tggttatcga tggtacatct tatcatatac caatggcaac tacagagggt tgtttggtag    3300
cttctgccat gcgtggctgt aaggcaatca atgctggcgg tggtgcaaca actgttttaa    3360
ctaaggatgg tatgacaaga ggcccagtag tccgtttccc aactttgaaa agatctggtg    3420
cctgtaagat atggttagac tcagaagagg gacaaaacgc aattaaaaaa gcttttaact    3480
ctacatcaag atttgcacgt ctgcaacata ttcaaacttg tctagcagga gatttactct    3540
tcatgagatt tagaacaact actggtgacg caatgggtat gaatatgatt tctaaaggtg    3600
tcgaatactc attaaagcaa atggtagaag agtatggctg ggaagatatg gaggttgtct    3660
ccgtttctgg taactactgt accgacaaaa aaccagctgc catcaactgg atcgaaggtc    3720
gtggtaagag tgtcgtcgca gaagctacta ttcctggtga tgttgtcaga aaagtgttaa    3780
aaagtgatgt ttccgcattg gttgagttga acattgctaa gaatttggtt ggatctgcaa    3840
tggctgggtc tgttggtgga tttaacgcac atgcagctaa tttagtgaca gctgttttct    3900
tggcattagg acaagatcct gcacaaaatg ttgaaagttc caactgtata acattgatga    3960
aagaagtgga cggtgatttg agaatttccg tatccatgcc atccatcgaa gtaggtacca    4020
tcggtggtgg tactgttcta gaaccacaag gtgccatgtt ggacttatta ggtgtaagag    4080
gcccgcatgc taccgctcct ggtaccaacg cacgtcaatt agcaagaata gttgcctgtg    4140
ccgtcttggc aggtgaatta tccttatgtg ctgccctagc agccggccat ttggttcaaa    4200
gtcatatgac ccacaacagg aaacctgctg aaccaacaaa acctaacaat tggacgcca    4260 ctgatataaa tcgtttgaaa gatgggtccg tcacctgcat taaatcctaa gtcgacctgc    4320
aggcatgcaa gcttggctgt tttggcggat gagagaagat tttcagcctg atacagatta    4380
aatcagaacg cagaagcggt ctgataaaac agaatttgcc tggcggcagt agcgcggtgg    4440
tcccacctga ccccatgccg aactcagaag tgaaacgccg tagcgccgat ggtagtgtgg    4500
ggtctcccca tgcgagagta gggaactgcc aggcatcaaa taaaacgaaa ggctcagtcg    4560
aaagactggg cctttcgttt tatctgttgt ttgtcggtga acgctctcct gagtaggaca    4620
aatccgccgg gagcggattt gaacgttgcg aagcaacggc ccggagggtg cgggcagga    4680 cgcccgccat aaactgccag gcatcaaatt aagcagaagg ccatcctgac ggatggcctt    4740
tttgcgtttc tacaaactct                                              4760
```

<210> SEQ ID NO 9
<211> LENGTH: 4482
<212> TYPE: DNA
<213> ORGANISM: Artificial Sequence
<220> FEATURE:
<223> OTHER INFORMATION: Description of Artificial Sequence: Synthetic
      "MEVB" operon nucleotide sequence

<400> SEQUENCE: 9

```
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctggg     180
tacccggccc ccctcgaggt cgacggtat cgataagctt gatatcgaat tcctgcagta     240
ggaggaatta accatgtcat taccgttctt aacttctgca ccgggaaagg ttattatttt     300
tggtgaacac tctgctgtgt acaacaagcc tgccgtcgct gctagtgtgt ctgcgttgag     360
aacctacctg ctaataagcg agtcatctgc accagatact attgaattgg acttcccgga     420
cattagcttt aatcataagt ggtccatcaa tgatttcaat gccatcaccg aggatcaagt     480
```

-continued

| | |
|---|---|
| aaactcccaa aaattggcca aggctcaaca agccaccgat ggcttgtctc aggaactcgt | 540 |
| tagtcttttg gatccgttgt tagctcaact atccgaatcc ttccactacc atgcagcgtt | 600 |
| ttgtttcctg tatatgtttg tttgcctatg cccccatgcc aagaatatta agttttcttt | 660 |
| aaagtctact ttacccatcg gtgctgggtt gggctcaagc gcctctattt ctgtatcact | 720 |
| ggccttagct atggcctact tggggggggtt aataggatct aatgacttgg aaaagctgtc | 780 |
| agaaaacgat aagcatatag tgaatcaatg ggccttcata ggtgaaaagt gtattcacgg | 840 |
| taccccttca ggaatagata acgctgtggc cacttatggt aatgccctgc tatttgaaaa | 900 |
| agactcacat aatggaacaa taaacacaaa caatttaag ttcttagatg atttcccagc | 960 |
| cattccaatg atcctaacct atactagaat tccaaggtct acaaaagatc ttgttgctcg | 1020 |
| cgttcgtgtg ttggtcaccg agaaatttcc tgaagttatg aagccaattc tagatgccat | 1080 |
| gggtgaatgt gccctacaag gcttagagat catgactaag ttaagtaaat gtaaaggcac | 1140 |
| cgatgacgag gctgtagaaa ctaataatga actgtatgaa caactattgg aattgataag | 1200 |
| aataaatcat ggactgcttg tctcaatcgg tgtttctcat cctggattag aacttattaa | 1260 |
| aaatctgagc gatgatttga gaattggctc cacaaaactt accggtgctg gtggcggcgg | 1320 |
| ttgctctttg actttgttac gaagagacat tactcaagag caaattgaca gcttcaaaaa | 1380 |
| gaaattgcaa gatgatttta gttacgagac atttgaaaca gacttgggtg ggactggctg | 1440 |
| ctgtttgtta agcgcaaaaa atttgaataa agatcttaaa atcaaatccc tagtattcca | 1500 |
| attatttgaa aataaaacta ccacaaagca acaaattgac gatctattat tgccaggaaa | 1560 |
| cacgaattta ccatggactt cataggaggc agatcaaatg tcagagttga gagccttcag | 1620 |
| tgccccaggg aaagcgttac tagctggtgg atatttagtt ttagatacaa aatatgaagc | 1680 |
| atttgtagtc ggattatcgg caagaatgca tgctgtagcc catccttacg gttcattgca | 1740 |
| agggtctgat aagtttgaag tgcgtgtgaa aagtaaacaa tttaaagatg gggagtggct | 1800 |
| gtaccatata agtcctaaaa gtggcttcat tcctgtttcg ataggcggat ctaagaaccc | 1860 |
| tttcattgaa aaagttatcg ctaacgtatt tagctacttt aaacctaaca tggacgacta | 1920 |
| ctgcaataga aacttgttcg ttattgatat tttctctgat gatgcctacc attctcagga | 1980 |
| ggatagcgtt accgaacatc gtggcaacag aagattgagt tttcattcgc acagaattga | 2040 |
| agaagttccc aaaacagggc tgggctcctc ggcaggttta gtcacagttt taactacagc | 2100 |
| tttggcctcc tttttttgtat cggacctgga aaataatgta gacaaatata gagaagttat | 2160 |
| tcataattta gcacaagttg ctcattgtca agctcagggt aaaattggaa gcgggtttga | 2220 |
| tgtagcggcg gcagcatatg gatctatcag atatagaaga ttcccacccg cattaatctc | 2280 |
| taatttgcca gatattggaa gtgctactta cggcagtaaa ctggcgcatt tggttgatga | 2340 |
| agaagactgg aatattacga ttaaaagtaa ccatttacct tcgggattaa ctttatggat | 2400 |
| gggcgatatt aagaatggtt cagaaacagt aaaactggtc cagaaggtaa aaattggta | 2460 |
| tgattcgcat atgccagaaa gcttgaaaat atatacagaa ctcgatcatg caaattctag | 2520 |
| atttatggat ggactatcta aactagatcg cttacgagag actcatgacg attacagcga | 2580 |
| tcagatattt gagtctcttg agaggaatga ctgtacctgt caaaagtatc ctgaaatcac | 2640 |
| agaagttaga gatgcagttg ccacaattag acgttccttt agaaaaataa ctaaagaatc | 2700 |
| tggtgccgat atcgaacctc ccgtacaaac tagcttattg gatgattgcc agaccttaaa | 2760 |
| aggagttctt acttgcttaa tacctggtgc tggtggttat gacgccattg cagtgattac | 2820 |
| taagcaagat gttgatctta gggctcaaac cgctaatgac aaaagatttt ctaaggttca | 2880 |

-continued

```
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attgggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaaagga    3720
aacaatgatg gattccaact cttttccatg cacatgtttg gactctttcc ctccaatatt    3780
ctacatgaat gacacttcca gcgtatcat cagttggtgc cacaccatta atcagttta    3840 cggagaaaca atcgttgcat acacgtttga tgcaggtcca aatgctgtgt tgtactactt    3900
agctgaaaat gagtcgaaac tctttgcatt tatctataaa ttgttggct ctgttcctgg    3960 atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattacg caaagactgg    4140 tctaccaaag gaataactgc agcccggggg atccactagt tctagagcgg ccgccaccgc    4200
ggtggagctc caattcgccc tatagtgagt cgtattacgc gcgctcactg gccgtcgttt    4260
tacaacgtcg tgactgggaa aaccctggcg ttacccaact taatcgcctt gcagcacatc    4320
cccctttcgc cagctggcgt aatagcgaag aggcccgcac cgatcgccct tcccaacagt    4380
tgcgcagcct gaatggcgaa tggaaattgt aagcgttaat attttgttaa aattcgcgtt    4440
aaatttttgt taaatcagct cattttttaa ccaataggcc ga                       4482
```

<210> SEQ ID NO 10
<211> LENGTH: 549
<212> TYPE: DNA
<213> ORGANISM: Escherichia coli

<400> SEQUENCE: 10

```
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttaccgc cgcgcactga gcaaaaaagc atggcctggc      180
gtgtggacta actcggtttg tgggcaccca caactgggag aaagcaacga agacgcagtg     240
atccgccgtt gccgttatga gcttggcgtg gaaattacgc ctcctgaatc tatctatcct     300
gactttcgct accgcgccac cgatccgagt ggcattgtgg aaaatgaagt gtgtccggta     360
tttgccgcac gcaccactag tgcgttacag atcaatgatg atgaagtgat ggattatcaa     420
tggtgtgatt tagcagatgt attacacggt attgatgcca cgccgtgggc gttcagtccg     480
```

| tggatggtga tgcaggcgac aaatcgcgaa gccagaaaac gattatctgc atttacccag | 540 |
| cttaaataa | 549 |

<210> SEQ ID NO 11
<211> LENGTH: 900
<212> TYPE: DNA
<213> ORGANISM: Escherichia coli

<400> SEQUENCE: 11

| atggactttc cgcagcaact cgaagcctgc gttaagcagg ccaaccaggc gctgagccgt | 60 |
| tttatcgccc cactgcccct tcagaacact cccgtggtcg aaaccatgca gtatggcgca | 120 |
| ttattaggtg gtaagcgcct gcgacctttc ctggtttatg ccaccggtca tatgttcggc | 180 |
| gttagcacaa acacgctgga cgcacccgct gccgccgttg agtgtatcca cgcttactca | 240 |
| ttaattcatg atgatttacc ggcaatggat gatgacgatc tgcgtcgcgg tttgccaacc | 300 |
| tgccatgtga agtttggcga agcaaacgcg attctcgctg cgacgctttt acaaacgctg | 360 |
| gcgttctcga ttttaagcga tgccgatatg ccggaagtgt cggaccgcga cagaatttcg | 420 |
| atgatttctg aactggcgag cgccagtggt attgccggaa tgtgcggtgg tcaggcatta | 480 |
| gatttagacg cggaaggcaa acacgtacct ctggacgcgc ttgagcgtat tcatcgtcat | 540 |
| aaaaccggcg cattgattcg cgccgccgtt cgccttggtg cattaagcgc cggagataaa | 600 |
| ggacgtcgtg ctctgccggt actcgacaag tatgcagaga gcatcggcct tgccttccag | 660 |
| gttcaggatg acatcctgga tgtggtggga gatactgcaa cgttgggaaa acgccagggt | 720 |
| gccgaccagc aacttggtaa aagtacctac cctgcacttc tgggtcttga gcaagcccgg | 780 |
| aagaaagccc gggatctgat cgacgatgcc cgtcagtcgc tgaaacaact ggctgaacag | 840 |
| tcactcgata cctcggcact ggaagcgcta gcggactaca tcatccagcg taataaataa | 900 |

<210> SEQ ID NO 12
<211> LENGTH: 5051
<212> TYPE: DNA
<213> ORGANISM: Artificial Sequence
<220> FEATURE:
<223> OTHER INFORMATION: Description of Artificial Sequence: Synthetic "MBI" operon nucleotide sequence

<400> SEQUENCE: 12

| gcgcaacgca attaatgtga gttagctcac tcattaggca ccccaggctt tacactttat | 60 |
| gcttccggct cgtatgttgt gtggaattgt gagcggataa caatttcaca caggaaacag | 120 |
| ctatgaccat gattacgcca agcgcgcaat taaccctcac taaagggaac aaaagctggg | 180 |
| taccgggccc cccctcgagg tcgacggtat cgataagctt gatatcgaat tcctgcagta | 240 |
| ggaggaatta accatgtcat taccgttctt aacttctgca ccgggaaagg ttattatttt | 300 |
| tggtgaacac tctgctgtgt acaacaagcc tgccgtcgct gctagtgtgt ctgcgttgag | 360 |
| aacctacctg ctaataagcg agtcatctgc accagatact attgaattgg acttcccgga | 420 |
| cattagcttt aatcataagt ggtccatcaa tgatttcaat gccatcaccg aggatcaagt | 480 |
| aaactcccaa aaattggcca aggctcaaca agccaccgat ggcttgtctc aggaactcgt | 540 |
| tagtcttttg gatccgttgt tagctcaact atccgaatcc ttccactacc atgcagcgtt | 600 |
| ttgtttcctg tatatgtttg tttgcctatg cccccatgcc aagaatatta agttttcttt | 660 |
| aaagtctact ttacccatcg gtgctgggtt gggctcaagc gcctctattt ctgtatcact | 720 |
| ggccttagct atggcctact tgggggggtt aataggatct aatgacttgg aaaagctgtc | 780 |

-continued

```
agaaaacgat aagcatatag tgaatcaatg ggccttcata ggtgaaaagt gtattcacgg    840
taccccttca ggaatagata acgctgtggc cacttatggt aatgccctgc tatttgaaaa    900
agactcacat aatggaacaa taaacacaaa caattttaag ttcttagatg atttcccagc    960
cattccaatg atcctaacct atactagaat tccaaggtct acaaaagatc ttgttgctcg    1020
cgttcgtgtg ttggtcaccg agaaattttc tgaagttatg aagccaattc tagatgccat    1080
gggtgaatgt gccctacaag gcttagagat catgactaag ttaagtaaat gtaaaggcac    1140
cgatgacgag gctgtagaaa ctaataatga actgtatgaa caactattgg aattgataag    1200
aataaatcat ggactgcttg tctcaatcgg tgtttctcat cctggattag aacttattaa    1260
aaatctgagc gatgatttga gaattggctc cacaaaactt accggtgctg gtggcggcgg    1320
ttgctctttg actttgttac gaagagacat tactcaagag caaattgaca gcttcaaaaa    1380
gaaattgcaa gatgatttta gttacgagac atttgaaaca gacttgggtg gactggctg    1440 ctgtttgtta agcgcaaaaa atttgaataa agatcttaaa atcaaatccc tagtattcca    1500
attatttgaa aataaaacta ccacaaagca acaaattgac gatctattat tgccaggaaa    1560
cacgaattta ccatggactt cataggaggc agatcaaatg tcagagttga gagccttcag    1620
tgccccaggg aaagcgttac tagctggtgg atatttagtt ttagatacaa aatatgaagc    1680
atttgtagtc ggattatcgg caagaatgca tgctgtagcc catccttacg gttcattgca    1740
agggtctgat aagtttgaag tgcgtgtgaa aagtaaacaa tttaaagatg gggagtggct    1800
gtaccatata agtcctaaaa gtggcttcat tcctgtttcg ataggcggat ctaagaaccc    1860
tttcattgaa aaagttatcg ctaacgtatt tagctacttt aaacctaaca tggacgacta    1920
ctgcaataga aacttgttcg ttattgatat tttctctgat gatgcctacc attctcagga    1980
ggatagcgtt accgaacatc gtggcaacag aagattgagt tttcattcgc acagaattga    2040
agaagttccc aaaacagggc tgggctcctc ggcaggttta gtcacagttt taactacagc    2100
tttggcctcc ttttttgtat cggacctgga aaataatgta gacaaatata gagaagttat    2160
tcataattta gcacaagttg ctcattgtca agctcaggt aaaattggaa gcgggtttga    2220
tgtagcggcg gcagcatatg gatctatcag atatagaaga ttcccacccg cattaatctc    2280
taatttgcca gatattggaa gtgctactta cggcagtaaa ctggcgcatt ggttgatga    2340 agaagactgg aatattacga ttaaaagtaa ccatttacct tcgggattaa ctttatggat    2400
gggcgatatt aagaatggtt cagaaacagt aaaactggtc cagaaggtaa aaaattggta    2460
tgattcgcat atgccagaaa gcttgaaaat atatacagaa ctcgatcatg caaattctag    2520
atttatggat ggactatcta aactagatcg cttacgagag actcatgacg attacagcga    2580
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
```

```
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaaagga    3720
aacaatgatg gattccaact ctttccatgc cacatgtttg gactctttcc ctccaatatt    3780
ctacatgaat gacacttcca gcgtatcat cagttggtgc cacaccatta atcagtttta     3840
cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200 atttttattga atgcacaggg agttcccacg ggtacgctgg aaaagtatgc cgcacacacg    4260
gcagacaccc gcttacatct cgcgttctcc agttggctgt ttaatgccaa aggacaatta    4320
ttagttaccc gccgcgcact gagcaaaaaa gcatggcctg cgtgtggac taactcggtt     4380 tgtgggcacc cacaactggg agaaagcaac gaagacgcag tgatccgccg ttgccgttat    4440
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattacacg gtattgatgc cacgccgtgg gcgttcagtc cgtggatggt gatgcaggcg    4680
acaaatcgcg aagccagaaa acgattatct gcatttaccc agcttaaata cccgggggga   4740
tccactagtt ctagagcggc cgccaccgcg gtggagctcc aattcgccct atagtgagtc    4800
gtattacgcg cgctcactgg ccgtcgtttt acaacgtcgt gactgggaaa accctggcgt    4860
tacccaactt aatcgccttg cagcacatcc cctttcgcc agctggcgta atagcgaaga    4920
ggcccgcacc gatcgccctt cccaacagtt gcgcagcctg aatggcgaat ggaaattgta    4980
agcgttaata ttttgttaaa attcgcgtta aattttgtt aaatcagctc attttttaac     5040
caataggccg a                                                        5051
```

<210> SEQ ID NO 13
<211> LENGTH: 5963
<212> TYPE: DNA
<213> ORGANISM: Artificial Sequence
<220> FEATURE:
<223> OTHER INFORMATION: Description of Artificial Sequence: Synthetic
      "MBIS" operon nucleotide sequence

<400> SEQUENCE: 13

```
gcgcaacgca attaatgtga gttagctcac tcattaggca ccccaggctt tacactttat       60
gcttccggct cgtatgttgt gtggaattgt gagcggataa caatttcaca caggaaacag      120
```

-continued

| | |
|---|---|
| ctatgaccat gattacgcca agcgcgcaat taaccctcac taaagggaac aaaagctggg | 180 |
| taccgggccc ccctcgagg tcgacggtat cgataagctt gatatcgaat tcctgcagta | 240 |
| ggaggaatta accatgtcat taccgttctt aacttctgca ccgggaaagg ttattatttt | 300 |
| tggtgaacac tctgctgtgt acaacaagcc tgccgtcgct gctagtgtgt ctgcgttgag | 360 |
| aacctacctg ctaataagcg agtcatctgc accagatact attgaattgg acttcccgga | 420 |
| cattagcttt aatcataagt ggtccatcaa tgatttcaat gccatcaccg aggatcaagt | 480 |
| aaactcccaa aaattggcca aggctcaaca agccaccgat ggcttgtctc aggaactcgt | 540 |
| tagtcttttg gatccgttgt tagctcaact atccgaatcc ttccactacc atgcagcgtt | 600 |
| ttgtttcctg tatatgtttg tttgcctatg ccccatgcc aagaatatta agttttcttt | 660 |
| aaagtctact ttacccatcg gtgctgggtt gggctcaagc gcctctattt ctgtatcact | 720 |
| ggccttagct atggcctact tgggggggtt aataggatct aatgacttgg aaaagctgtc | 780 |
| agaaaacgat aagcatatag tgaatcaatg ggccttcata ggtgaaaagt gtattcacgg | 840 |
| taccccttca ggaatagata cgctgtggc cacttatggt aatgcccctgc tatttgaaaa | 900 |
| agactcacat aatggaacaa taaacacaaa caattttaag ttcttagatg atttcccagc | 960 |
| cattccaatg atcctaacct atactagaat tccaaggtct acaaaagatc ttgttgctcg | 1020 |
| cgttcgtgtg ttggtcaccg agaaatttcc tgaagttatg aagccaattc tagatgccat | 1080 |
| gggtgaatgt gccctacaag cttagagat catgactaag ttaagtaaat gtaaaggcac | 1140 |
| cgatgacgag gctgtagaaa ctaataatga actgtatgaa caactattgg aattgataag | 1200 |
| aataaatcat ggactgcttg tctcaatcgg tgtttctcat cctggattag aacttattaa | 1260 |
| aaatctgagc gatgatttga gaattggctc cacaaaactt accggtgctg gtggcggcgg | 1320 |
| ttgctctttg actttgttac gaagagacat tactcaagag caaattgaca gcttcaaaaa | 1380 |
| gaaattgcaa gatgatttta gttacgagac atttgaaaca gacttgggtg ggactggctg | 1440 |
| ctgtttgtta agcgcaaaaa atttgaataa agatcttaaa atcaaatccc tagtattcca | 1500 |
| attatttgaa aataaaacta ccacaaagca acaaattgac gatctattat tgccaggaaa | 1560 |
| cacgaattta ccatggactt cataggaggc agatcaaatg tcagagttga gagccttcag | 1620 |
| tgccccaggg aaagcgttac tagctggtgg atatttagtt ttagatacaa aatatgaagc | 1680 |
| atttgtagtc ggattatcgg caagaatgca tgctgtagcc catccttacg gttcattgca | 1740 |
| agggtctgat aagtttgaag tgcgtgtgaa aagtaaacaa tttaaagatg gggagtggct | 1800 |
| gtaccatata agtcctaaaa gtggcttcat tcctgtttcg ataggcggat ctaagaaccc | 1860 |
| tttcattgaa aaagttatcg ctaacgtatt tagctacttt aaacctaaca tggacgacta | 1920 |
| ctgcaataga aacttgttcg ttattgatat tttctctgat gatgcctacc attctcagga | 1980 |
| ggatagcgtt accgaacatc gtggcaacag aagattgagt tttcattcgc acagaattga | 2040 |
| agaagttccc aaaacagggc tgggctcctc ggcaggttta gtcacagttt taactacagc | 2100 |
| tttggcctcc ttttttgtat cggacctgga aaataatgta gacaaatata gagaagttat | 2160 |
| tcataattta gcacaagttg ctcattgtca agctcagggt aaaattggaa gcgggtttga | 2220 |
| tgtagcggcg gcagcatatg gatctatcag atatagaaga ttcccacccg cattaatctc | 2280 |
| taatttgcca gatattggaa gtgctactta cggcagtaaa ctggcgcatt tggttgatga | 2340 |
| agaagactgg aatattacga ttaaaagtaa ccatttacct tcgggattaa ctttatggat | 2400 |
| gggcgatatt aagaatggtt cagaaacagt aaaactggtc cagaaggtaa aaattggta | 2460 |

```
tgattcgcat atgccagaaa gcttgaaaat atatacagaa ctcgatcatg caaattctag    2520
atttatggat ggactatcta aactagatcg cttacacgag actcatgacg attacagcga    2580
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attgggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taaagaaaga attgaacatg tcgtaccaaa    3660
gagatttgaa gtcatgcgta aagccattgt tgaaaaagat ttcgccacct ttgcaaagga    3720
aacaatgatg gattccaact cttttccatg ccacatgttt gactctttcc ctccaatatt    3780
ctacatgaat gacacttcca gcgtatcat cagttggtgc cacaccatta atcagttta    3840 cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200
attttattga atgcacaggg agttcccacg ggtacgctgg aaaagtatgc cgcacacacg    4260
gcagacaccc gcttacatct cgcgttctcc agttggctgt ttaatgccaa aggacaatta    4320
ttagttaccc gccgcgcact gagcaaaaaa gcatggcctg gcgtgtggac taactcggtt    4380
tgtgggcacc cacaactggg agaaagcaac gaagacgcag tgatccgccg ttgccgttat    4440
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattacacg gtattgatgc cacgccgtgg gcgttcagtc cgtggatggt gatgcaggcg    4680
acaaatcgcg aagccagaaa acgattatct gcatttaccc agcttaaata acccggggga    4740
tccactagtt ctagagcggc cgccaccgcg gaggaggaat gagtaatgga ctttccgcag    4800
caactcgaag cctgcgttaa gcaggccaac caggcgctga gccgttttat cgccccactg    4860
```

-continued

```
ccctttcaga acactcccgt ggtcgaaacc atgcagtatg cgcattatt aggtggtaag    4920 cgcctgcgac ctttcctggt ttatgccacc ggtcatatgt tcggcgttag cacaaacacg    4980
ctggacgcac ccgctgccgc cgttgagtgt atccacgctt actcattaat tcatgatgat    5040
ttaccggcaa tggatgatga cgatctgcgt cgcggtttgc caacctgcca tgtgaagttt    5100
ggcgaagcaa acgcgattct cgctggcgac gctttacaaa cgctggcgtt ctcgatttta    5160
agcgatgccg atatgccgga agtgtcggac cgcgacagaa tttcgatgat ttctgaactg    5220
gcgagcgcca gtggtattgc cggaatgtgc ggtggtcagg cattagattt agacgcggaa    5280
ggcaaacacg tacctctgga cgcgcttgag cgtattcatc gtcataaaac cggcgcattg    5340
attcgcgccg ccgttcgcct tggtgcatta agcgccggag ataaaggacg tcgtgctctg    5400
ccggtactcg acaagtatgc agagagcatc ggccttgcct tccaggttca ggatgacatc    5460
ctggatgtgg tgggagatac tgcaacgttg ggaaaacgcc agggtgccga ccagcaactt    5520
ggtaaaagta cctaccctgc acttctgggt cttgagcaag cccggaagaa agcccgggat    5580
ctgatcgacg atgcccgtca gtcgctgaaa caactggctg aacagtcact cgataccctcg    5640 gcactggaag cgctagcgga ctacatcatc cagcgtaata aataagagct ccaattcgcc    5700
ctatagtgag tcgtattacg cgcgctcact ggccgtcgtt ttacaacgtc gtgactggga    5760
aaaccctggc gttacccaac ttaatcgcct tgcagcacat ccccctttcg ccagctggcg    5820
taatagcgaa gaggcccgca ccgatcgccc ttcccaacag ttgcgcagcc tgaatggcga    5880
atggaaattg taagcgttaa tattttgtta aaattcgcgt taaattttg ttaaatcagc    5940 tcattttta accaataggc cga                                             5963
```

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 14
gatctgcagt aggaggaatt aaccatgcat taccgttctt aact                44

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 15
ttgatctgcc tcctatgaag tccatggtaa att                33

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 16
acttcatagg aggcagatca aatgtcagag ttgagagcct tc                42

<210> SEQ ID NO 17
<211> LENGTH: 33
<212> TYPE: DNA

<213> ORGANISM: Artificial Sequence
<220> FEATURE:
<223> OTHER INFORMATION: Description of Artificial Sequence: Primer

<400> SEQUENCE: 17
gagtattacc tcctatttat caagataagt ttc                            33

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 18
gataaatagg aggtaatact catgaccgtt tacacagcat cc                  42

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
tacctgcagt tattcctttg gtagaccagt                                30

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 20
gatgtcgact aggaggaata taaaatgaaa aattgtgtca tcgtc               45

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 21
ttagctgtcc tccttaattc aaccgttcaa tcac                           34

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 22
gatgtcgaca ggaggacagc taaatgaaac tctcaactaa actttg              46

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 23
agtgtaatcc tccttatttt ttaacatcgt aag                            33

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 24
ttaaaaaata aggaggatta cactatggtt ttaaccaata aaacag                46

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 25
atcgtcgact taggatttaa tgcaggtgac ggacc                             35

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 26
atcccgggag gaggattact atatgcaaac ggaacacgtc                        40

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 27
atcccgggtt atttaagctg ggtaaatg                                     28

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 28
agatccgcgg aggaggaatg agtaatggac tttccgcagc aac                    43

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 29
agtgagagct cttatttatt acgctggatg atg                               33

<210> SEQ ID NO 30
<211> LENGTH: 48
<212> TYPE: DNA
<213> ORGANISM: Artificial Sequence
<220> FEATURE:

```
<223> OTHER INFORMATION: Description of Artificial Sequence: Primer

<400> SEQUENCE: 30
ttgggctagc aggaggaatt caccatgagt tttgatattg ccaaatac                    48

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 31
tctgagcaac gaacgaagca tatatttatg tcctccaggc cttgattttg                  50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 32
caaaatcaag gcctggagga cataaatata tgcttcgttc gttgctcaga                  50

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 33
gcatccatgg tatcatcctc cgttgatgtg atg                                    33

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 34
tgataccatg gactttccgc agcaactcg                                         29

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 35
gtacatgcat ttatttatta cgctggatga tg                                     32

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 36
tgggtaccgg gccccccctc gcctctagag tcgactagga ggaattcacc atgagttttg       60
```

-continued

<210> SEQ ID NO 37
<211> LENGTH: 1641
<212> TYPE: DNA
<213> ORGANISM: Artemisia annua

<400> SEQUENCE: 37

| | |
|---|---|
| atggccctga ccgaagagaa accgatccgc cgatcgcta acttcccgcc gtctatctgg | 60 |
| ggtgaccagt tcctgatcta cgaaaagcag gttgagcagg gtgttgaaca gatcgtaaac | 120 |
| gacctgaaga agaagttcg tcagctgctg aaagaagctc tggacatccc gatgaaacac | 180 |
| gctaacctgc tgaaactgat cgacgagatc cagcgtctgg gtatcccgta ccacttcgaa | 240 |
| cgcgaaatcg accacgcact gcagtgcatc tacgaaacct acggcgacaa ctggaacggc | 300 |
| gaccgttctt ctctgtggtt tcgtctgatg cgtaaacagg ctactacgt tacctgtgac | 360 |
| gtttttaaca actacaagga caagaacggt gctttcaaac agtctctggc taacgacgtt | 420 |
| gaaggcctgc tgaactgta cgaagcgacc tccatgcgtg taccgggtga atcatcctg | 480 |
| gaggacgcgc tgggtttcac ccgttctcgt ctgtccatta tgactaaaga cgctttctct | 540 |
| actaacccgg ctctgttcac cgaaatccag cgtgctctga acagccgct gtggaaacgt | 600 |
| ctgccgcgta tcgaagcagc acagtacatt ccgttttacc agcagcagga ctctcacaac | 660 |
| aagaccctgc tgaaactggc taagctggaa ttcaacctgc tgcagtctct gcacaaagaa | 720 |
| gaactgtctc acgtttgtaa gtggtggaag catttgaca tcaagaaaaa cgcgccgtgc | 780 |
| ctgcgtgacc gtatcgttga atgttacttc tggggtctgg ttctggtta tgaaccacag | 840 |
| tactcccgtg cacgtgtgtt cttcactaaa gctgtagctg ttatcacct gatcgatgac | 900 |
| acttacgatg cttacggcac ctacgaagaa ctgaagatct ttactgaagc tgtagaacgc | 960 |
| tggtctatca cttgcctgga cactctgccg gagtacatga aaccgatcta caaactgttc | 1020 |
| atggatacct acaccgaaat ggaggaattc ctggcaaaag aaggccgtac cgacctgttc | 1080 |
| aactgcggta aagagtttgt taagaattc gtacgtaacc tgatggttga agctaaatgg | 1140 |
| gctaacgaag ccatatccc gactaccgaa gaacatgacc cggttgttat catcaccggc | 1200 |
| ggtgcaaacc tgctgaccac cacttgctat ctgggtatgt ccgacatctt taccaaggaa | 1260 |
| tctgttgaat gggctgtttc tgcaccgccg ctgttccgtt actccggtat tctgggtcgt | 1320 |
| cgtctgaacg acctgatgac ccacaaagca gagcaggaac gtaaacactc ttcctcctct | 1380 |
| ctggaatcct acatgaagga atataacgtt aacgaggagt acgcacagac tctgatctat | 1440 |
| aaagaagttg aagacgtatg gaaagacatc aaccgtgaat acctgactac taaaaacatc | 1500 |
| ccgcgcccgc tgctgatggc agtaatctac ctgtgccagt tcctggaagt acagtacgct | 1560 |
| ggtaaagata acttcactcg catgggcgac gaatacaaac acctgatcaa atccctgctg | 1620 |
| gtttacccga tgtccatctg a | 1641 |

<210> SEQ ID NO 38
<211> LENGTH: 548
<212> TYPE: PRT
<213> ORGANISM: Artemisia annua

<400> SEQUENCE: 38

Met Ala Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
            20                  25                  30

Gln Gly Val Glu Gln Ile Val Asn Asp Leu Lys Lys Glu Val Arg Gln
        35                  40                  45

```
Leu Leu Lys Glu Ala Leu Asp Ile Pro Met Lys His Ala Asn Leu Leu
     50                  55                  60

Lys Leu Ile Asp Glu Ile Gln Arg Leu Gly Ile Pro Tyr His Phe Glu
 65                  70                  75                  80

Arg Glu Ile Asp His Ala Leu Gln Cys Ile Tyr Glu Thr Tyr Gly Asp
                 85                  90                  95

Asn Trp Asn Gly Asp Arg Ser Ser Leu Trp Phe Arg Leu Met Arg Lys
                100                 105                 110

Gln Gly Tyr Tyr Val Thr Cys Asp Val Phe Asn Asn Tyr Lys Asp Lys
                115                 120                 125

Asn Gly Ala Phe Lys Gln Ser Leu Ala Asn Asp Val Glu Gly Leu Leu
    130                 135                 140

Glu Leu Tyr Glu Ala Thr Ser Met Arg Val Pro Gly Glu Ile Ile Leu
145                 150                 155                 160

Glu Asp Ala Leu Gly Phe Thr Arg Ser Arg Leu Ser Ile Met Thr Lys
                165                 170                 175

Asp Ala Phe Ser Thr Asn Pro Ala Leu Phe Thr Glu Ile Gln Arg Ala
                180                 185                 190

Leu Lys Gln Pro Leu Trp Lys Arg Leu Pro Arg Ile Glu Ala Ala Gln
    195                 200                 205

Tyr Ile Pro Phe Tyr Gln Gln Asp Ser His Asn Lys Thr Leu Leu
    210                 215                 220

Lys Leu Ala Lys Leu Glu Phe Asn Leu Leu Gln Ser Leu His Lys Glu
225                 230                 235                 240

Glu Leu Ser His Val Cys Lys Trp Trp Lys Ala Phe Asp Ile Lys Lys
                245                 250                 255

Asn Ala Pro Cys Leu Arg Asp Arg Ile Val Glu Cys Tyr Phe Trp Gly
                260                 265                 270

Leu Gly Ser Gly Tyr Glu Pro Gln Tyr Ser Arg Ala Arg Val Phe Phe
                275                 280                 285

Thr Lys Ala Val Ala Val Ile Thr Leu Ile Asp Asp Thr Tyr Asp Ala
290                 295                 300

Tyr Gly Thr Tyr Glu Glu Leu Lys Ile Phe Thr Glu Ala Val Glu Arg
305                 310                 315                 320

Trp Ser Ile Thr Cys Leu Asp Thr Leu Pro Glu Tyr Met Lys Pro Ile
                325                 330                 335

Tyr Lys Leu Phe Met Asp Thr Tyr Thr Glu Met Glu Glu Phe Leu Ala
                340                 345                 350

Lys Glu Gly Arg Thr Asp Leu Phe Asn Cys Gly Lys Glu Phe Val Lys
                355                 360                 365

Glu Phe Val Arg Asn Leu Met Val Glu Ala Lys Trp Ala Asn Glu Gly
    370                 375                 380

His Ile Pro Thr Thr Glu Glu His Asp Pro Val Val Ile Ile Thr Gly
385                 390                 395                 400

Gly Ala Asn Leu Leu Thr Thr Thr Cys Tyr Leu Gly Met Ser Asp Ile
                405                 410                 415

Phe Thr Lys Glu Ser Val Glu Trp Ala Val Ser Ala Pro Leu Phe
                420                 425                 430

Arg Tyr Ser Gly Ile Leu Gly Arg Leu Asn Asp Leu Met Thr His
    435                 440                 445

Lys Ala Glu Gln Glu Arg Lys His Ser Ser Ser Leu Glu Ser Tyr
450                 455                 460
```

| Met | Lys | Glu | Tyr | Asn | Val | Asn | Glu | Gly | Tyr | Ala | Gln | Thr | Leu | Ile | Tyr |
| 465 | | | | | 470 | | | | | 475 | | | | | 480 |

| Lys | Glu | Val | Glu | Asp | Val | Trp | Lys | Asp | Ile | Asn | Arg | Glu | Tyr | Leu | Thr |
| | | | | 485 | | | | | 490 | | | | | 495 | |

| Thr | Lys | Asn | Ile | Pro | Arg | Pro | Leu | Leu | Met | Ala | Val | Ile | Tyr | Leu | Cys |
| | | | 500 | | | | | 505 | | | | | 510 | | |

| Gln | Phe | Leu | Glu | Val | Gln | Tyr | Ala | Gly | Lys | Asp | Asn | Phe | Thr | Arg | Met |
| | | 515 | | | | | 520 | | | | | 525 | | | |

| Gly | Asp | Glu | Tyr | Lys | His | Leu | Ile | Lys | Ser | Leu | Leu | Val | Tyr | Pro | Met |
| | 530 | | | | | 535 | | | | | 540 | | | | |

| Ser | Ile | Trp | Ser |
| 545 | | | |

<210> SEQ ID NO 39
<211> LENGTH: 1644
<212> TYPE: DNA
<213> ORGANISM: Artemisia annua

<400> SEQUENCE: 39

```
atgagcctga tcgtagagga cgtaatccgg ccgaacgcta acttcccgtc tgagatctgg      60
ggtgaccagt tcctggcata cgaccaggac gaacaggaag gtgttgaaca ggttatcaaa     120
gacctgaaag aagaagttaa atctgagctg ctgaccgctc tgaactcccc gactcagcac     180
actgaactgc tgaaattcat cgacgcgatc gagcgtctgg gtatcgctta ctacttcgaa     240
gaagaaatca accaggtatt tcagcacatg tacaccgctt acggcgacaa gtggaccggt     300
ggcaacactt ctctgtggtt ccgtctgatg cgtcagcacg gtttcttcgt aagctctgac     360
atcttctcca cctacaagga caaggaaggt cgtttcaaag aatctctgga aaagacgtt     420
cacggcctgc tggaactgta cgaagcggca tacatgtttg taccgggtga aggcatcctg     480
gacgacgcgc tggtcttcac ccgtacttgt ctggacgaga tcgctaagaa cccgtccctg     540
tctaactccg ctgtatcctc ccagatccgt gaagctctga ctcagccgct gcataagcgt     600
ctgccgcgtc tggaagcact gcgttacatc ccgttctacc agcagcaggc atctcactcc     660
gagaccctgc tgaaactggc taagctgggt ttcaaccagc tgcagtctct gcacaagaaa     720
gaactgtcta tcatttctaa atggtggaaa tctttcgacg ttgctaacaa cctgccgtac     780
gctcgtaacc gtccggttga atgctacttc tgggctctgg ctgtgtactt tgaaccacag     840
tactccgagt ctcgtgtctt cctgtctcgt ttcttctcta tccagacctt cctggatgac     900
acttacgatg cttacggcac ctacgaagaa ctggagcagt ttactgaagc tatccagcgt     960
tggtctatca cttgcctgga cggtctgccg gagtccatga aactgatctt ccagatgctg    1020
gtaaagatct tcgaagaaat cgaagaaatc ctgtctaaag acggcaaaca gcaccacgtt    1080
aactacatca agagactctg aaagaagca gtacagtcct atatgactga agctcgttgg    1140
gctaaagaag aatacatccc gactatcgaa gaacatacca agtttcttta catctccatc    1200
ggttacaagc tggcgctggt tgctggcttt gcttgtatgg gcgacgttat cgcggatgac    1260
tctttcgaat gggtatttac caaccctccg ctggtaaacg cttgctgtct gctgtgccgt    1320
actatggacg acctgggctc ccacaaaggc gagcaggacc gtaaacacgt tgcttccact    1380
atcgaatgct acatgaagca gtttgacgct agcgagcagc aggcatacga atctctgaac    1440
aagaaagttg aagacgcatg gaaagaaatc aaccgtgaat tcatgatcac ttgtaaagac    1500
gtaaacatcc atgtagcgat gcgtgtactg aacttctccc gctccgttga cgtactgtac    1560
aagaacaaag atcacttcac tcacgttggt gtagaagtta tcaaccacat caaatccctg    1620
```
ttcgttgacg cgatcatcac ctga 1644

<210> SEQ ID NO 40
<211> LENGTH: 551
<212> TYPE: PRT
<213> ORGANISM: Artemisia annua

<400> SEQUENCE: 40

```
Met Ser Leu Ile Val Glu Asp Val Ile Arg Pro Asn Ala Asn Phe Pro
  1               5                  10                  15

Ser Glu Ile Trp Gly Asp Gln Phe Leu Ala Tyr Asp Gln Asp Glu Gln
             20                  25                  30

Glu Gly Val Glu Gln Val Ile Lys Asp Leu Lys Glu Val Lys Ser
         35                  40                  45

Glu Leu Leu Thr Ala Leu Asn Ser Pro Thr Gln His Thr Glu Leu Leu
 50                  55                  60

Lys Phe Ile Asp Ala Ile Glu Arg Leu Gly Ile Ala Tyr Tyr Phe Glu
 65                  70                  75                  80

Glu Glu Ile Asn Gln Val Phe Gln His Met Tyr Thr Ala Tyr Gly Asp
             85                  90                  95

Lys Trp Thr Gly Gly Asn Thr Ser Leu Trp Phe Arg Leu Met Arg Gln
            100                 105                 110

His Gly Phe Phe Val Ser Ser Asp Ile Phe Ser Thr Tyr Lys Asp Lys
            115                 120                 125

Glu Gly Arg Phe Lys Glu Ser Leu Glu Lys Asp Val His Gly Leu Leu
        130                 135                 140

Glu Leu Tyr Glu Ala Ala Tyr Met Phe Val Pro Gly Glu Gly Ile Leu
145                 150                 155                 160

Asp Asp Ala Leu Val Phe Thr Arg Thr Cys Leu Asp Glu Ile Ala Lys
                165                 170                 175

Asn Pro Ser Leu Ser Asn Ser Ala Val Ser Ser Gln Ile Arg Glu Ala
            180                 185                 190

Leu Thr Gln Pro Leu His Lys Arg Leu Pro Arg Leu Glu Ala Leu Arg
        195                 200                 205

Tyr Ile Pro Phe Tyr Gln Gln Gln Ala Ser His Ser Glu Thr Leu Leu
    210                 215                 220

Lys Leu Ala Lys Leu Gly Phe Asn Gln Leu Gln Ser Leu His Lys Lys
225                 230                 235                 240

Glu Leu Ser Ile Ile Ser Lys Trp Trp Lys Ser Phe Asp Val Ala Asn
                245                 250                 255

Asn Leu Pro Tyr Ala Arg Asn Arg Pro Val Glu Cys Tyr Phe Trp Ala
            260                 265                 270

Leu Ala Val Tyr Phe Glu Pro Gln Tyr Ser Glu Ser Arg Val Phe Leu
        275                 280                 285

Ser Arg Phe Phe Ser Ile Gln Thr Phe Leu Asp Asp Thr Tyr Asp Ala
    290                 295                 300

Tyr Gly Thr Tyr Glu Glu Leu Glu Gln Phe Thr Glu Ala Ile Gln Arg
305                 310                 315                 320

Trp Ser Ile Thr Cys Leu Asp Gly Leu Pro Glu Ser Met Lys Leu Ile
                325                 330                 335

Phe Gln Met Leu Val Lys Ile Phe Glu Glu Ile Glu Glu Ile Leu Ser
            340                 345                 350

Lys Asp Gly Lys Gln His Val Asn Tyr Ile Lys Glu Thr Leu Lys
        355                 360                 365
```

```
Glu Ala Val Gln Ser Tyr Met Thr Glu Ala Arg Trp Ala Lys Glu Glu
    370                 375                 380

Tyr Ile Pro Thr Ile Glu Glu His Thr Lys Val Ser Tyr Ile Ser Ile
385                 390                 395                 400

Gly Tyr Lys Leu Ala Leu Val Ala Gly Phe Ala Cys Met Gly Asp Val
                405                 410                 415

Ile Ala Asp Asp Ser Phe Glu Trp Val Phe Thr Asn Pro Pro Leu Val
                420                 425                 430

Asn Ala Cys Cys Leu Leu Cys Arg Thr Met Asp Asp Leu Gly Ser His
                435                 440                 445

Lys Gly Glu Gln Asp Arg Lys His Val Ala Ser Thr Ile Glu Cys Tyr
450                 455                 460

Met Lys Gln Phe Asp Ala Ser Glu Gln Gln Ala Tyr Glu Ser Leu Asn
465                 470                 475                 480

Lys Lys Val Glu Asp Ala Trp Lys Glu Ile Asn Arg Glu Phe Met Ile
                485                 490                 495

Thr Cys Lys Asp Val Asn Ile His Val Ala Met Arg Val Leu Asn Phe
                500                 505                 510

Ser Arg Ser Val Asp Val Leu Tyr Lys Asn Lys Asp His Phe Thr His
                515                 520                 525

Val Gly Val Glu Val Ile Asn His Ile Lys Ser Leu Phe Val Asp Ala
                530                 535                 540

Ile Ile Thr Trp Ser Arg Asp
545                 550

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gattaaggca tgcaccatgg ccctgaccga agagaaaccg                          40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
atccgcccga tcgctaactt cccgccgtct atctggggtg                          40

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
accagttcct gatctacgaa aagcaggttg agcagggtg                           39

<210> SEQ ID NO 44
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttgaacagat cgtaaacgac ctgaagaaag aagttcgtca gc                           42

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgctgaaaga agctctggac atcccgatga aacacgctaa c                            41

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctgctgaaac tgatcgacga gatccagcgt ctgggtatc                               39

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccgtaccact tcgaacgcga aatcgaccac gcactgcag                               39

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgcatctacg aaacctacgg cgacaactgg aacggcgacc                              40

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gttcttctct gtggtttcgt ctgatgcgta aacagggcta c                            41

<210> SEQ ID NO 50
<211> LENGTH: 39
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 50
tacgttacct gtgacgtttt taacaactac aaggacaag                              39

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aacggtgctt tcaaacagtc tctggctaac gacgttgaag                             40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcctgctgga actgtacgaa gcgacctcca tgcgtgtacc                             40

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggtgaaatc atcctggagg acgcgctggg tttcacccg                              39

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttctcgtctg tccattatga ctaaagacgc tttctctact aac                         43

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ccggctctgt tcaccgaaat ccagcgtgct ctgaaacag                              39

<210> SEQ ID NO 56
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 56
ccgctgtgga aacgtctgcc gcgtatcgaa gcagcacag                              39

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tacattccgt tttaccagca gcaggactct cacaacaag                              39

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
accctgctga aactggctaa gctggaattc aacctgctgc                             40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
agtctctgca caaagaagaa ctgtctcacg tttgtaagtg                             40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtggaaggca tttgacatca agaaaaacgc gccgtgcctg                             40

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cgtgaccgta tcgttgaatg ttacttctgg ggtctgggtt c                           41

<210> SEQ ID NO 62
<211> LENGTH: 40
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 62
tggttatgaa ccacagtact cccgtgcacg tgtgttcttc                    40

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
actaaagctg tagctgttat caccctgatc gatgacactt ac                 42

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gatgcttacg gcacctacga agaactgaag atctttactg                    40

<210> SEQ ID NO 65
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aagctgtaga acgctggtct atcacttgcc tggacactc                     39

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgccggagta catgaaaccg atctacaaac tgttcatgg                     39

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atacctacac cgaaatggag gaattcctgg caaaagaagg                    40

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic

<400> SEQUENCE: 68
ccgtaccgac ctgttcaact gcggtaaaga gtttgttaaa g    41

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aattcgtacg taacctgatg gttgaagcta aatgggctaa c    41

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaaggccata tcccgactac cgaagaacat gacccggttg    40

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttatcatcac cggcggtgca aacctgctga ccaccacttg    40

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctatctgggt atgtccgaca tctttaccaa ggaatctgtt g    41

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
aatgggctgt ttctgcaccg ccgctgttcc gttactccg    39

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtattctggg tcgtcgtctg aacgacctga tgacccacaa ag        42

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagcagga acgtaaacac tcttcctcct ctctggaatc        40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ctacatgaag gaatataacg ttaacgagga gtacgcacag        40

<210> SEQ ID NO 77
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
actctgatct ataaagaagt tgaagacgta tggaaagac        39

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
atcaaccgtg aatacctgac tactaaaaac atcccgcgcc        40

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cgctgctgat ggcagtaatc tacctgtgcc agttcctgg        39

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 80
aagtacagta cgctggtaaa gataacttca ctcgcatggg                    40

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgacgaatac aaacacctga tcaaatccct gctggtttac                    40

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccgatgtcca tctgatcccg ggattagat                                29

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctaattccgt acgtggtacc                                          20

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gggactggct tctctttggc taggcgggct agcgattgaa                    40

<210> SEQ ID NO 85
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggcggcaga tagaccccac tggtcaagga ctagatgctt t                  41

<210> SEQ ID NO 86
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
```
tcgtccaact cgtcccacaa cttgtctagc atttgctgga ct                               42

<210> SEQ ID NO 87
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tctttcttca agcagtcgac gactttcttc gagacct                                    37

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gtagggctac tttgtgcgat tggacgactt tgactagctg                                 40

<210> SEQ ID NO 89
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctctaggtcg cagacccata gggcatggtg aagcttgcg                                  39

<210> SEQ ID NO 90
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctttagctgg tgcgtgacgt cacgtagatg ctttggatgc c                               41

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gctgttgacc ttgccgctgg caagaagaga caccaaagca                                 40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92

```
gactacgcat ttgtcccgat gatgcaatgg acactgcaaa                    40
```

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93

```
aattgttgat gttcctgttc ttgccacgaa agtttgtcag a                  41
```

<210> SEQ ID NO 94
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94

```
gaccgattgc tgcaacttcc ggacgacctt gacatgctt                     39
```

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95

```
cgctggaggt acgcacatgg cccactttag taggacctc                     39
```

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

```
ctgcgcgacc caaagtgggc aagagcagac aggtaatact                    40
```

<210> SEQ ID NO 97
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

```
gatttctgcg aaagagatga ttgggccgag acaagtggct t                  41
```

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98

```
taggtcgcac gagactttgt cggcgacacc tttgcagacg                    40
```

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
gcgcatagct tcgtcgtgtc atgtaaggca aaatggtcgt                            40

<210> SEQ ID NO 100
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
cgtcctgaga gtgttgttct gggacgactt tgaccgatt                             39

<210> SEQ ID NO 101
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cgaccttaag ttggacgacg tcagagacgt gtttctt                               37

<210> SEQ ID NO 102
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
cttgacagag tgcaaacatt caccaccttc cgtaaactgt a                          41

<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103 gttcttttg cgcggcacgg acgcactggc atagcaactt a                           41

<210> SEQ ID NO 104
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
caatgaagac cccagaccca agaccaatac ttggtgtcat ga                         42

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gggcacgtgc acacaagaag tgatttcgac atcgacaata                                40

<210> SEQ ID NO 106
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtgggactag ctactgtgaa tgctacgaat gccgtggatg                                40

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cttcttgact tctagaaatg acttcgacat cttgcgacca                                40

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gatagtgaac ggacctgtga gacggcctca tgtactttgg                                40

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctagatgttt gacaagtacc tatggatgtg gctttacctc                                40

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cttaaggacc gttttcttcc ggcatggctg gacaagttga                                40

<210> SEQ ID NO 111
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cgccatttct caaacaattt cttaagcatg cattggacta c                            41

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
caacttcgat ttacccgatt gcttccggta tagggctgat                              40

<210> SEQ ID NO 113
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggcttcttgt actgggccaa caatagtagt ggccgccac                               39

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gtttggacga ctggtggtga acgatagacc catacaggct                              40

<210> SEQ ID NO 115
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gtagaaatgg ttccttagac aacttacccg acaaagacgt g                            41

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcggcgacaa ggcaatgagg ccataagacc cagcagcaga                              40

<210> SEQ ID NO 117

<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
cttgctggac tactgggtgt ttcgtctcgt ccttgcattt                40

<210> SEQ ID NO 118
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gtgagaagga ggagagacct taggatgtac ttccttatat t              41

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
gcaattgctc ctcatgcgtg tctgagacta gatatttctt              40

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
caacttctgc ataccttcct gtagttggca cttatggact              40

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
gatgattttt gtagggcgcg ggcgacgact accgtcatta              40

<210> SEQ ID NO 122
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
gatggacacg gtcaaggacc ttcatgtcat gcgaccattt              40

<210> SEQ ID NO 123
<211> LENGTH: 38

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctattgaagt gagcgtaccc gctgcttatg tttgtgga                            38

<210> SEQ ID NO 124
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctagtttagg gacgaccaaa tgggctacag gtagactagg gccctaatct a             51
```